… … …

(12) United States Patent
Wang et al.

(10) Patent No.: US 10,710,993 B2
(45) Date of Patent: Jul. 14, 2020

(54) BENZOFURAN PYRAZOLE AMINE KINASE INHIBITOR

(71) Applicant: Hangzhou REX Pharmaceutical Co., LTD., Hangzhou, Zhejiang (CN)

(72) Inventors: Yonghui Wang, Zhejiang (CN); Juan Zhou, Zhejiang (CN); Yujun Gao, Zhejiang (CN); Dong Wang, Zhejiang (CN); Binbin Hong, Zhejiang (CN); Ximing Shen, Zhejiang (CN); Yaodong Wu, Zhejiang (CN); Chunqi Li, Zhejiang (CN)

(73) Assignee: HANGZHOU REX PHARMACEUTICAL CO., LTD., Hangzhou, Zhejiang (CN)

( * ) Notice: Subject to any disclaimer, the term of this patent is extended or adjusted under 35 U.S.C. 154(b) by 0 days.

(21) Appl. No.: 16/313,716

(22) PCT Filed: Jun. 27, 2017

(86) PCT No.: PCT/CN2017/090392
§ 371 (c)(1),
(2) Date: Dec. 27, 2018

(87) PCT Pub. No.: WO2018/001251
PCT Pub. Date: Jan. 4, 2018

(65) Prior Publication Data
US 2019/0225600 A1   Jul. 25, 2019

(30) Foreign Application Priority Data
Jun. 27, 2016  (CN) .......................... 2016 1 0487793

(51) Int. Cl.
| C07D 413/14 | (2006.01) |
| A61P 35/00 | (2006.01) |
| A61K 31/506 | (2006.01) |
| C07D 491/22 | (2006.01) |
| C07D 405/14 | (2006.01) |

(52) U.S. Cl.
CPC .......... *C07D 413/14* (2013.01); *A61K 31/506* (2013.01); *A61P 35/00* (2018.01); *C07D 405/14* (2013.01); *C07D 491/22* (2013.01)

(58) Field of Classification Search
CPC .. C07D 413/14; C07D 405/14; C07D 491/22; A61P 35/00; A61K 31/506

USPC ......................................................... 544/333
See application file for complete search history.

(56) References Cited

U.S. PATENT DOCUMENTS

| 2014/0128387 A1* | 5/2014 | Wang | ................... C07D 405/12 514/233.5 |
| 2016/0145244 A1* | 5/2016 | Wang | ................... C07D 405/14 514/245 |
| 2017/0247392 A1* | 8/2017 | Dong | ................... C07D 403/12 |

FOREIGN PATENT DOCUMENTS

| WO | WO03026665 A1 | 4/2003 | |
| WO | WO-2005016894 A1 * | 2/2005 | ........... C04B 35/632 |
| WO | WO-2009032668 A2 * | 3/2009 | ........... C07D 239/48 |
| WO | WO-2011120025 A1 * | 9/2011 | ........... C07D 403/12 |
| WO | WO2011120026 A1 | 9/2011 | |
| WO | WO-2014071832 A1 * | 5/2014 | ......... A61K 31/5377 |
| WO | WO2015089337 A1 | 6/2015 | |
| WO | WO-2015180685 A1 * | 12/2015 | ........... C07D 471/04 |
| WO | WO-2016050171 A1 * | 4/2016 | ........... C07D 405/14 |

OTHER PUBLICATIONS

Cohen; Eur. J. Biochem. 2001, 268, 5001-5010. (Year: 2001).*
Ferguson; Nature Reviews Drug Discovery 2018,17, 353-377. (Year: 2018).*
Shaw; Clin Cancer Res 2011, 17, 2081-2086. (Year: 2011).*
Zhang; Bioorg. Med. Chem. Lett. 2015, 25, 3738-3743. (Year: 2015).*
Office action in related Japanese Patent Application No. 2018-569104, dated Oct. 15, 2019. Machine Translation. (Year: 2019).*
Search Opinion and Supplementary Search Report in related European Application EP 17819248.0, dated Dec. 18, 2019. (Year: 2019).*

* cited by examiner

*Primary Examiner* — Daniel R Carcanague
(74) *Attorney, Agent, or Firm* — Muncy, Geissler, Olds & Lowe, P.C.

(57) ABSTRACT

The present invention discloses a compound for regulating protein kinase activity and used for treating or preventing diseases associated with protein kinases. Specifically, the present invention relates to a benzofuran pyrazole amine protein kinase inhibitor which belongs to compounds that regulate anaplastic lymphoma kinase (ALK), and provides a method of preparing such a compound and a pharmaceutical use of such a compound in the treatment or prevention of diseases associated with ALK. The inhibitor can solve the problem of the drug resistance of the first generation and the second generation of ALK inhibitors.

17 Claims, 3 Drawing Sheets

BENZOFURAN PYRAZOLE AMINE KINASE INHIBITOR

TECHNICAL FIELD

The present invention relates to a compound for regulating protein kinase activity and preventing or treating diseases associated with protein kinases. Specifically, the present invention relates to a benzofuran pyrazole amine protein kinase inhibitor which belongs to compounds that regulate anaplastic lymphoma kinase (ALK) activity, and provides a method of preparing such a compound and a pharmaceutical use of such a compound in the prevention or treatment of diseases associated with ALK.

BACKGROUND

Malignant tumors are a common and frequently-occurring disease that seriously threatens human health, which are characterized by abnormal proliferation of cells or mutant cells. The proliferation, apoptosis and metastasis of tumor cells are closely related to the abnormality of a certain link in a series of signal transduction pathways inside and outside the cell. In these signaling pathways, a class of important molecule is protein kinase. The abnormality of protein kinase is closely related to the occurrence, development, prognosis and outcome of tumors, and is also the main cause of a series of other human diseases associated with inflammation or proliferative response. The development of drugs for targeting protein kinases is the main mean of treating related diseases. Many drugs have been approved for marketing. Such drugs have the characteristics of clear target, clear curative effect and high safety, and thus are increasingly recognised and supported in clinical medical practice.

Anaplastic lymphoma kinase (ALK) is an important member of the protein kinase family. Existing studies have shown that the overexpression, mutations and fusion proteins of ALK are directly related to various tumors, including but not limited to neuroblastoma, anaplastic large cell lymph tumor (ALCL), non-small cell lung cancer (NSCLC), inflammatory myofibroblastic tumor (IMT) and the like. The first-generation drug Crizotinib and the second-generation drug Ceritinib against for the ALK fusion gene have been marketed in 2011 and 2014, respectively, and the therapy thereof for patients with ALK-positive lung cancer has obtained significant progression free survival and objective response rate, which confirms the definite clinical value of this target. Despite the significant efficacy, due to the heterogeneity of tumors and the adaptation of tumor cells to environmental stress, more and more research reports indicate that drug-resistance of tumors and disease progression are still the inevitable fate of such patients. Furthermore, serious adverse reactions of these existing drugs, such as excessive incidence of adverse reactions in the digestive tract, hepatotoxicity and prolonged QT interval, also limit the application of such drugs.

For example, Luc Friboulet, Nanxin Li, Ryohei Katayama, Jeffrey A Engelman et al. found that: in about one year after the treatment with the first-generation ALK inhibitor Crizotininb, the drug-resistance occurred for most patients mainly by the mutation site of L1196M, G1269A, S1206Y and I1171T, among which L1196M is a gated site; and although the second-generation ALK inhibitor Ceritinib can solve the problem of the drug-resistance of the first-generation ALK inhibitor, the drug-resistance phenomenon of Ceritinib for G1202R, C1156Y, 1151T-ins, L1152R and F1174C mutation sites also occurred (The ALK Inhibitor Ceritinib Overcomes Crizotinib Resistance in Non-Small Cell Lung Cancer; Cancer Discov; April 2014; 4(6): 662-673.).

In view of this, it is of important social benefit and value for solving the above problems that new compounds with good ALK inhibitory activity and safety continue to be developed and further marketed.

SUMMARY OF THE INVENTION

The object of the present invention is to provide a benzofuran pyrazole amine protein kinase inhibitor with a novel structure, wherein a series of compounds with an anti-tumor activity are synthesized through the substitution and modification of groups and screened.

In order to achieve the above-mentioned object, the present invention adopts the following technical solution:

a benzofuran pyrazole amine protein kinase inhibitor is a compound having the following general structural formula (I) or a pharmaceutically acceptable salt thereof:

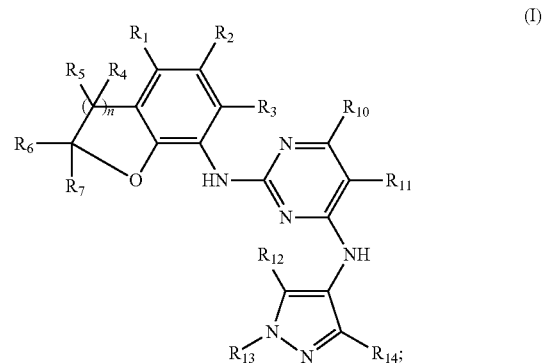

wherein $R_1$ is selected from

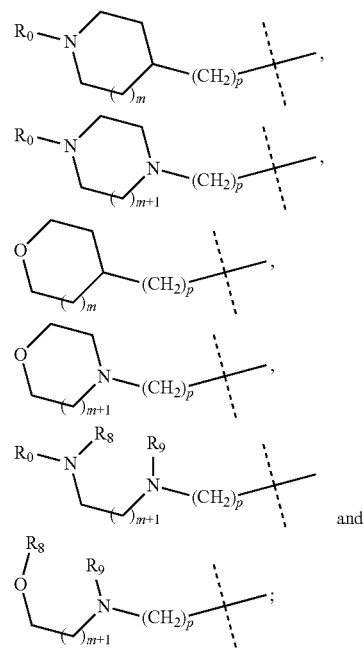

$R_0$, $R_8$ and $R_9$ are each independently selected from one or more of the group consisting of hydrogen, $C_{1-6}$ alkyl, $C_{2-6}$ alkenyl, $C_{2-6}$ alkynyl, acyl, amido, sulfo group, sulfanilamido, hydroxyl, aryl and heterocyclyl; $R_2$, $R_3$, $R_4$, $R_5$, $R_6$, $R_7$, $R_{10}$ and $R_{11}$ are each independently selected from the group consisting of hydrogen, halogen, $C_{1-6}$ alkyl, halogenated $C_{1-6}$ alkyl, $C_{1-6}$ alkoxy, halogenated $C_{1-6}$ alkoxy, $C_{2-6}$ alkenyl, $C_{2-6}$ alkynyl, cyano or amino; $R_{13}$ is selected from one or more of the group consisting of hydrogen, $C_{1-6}$ alkoxy, $C_{1-6}$ alkyl, $C_{3-6}$ cycloalkyl, $C_{2-6}$ alkenyl, $C_{2-6}$ alkynyl, amido, boryl, amino, hydroxyl, cyano, carbonyl, carboxy, aryl and heterocyclyl; $R_{12}$ and $R_{14}$ are each independently selected from one or more of the group consisting of hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl; $R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus; the heterocyclyl is a 3-12 membered heterocyclic ring containing one or more of N and O atoms; m is selected from any integer from 0 to 3; p is selected from any integer from 0 to 6; and n is 1 or 2.

Preferably, when n is 1, the inhibitor is a compound having the following general structural formula (Ia) or a pharmaceutically acceptable salt thereof:

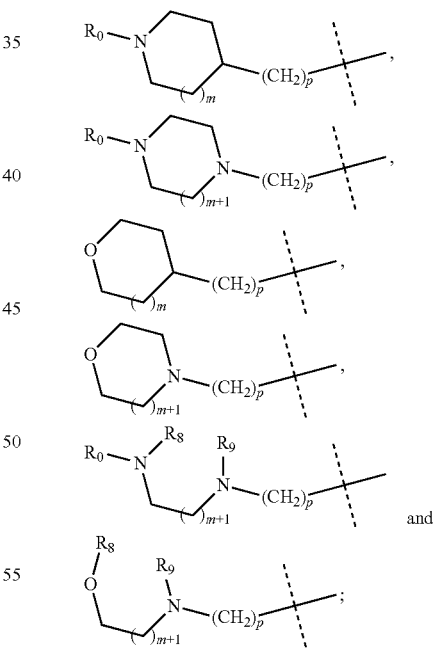

wherein $R_1$ is selected from

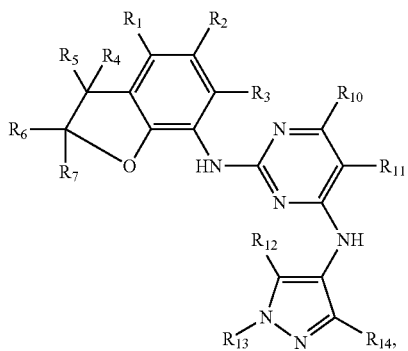

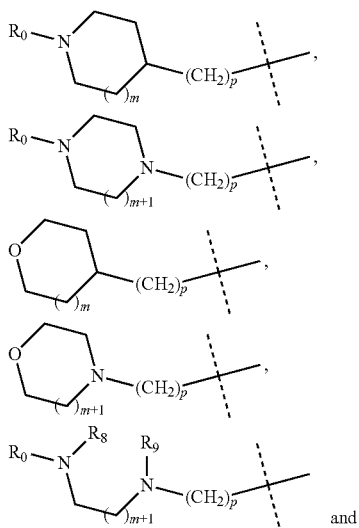

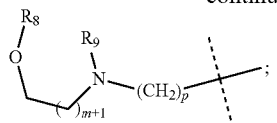

$R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl; $R_2$, $R_3$, $R_4$, $R_5$, $R_6$, $R_7$, $R_{10}$ and $R_{11}$ are each independently selected from the group consisting of hydrogen, halogen, $C_{1-6}$ alkyl, halogenated $C_{1-6}$ alkyl, $C_{1-6}$ alkoxy, halogenated $C_{1-6}$ alkoxy, cyano or amino; $R_{13}$ is selected from one or more of the group consisting of hydrogen, $C_{1-6}$ alkoxy, $C_{1-6}$ alkyl, $C_{3-6}$ cycloalkyl, amido, boryl, amino, hydroxyl, cyano, carbonyl, carboxy, aryl and heterocyclyl; $R_{12}$ and $R_{14}$ are each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl; $R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus; the heterocyclyl is a 3-6 membered heterocyclic ring containing one or more of N and O atoms; m is selected from any integer from 0 to 3; and p is selected from any integer from 0 to 6.

More preferably, in the general structural formula (Ia), $R_1$ is selected from $R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl; $R_2$ and $R_3$ are simultaneously hydrogen, or one of $R_2$ and $R_3$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino; $R_4$ and $R_5$ are simultaneously hydrogen, or one of $R_4$ and $R_5$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino, and $R_4$ and/or $R_5$ constitute(s) R form, S form or enantiomer; $R_6$ and $R_7$ are simultaneously hydrogen, or one of $R_6$ and $R_7$ is hydrogen and the other group is halogen, $C_{1-6}$ alkyl, halogenated $C_{1-6}$ alkyl, $C_{1-6}$ alkoxy, halogenated $C_{1-6}$ alkoxy, and $R_6$ and/or $R_7$ constitute(s) R form, S form or enantiomer; $R_{10}$ and $R_{11}$ are simultaneously hydrogen, or one of $R_{10}$ and $R_{11}$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino; $R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus; $R_{13}$ is selected from the group consisting of hydrogen, $C_{1-6}$ alkoxy, $C_{1-6}$ alkyl, $C_{3-6}$ cycloalkyl, amido, amino-containing $C_{1-6}$ alkyl, $C_{1-6}$ alkylcarbonyl, aryl or heterocyclyl; $R_{12}$ and $R_{14}$ are each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl; the heterocyclyl is a 3-6 membered heterocyclic ring containing one or more of N and O atoms; m is selected from any integer from 0 to 3; and p is selected from any integer from 0 to 6.

Preferably, when n is 2, the inhibitor is a compound having the following general structural formula (Ib) or a pharmaceutically acceptable salt thereof:

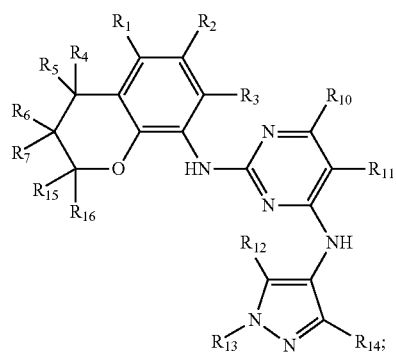

(Ib)

wherein $R_1$ is selected from

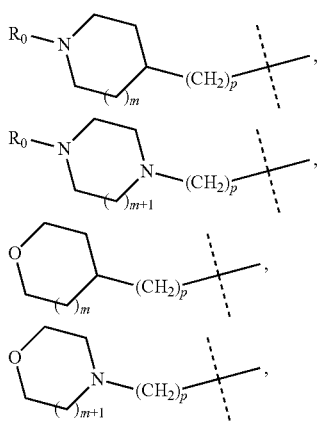

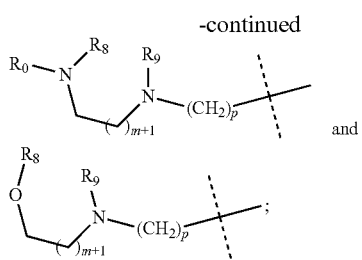

and $R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl; $R_2$, $R_3$, $R_4$, $R_5$, $R_6$, $R_7$, $R_{10}$, $R_{11}$, $R_{15}$ and $R_{16}$ are each independently selected from the group consisting of hydrogen, halogen, $C_{1-6}$ alkyl, halogenated $C_{1-6}$ alkyl, $C_{1-6}$ alkoxy, halogenated $C_{1-6}$ alkoxy, cyano or amino; $R_{13}$ is selected from one or more of the group consisting of hydrogen, $C_{1-6}$ alkoxy, $C_{1-6}$ alkyl, $C_{3-6}$ cycloalkyl, amido, boryl, amino, hydroxyl, cyano, carbonyl, carboxy, aryl and heterocyclyl; $R_{12}$ and $R_{14}$ are each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl; $R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus; the heterocyclyl is a 3-6 membered heterocyclic ring containing one or more of N and O atoms; m is selected from any integer from 0 to 3; and p is selected from any integer from 0 to 6.

More preferably, in the general structural formula (Ib), $R_1$ is selected from

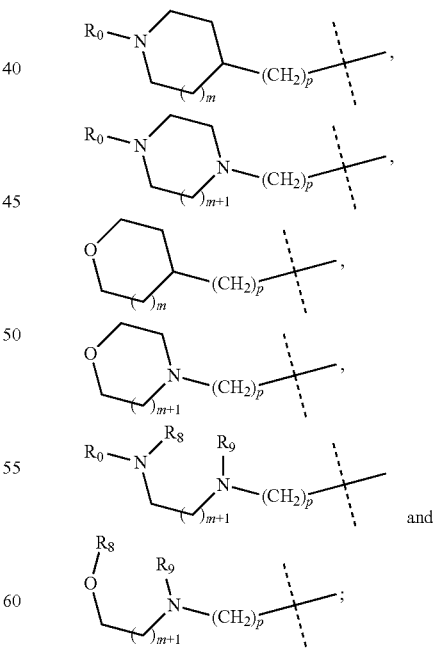

$R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl; $R_2$ and $R_3$ are simultaneously hydrogen, or one of $R_2$ and $R_3$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino; $R_4$ and $R_5$ are simultaneously hydrogen, or one of $R_4$ and $R_5$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino, and $R_4$ and/or $R_5$ constitute(s) R form, S form or enantiomer; $R_6$ and $R_7$ are simultaneously hydrogen, or one of $R_6$ and $R_7$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino; $R_6$ and/or $R_7$ constitute(s) R form, S form or enantiomer; $R_{15}$ and $R_{16}$ are simultaneously hydrogen, or one of $R_{15}$ and $R_{16}$ is hydrogen and the other is halogen, $C_{1-6}$ alkyl, halogenated $C_{1-6}$ alkyl, $C_{1-6}$ alkoxy, halogenated $C_{1-6}$ alkoxy, and $R_{15}$ and/or $R_{16}$ constitute(s) R form, S form or enantiomer; $R_{10}$ and $R_{11}$ are simultaneously hydrogen, or one of $R_{10}$ and $R_{11}$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino; $R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus; $R_{13}$ is selected from the group consisting of hydrogen, $C_{1-6}$ alkoxy, $C_{1-6}$ alkyl, $C_{3-6}$ cycloalkyl, amido, amino-containing $C_{1-6}$ alkyl, $C_{1-6}$ alkylcarbonyl, aryl or heterocyclyl; $R_{12}$ and $R_{14}$ are each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl; the heterocyclyl is a 3-6 membered heterocyclic ring containing one ore more of N and O atoms; m is selected from any integer from 0 to 3; and p is selected from any integer from 0 to 6.

Preferably, the benzofuran pyrazole amine protein kinase inhibitor is a compound having the following general structural formula (Ic) or a pharmaceutically acceptable salt thereof:

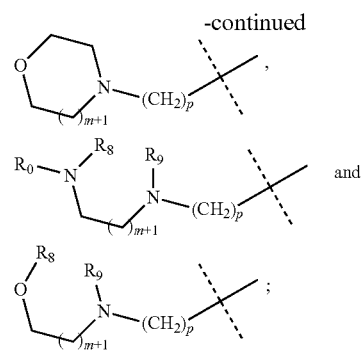

(Ic)

wherein $R_1$ is selected from

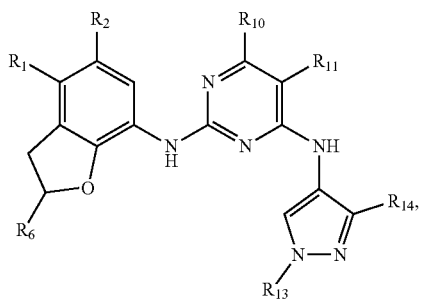

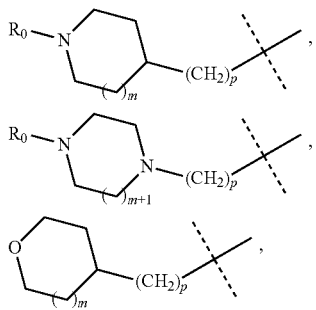

$R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl; $R_2$ is hydrogen, halogen, $C_{1-6}$ alkyl, halogenated $C_{1-6}$ alkyl, $C_{1-6}$ alkoxy, halogenated $C_{1-6}$ alkoxy, cyano or amino; $R_6$ is hydrogen, halogen, $C_{1-6}$ alkyl, halogenated $C_{1-6}$ alkyl, $C_{1-6}$ alkoxy, halogenated $C_{1-6}$ alkoxy, and $R_6$ constitutes R form, S form or enantiomer; $R_{10}$ and $R_{11}$ are simultaneously hydrogen, or one of $R_{10}$ and $R_{11}$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino; $R_{13}$ is selected from the group consisting of hydrogen, $C_{1-6}$ alkoxy, $C_{1-6}$ alkyl, $C_{3-6}$ cycloalkyl, amido, amino-containing $C_{1-6}$ alkyl, $C_{1-6}$ alkylcarbonyl, aryl or heterocyclyl; $R_{14}$ is each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl; the heterocyclyl is a 3-6 membered heterocyclic ring containing one or more of N and O atoms; m is selected from any integer from 0 to 3; and p is selected from any integer from 0 to 6.

Preferably, in the above general structural formulas (I), (Ia), (Ic) and (Ib), the aryl is phenyl, naphthyl or anthryl; the heterocyclyl is morpholinyl, piperidyl, pyranyl, pyrazolyl, furyl, pyridyl or pyrimidinyl; and the halogen is selected from one or more of the group consisting of fluorine, chlorine, bromine and iodine.

A benzofuran pyrazole amine protein kinase inhibitor is selected from the following compounds with identification numbers of REX-D1 to REX-D41:

REX-D1: (R)-5-chloro-$N^2$-(2,5-dimethyl-4-(piperidin-4-yl)-2,3-dihydrobenzofuran-7-yl)-$N^4$-(3-(isopropylsulfonyl)-1-methyl-1H-pyrazol-4-yl)pyrimidine-2,4-diamine;

REX-D2: (R)-5-chloro-$N^2$-(2,5-dimethyl-4-(1-methylpiperidin-4-yl)-2,3-dihydrobenzofuran-7-yl)-$N^4$-(3-(isopropylsulfonyl)-1-methyl-1H-pyrazol-4-yl)pyrimidine-2,4-diamine;

REX-D3: (R)—$N^2$-(2,5-dimethyl-4-(piperidin-4-yl)-2,3-dihydrobenzofuran-7-yl)-$N^4$-(3-(isopropylsulfonyl)-1-methyl-1H-pyrazol-4-yl)-5-(trifluoromethyl)pyrimidine-2,4-diamine;

REX-D4: (R)—$N^2$-(2,5-dimethyl-4-(1-methylpiperidin-4-yl)-2,3-dihydrobenzofuran-7-yl)-$N^4$-(3-(isopropylsulfonyl)-1-methyl-1H-pyrazol-4-yl)-5-(trifluoromethyl)pyrimidine-2,4-diamine;

REX-D5: (R)-2-(4-(7-((4-((3-(isopropylsulfonyl)-1-methyl-1H-pyrazol-4-yl)amino)-5-(trifluoromethyl)pyrimidin-2-yl)amino)-2,5-dimethyl-2,3-dihydrobenzofuran-4-yl)piperidin-1-yl)ethanol;

REX-D6: N²-(2,6-dimethyl-5-(1-methylpiperidin-4-yl)chroman-8-yl)-N⁴-(3-(isopropylsulfonyl)-1-methyl-1H-pyrazol-4-yl)-5-(trifluoromethyl)pyrimidine-2,4-diamine;

REX-D7: (R)—N⁴-(3-(isopropylsulfonyl)-1-methyl-1H-pyrazol-4-yl)-N²-(2-methyl-4-(1-methylpiperidin-4-yl)-2,3-dihydrobenzofuran-7-yl)-5-(trifluoromethyl)pyrimidine-2,4-diamine;

REX-D8: (R)—N²-(5-fluoro-2-methyl-4-(1-methylpiperidin-4-yl)-2,3-dihydrobenzofuran-7-yl)-N⁴-(3-(isopropylsulfonyl)-1-methyl-1H-pyrazol-4-yl)-5-(trifluoromethyl)pyrimidine-2,4-diamine;

REX-D9: (R)—N⁴-(1-cyclopropyl-3-(isopropylsulfonyl)-1H-pyrazol-4-yl)-N²-(2,5-dimethyl-4-(1-methylpiperidin-4-yl)-2,3-dihydrobenzofuran-7-yl)-5-(trifluoromethyl)pyrimidine-2,4-diamine;

REX-D10: (R)—N²-(2,5-dimethyl-4-(1-methylpiperidin-4-yl)-2,3-dihydrobenzofuran-7-yl)-N⁴-(3-(isobutylsulfonyl)-1-methyl-1H-pyrazol-4-yl)-5-(trifluoromethyl)pyrimidine-2,4-diamine;

REX-D11: (R)-2-(4-(7-((5-chloro-4-((3-(isopropylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanol;

REX-D12: (R)-1-(4-(7-((5-chloro-4-((3-(isopropylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanone;

REX-D13: (R)—N²-(4-([1,4'-bipiperidin]-4-yl)-2,5-dimethyl-2,3-dihydrobenzofuran-7-yl)-5-chloro-N⁴-(3-(isopropylsulfonyl)-1-methyl-1H-pyrazol-4-yl)pyrimidine-2,4-diamine;

REX-D14: (R)-5-chloro-N²-(4-(1-isopropylpiperidin-4-yl)-2,5-dimethyl-2,3-dihydrobenzofuran-7-yl)-N⁴-(3-(isopropylsulfonyl)-1-methyl-1H-pyrazol-4-yl)pyrimidine-2,4-diamine;

REX-D15: (R)-5-chloro-N²-(4-(4-(isopropylamino)cyclohexyl)-2,5-dimethyl-2,3-dihydrobenzofuran-7-yl)-N⁴-(3-(isopropylsulfonyl)-1-methyl-1H-pyrazol-4-yl)pyrimidine-2,4-diamine;

REX-D16: 5-chloro-N²-((2R)-2,5-dimethyl-4-(piperidin-3-yl)-2,3-dihydrobenzofuran-7-yl)-N⁴-(3-(isopropylsulfonyl)-1-methyl-1H-pyrazol-4-yl)pyrimidine-2,4-diamine;

REX-D17: 5-chloro-N²-((2R)-2,5-dimethyl-4-(1-methylpiperidin-3-yl)-2,3-dihydrobenzofuran-7-yl)-N⁴-(3-(isopropylsulfonyl)-1-methyl-1H-pyrazol-4-yl)pyrimidine-2,4-diamine;

REX-D18: 5-chloro-N²-((2R)-2,5-dimethyl-4-(pyrrolidin-3-yl)-2,3-dihydrobenzofuran-7-yl)-N⁴-(3-(isopropylsulfonyl)-1-methyl-1H-pyrazol-4-yl)pyrimidine-2,4-diamine;

REX-D19: 5-chloro-N²-((2R)-2,5-dimethyl-4-(1-methylpyrrolidin-3-yl)-2,3-dihydrobenzofuran-7-yl)-N⁴-(3-(isopropylsulfonyl)-1-methyl-1H-pyrazol-4-yl)pyrimidine-2,4-diamine;

REX-D20: (R)-5-chloro-N⁴-(3-(isopropylsulfonyl)-1-methyl-1H-pyrazol-4-yl)-N²-(2-methyl-4-(piperidin-4-yl)-2,3-dihydrobenzofuran-7-yl)pyrimidine-2,4-diamine;

REX-D21: (R)-5-chloro-N²-(5-fluoro-2-methyl-4-(piperidin-4-yl)-2,3-dihydrobenzofuran-7-yl)-N⁴-(3-(isopropylsulfonyl)-1-methyl-1H-pyrazol-4-yl)pyrimidine-2,4-diamine;

REX-D22: 5-chloro-N²-(2,6-dimethyl-5-(piperidin-4-yl)chroman-8-yl)-N⁴-(3-(isopropylsulfonyl)-1-methyl-1H-pyrazol-4-yl)pyrimidine-2,4-diamine;

REX-D23: (R)-5-chloro-N⁴-(3-(isopropylsulfonyl)-1-methyl-1H-pyrazol-4-yl)-N²-(2-methyl-4-(1-methylpiperidin-4-yl)-2,3-dihydrobenzofuran-7-yl)pyrimidine-2,4-diamine;

REX-D24: (R)-5-chloro-N²-(5-fluoro-2-methyl-4-(1-methylpiperidin-4-yl)-2,3-dihydrobenzofuran-7-yl)-N⁴-(3-(isopropylsulfonyl)-1-methyl-1H-pyrazol-4-yl)pyrimidine-2,4-diamine;

REX-D25: 5-chloro-N²-(2,6-dimethyl-5-(1-methylpiperidin-4-yl)chroman-8-yl)-N⁴-(3-(isopropylsulfonyl)-1-methyl-1H-pyrazol-4-yl)pyrimidine-2,4-diamine;

REX-D26: (S)-5-chloro-N⁴-(3-(isopropylsulfonyl)-1-methyl-1H-pyrazol-4-yl)-N²-(2-methyl-4-(piperidin-4-yl)-2,3-dihydrobenzofuran-7-yl)pyrimidine-2,4-diamine;

REX-D27: (S)-5-chloro-N⁴-(3-(isopropylsulfonyl)-1-methyl-1H-pyrazol-4-yl)-N²-(2-methyl-4-(1-methylpiperidin-4-yl)-2,3-dihydrobenzofuran-7-yl)pyrimidine-2,4-diamine;

REX-D28: 5-chloro-N⁴-(3-(isopropylsulfonyl)-1-methyl-1H-pyrazol-4-yl)-N²-(7-(1-methylpiperidin-4-yl)-1,3-dihydroisobenzofuran-4-yl)pyrimidine-2,4-diamine;

REX-D29: (R)—N²-(2,5-dimethyl-4-(piperidin-4-yl)-2,3-dihydrobenzofuran-7-yl)-N⁴-(3-(isopropylsulfonyl)-1-methyl-1H-pyrazol-4-yl)thieno[3,2-d]pyrimidine-2,4-diamine;

REX-D30: (R)—N²-(2,5-dimethyl-4-(1-methylpiperidin-4-yl)-2,3-dihydrobenzofuran-7-yl)-N⁴-(3-(isopropylsulfonyl)-1-methyl-1H-pyrazol-4-yl)thieno[3,2-d]pyrimidine-2,4-diamine;

REX-D31: (R)-5-chloro-N⁴-(1-cyclopropyl-3-(isopropylsulfonyl)-1H-pyrazol-4-yl)-N²-(2,5-dimethyl-4-(piperidin-4-yl)-2,3-dihydrobenzofuran-7-yl)pyrimidine-2,4-diamine;

REX-D32: (R)-5-chloro-N²-(2,5-dimethyl-4-(piperidin-4-yl)-2,3-dihydrobenzofuran-7-yl)-N⁴-(1-isopropyl-3-(isopropylsulfonyl)-1H-pyrazol-4-yl)pyrimidine-2,4-diamine;

REX-D33: (R)-5-chloro-N²-(2,5-dimethyl-4-(piperidin-4-yl)-2,3-dihydrobenzofuran-7-yl)-N⁴-(1-ethyl-3-(isopropylsulfonyl)-1H-pyrazol-4-yl)pyrimidine-2,4-diamine;

REX-D34: (R)-5-chloro-N⁴-(1-cyclopropyl-3-(isopropylsulfonyl)-1H-pyrazol-4-yl)-N²-(2,5-dimethyl-4-(1-methylpiperidin-4-yl)-2,3-dihydrobenzofuran-7-yl)pyrimidine-2,4-diamine;

REX-D35: (R)-5-chloro-N²-(2,5-dimethyl-4-(1-methylpiperidin-4-yl)-2,3-dihydrobenzofuran-7-yl)-N⁴-(1-isopropyl-3-(isopropylsulfonyl)-1H-pyrazol-4-yl)pyrimidine-2,4-diamine;

REX-D36: (R)-5-chloro-N²-(2,5-dimethyl-4-(1-methylpiperidin-4-yl)-2,3-dihydrobenzofuran-7-yl)-N⁴-(1-ethyl-3-(isopropylsulfonyl)-1H-pyrazol-4-yl)pyrimidine-2,4-diamine;

REX-D37: (R)-5-chloro-N²-(2,5-dimethyl-4-(piperidin-4-yl)-2,3-dihydrobenzofuran-7-yl)-N⁴-(3-(isobutylsulfonyl)-1-methyl-1H-pyrazol-4-yl)pyrimidine-2,4-diamine;

REX-D38: (R)-5-chloro-N²-(2,5-dimethyl-4-(1-methylpiperidin-4-yl)-2,3-dihydrobenzofuran-7-yl)-N⁴-(3-(isobutylsulfonyl)-1-methyl-1H-pyrazol-4-yl)pyrimidine-2,4-diamine;

REX-D39: (R)-2-(4-(7-((5-chloro-4-((3-(isobutylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanol;

REX-D40: (R)-5-chloro-N⁴-(1-cyclopropyl-3-(isobutylsulfonyl)-1H-pyrazol-4-yl)-N²-(2,5-dimethyl-4-(piperidin-4-yl)-2,3-dihydrobenzofuran-7-yl)pyrimidine-2,4-diamine;

REX-D41: (R)-5-chloro-N⁴-(1-cyclopropyl-3-(isobutylsulfonyl)-1H-pyrazol-4-yl)-N²-(2,5-dimethyl-4-(1-methylpiperidin-4-yl)-2,3-dihydrobenzofuran-7-yl)pyrimidine-2,4-diamine.

The specific structures of the above compounds with identification numbers of REX-D1 to REX-D41 are as follows:
REX-D1
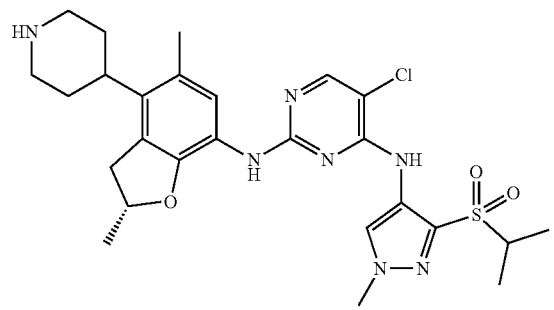
REX-D2
REX-D3
REX-D4
REX-D5
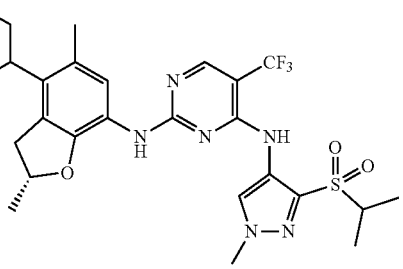
REX-D6
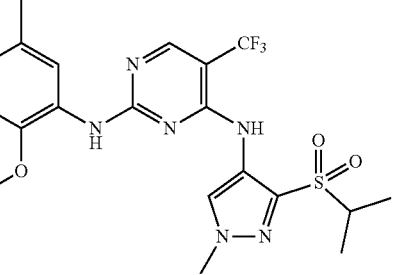
REX-D7
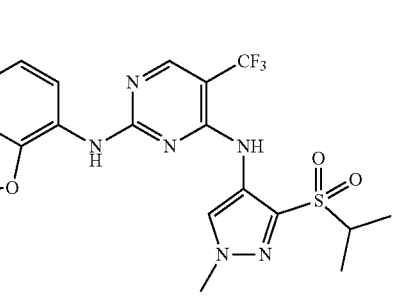
REX-D8
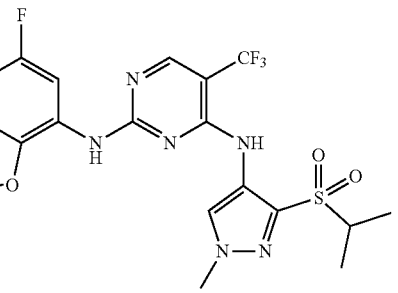

REX-D9
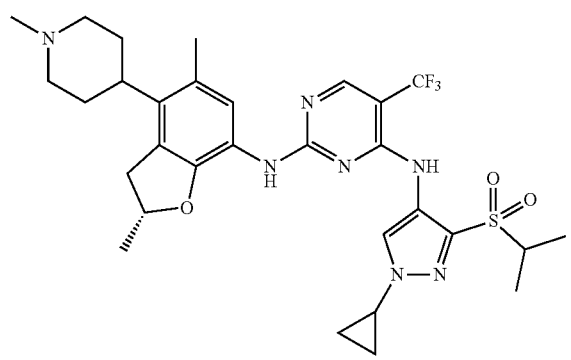
REX-D13
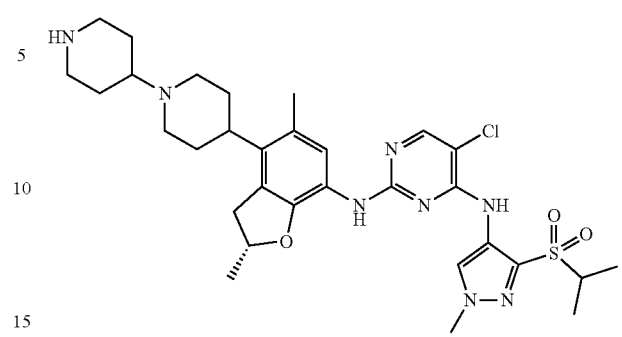
REX-D10
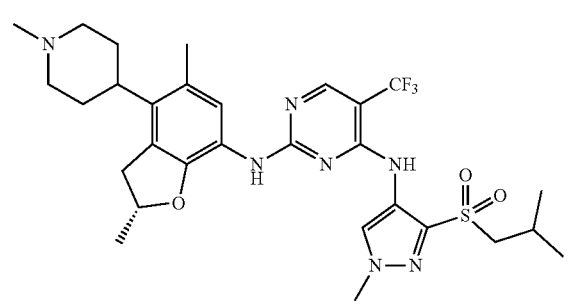
REX-D14
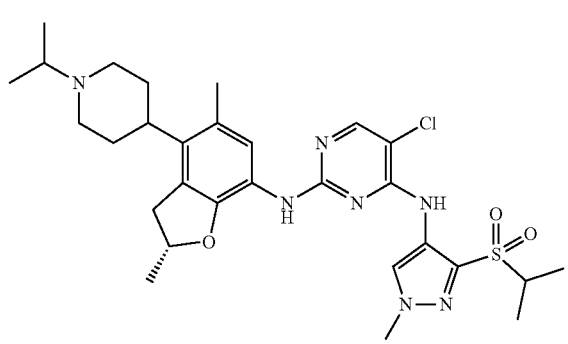
REX-D11
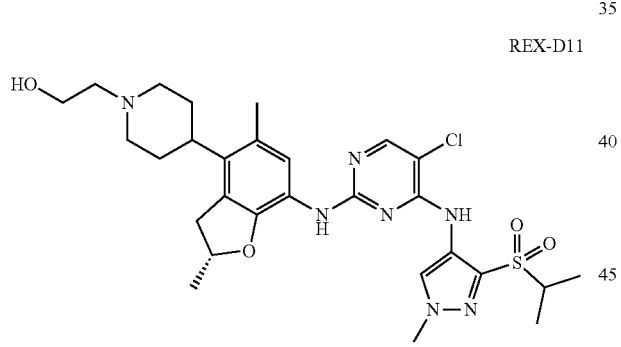
REX-D15
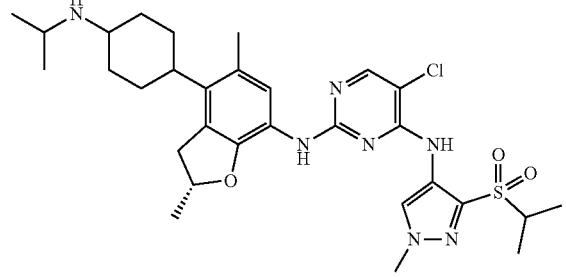
REX-D12
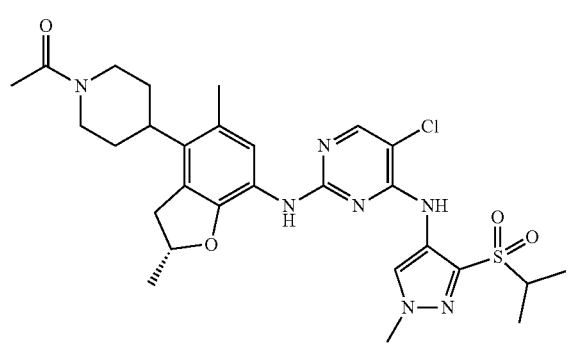
REX-D16
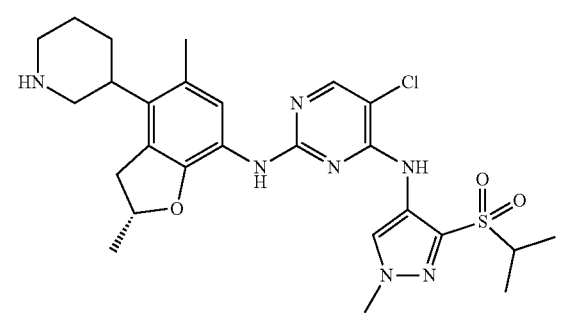

REX-D17
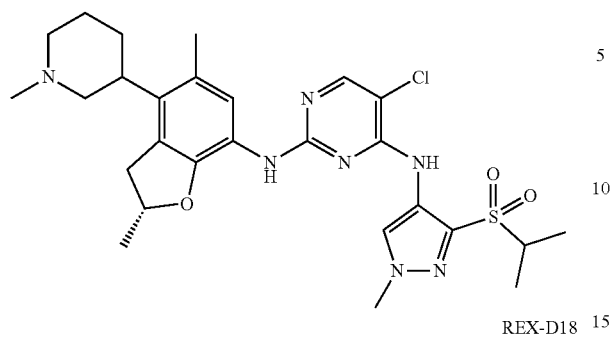
REX-D22
REX-D18
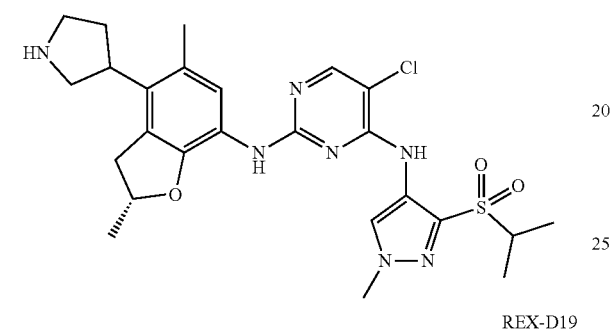
REX-D19
REX-D23
REX-D20
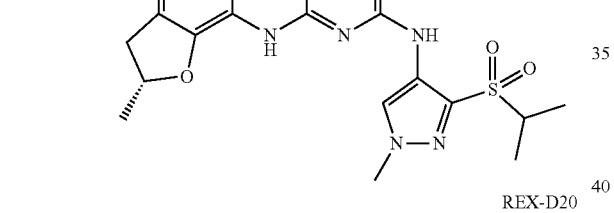
REX-D24
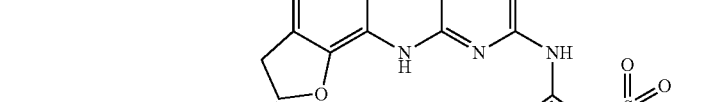
REX-D21
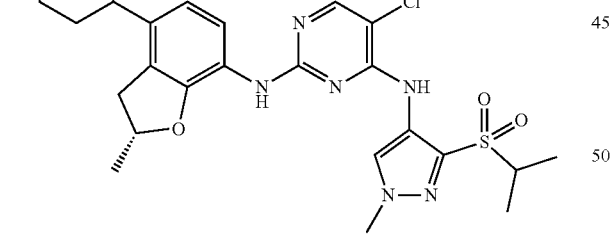
REX-D25
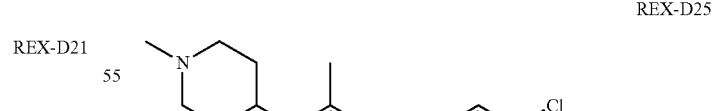
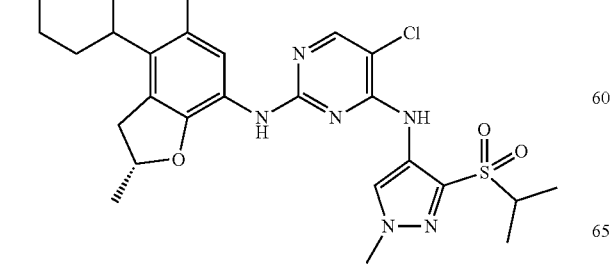

-continued
REX-D26
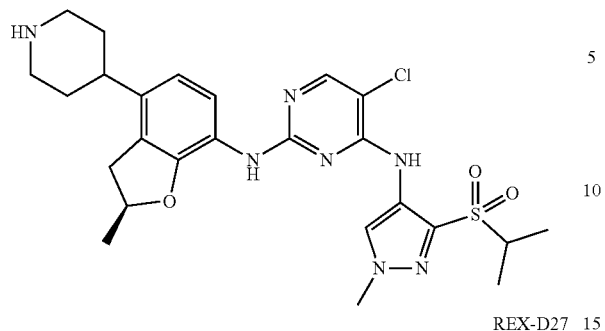
REX-D27
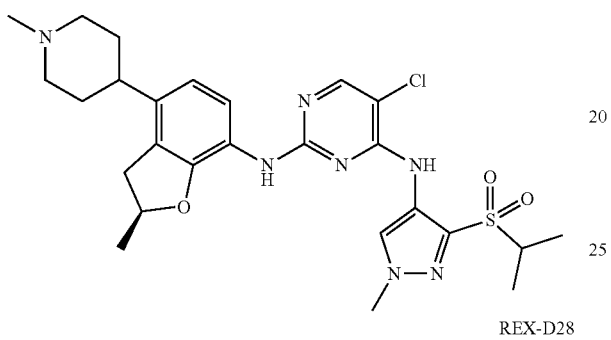
REX-D28
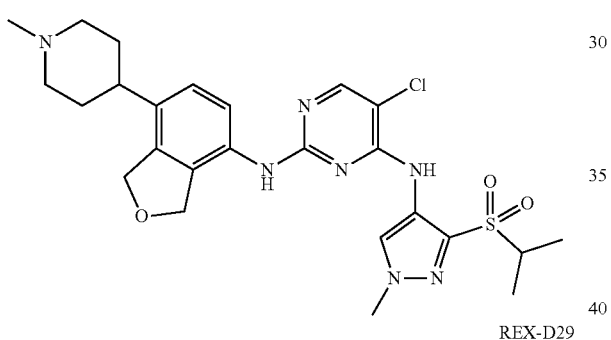
REX-D29
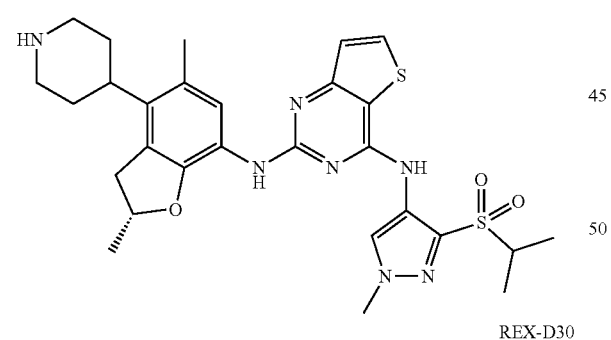
REX-D30
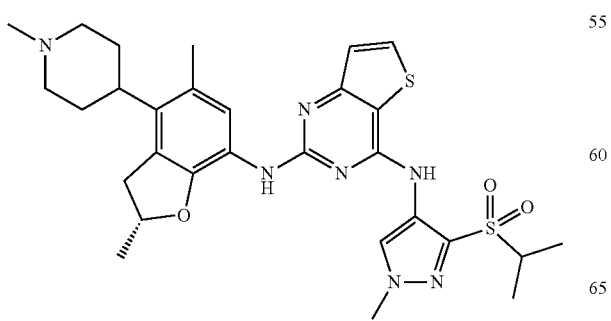
-continued
REX-D31
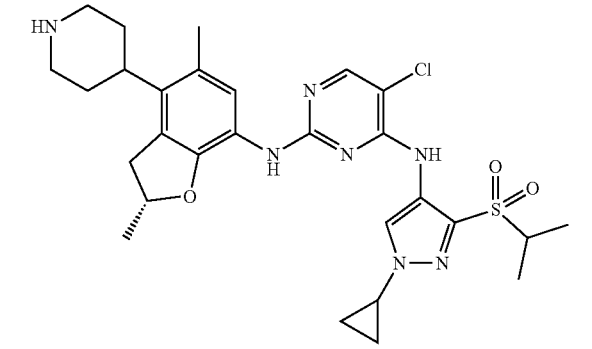
REX-D32
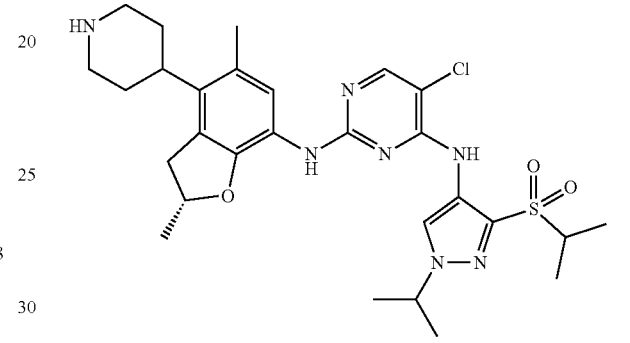
REX-D33
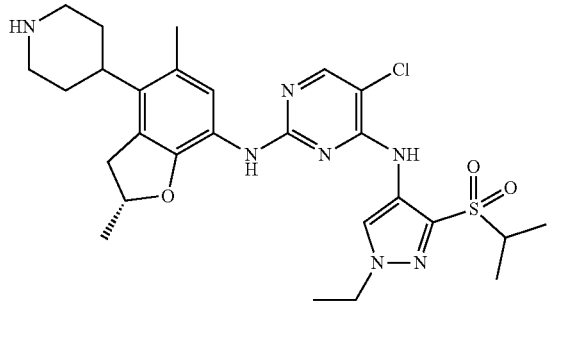
REX-D34
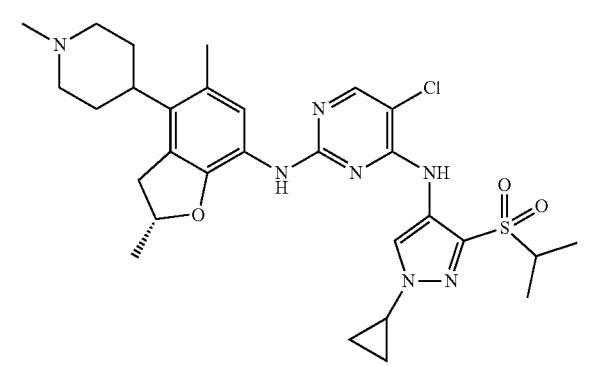

REX-D35
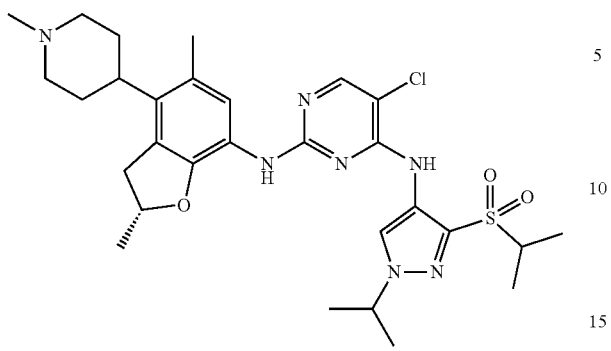
REX-D36
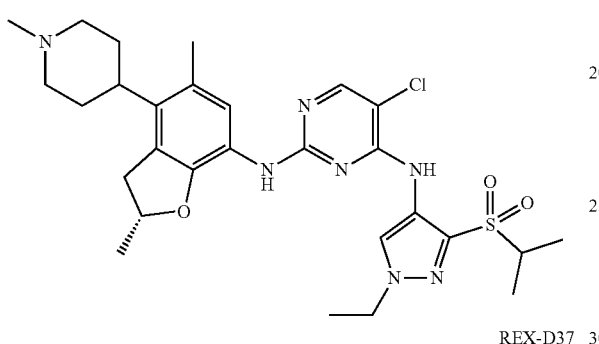
REX-D37
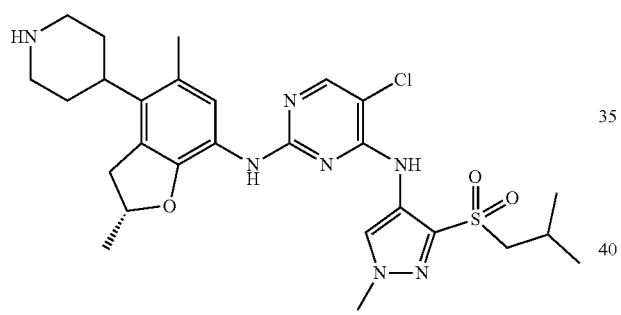
REX-D38
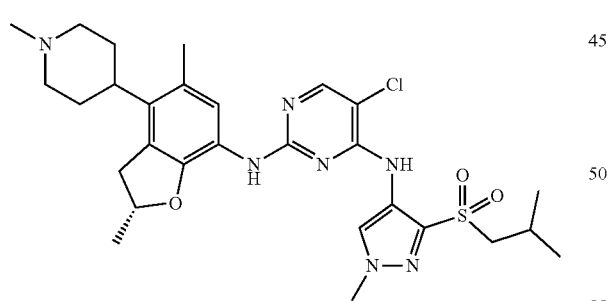
REX-D39
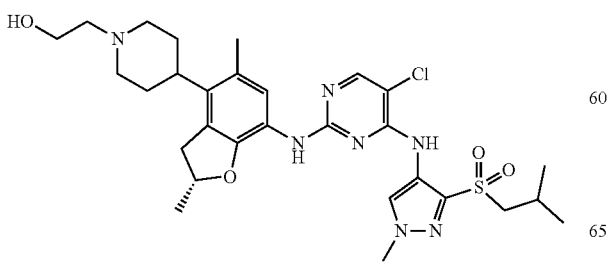
REX-D40
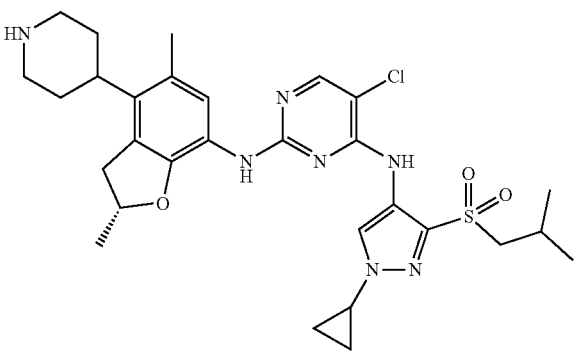
REX-D41
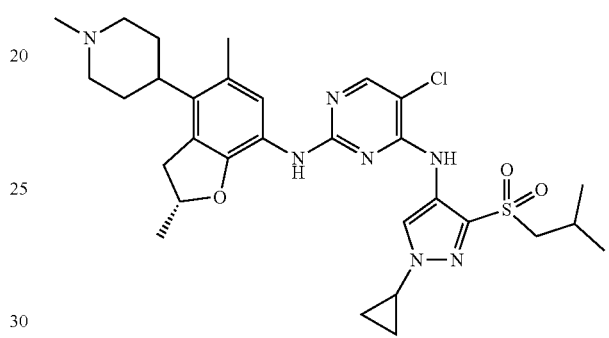
The present invention also provides a method of synthesizing the compound having the above general structural formula (I), and the total reaction route is as follows:
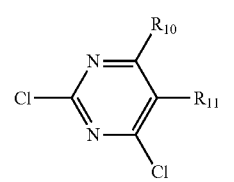
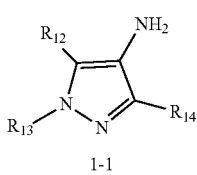
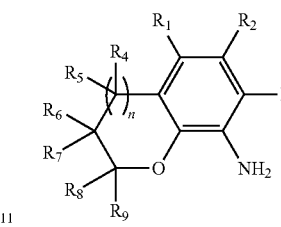
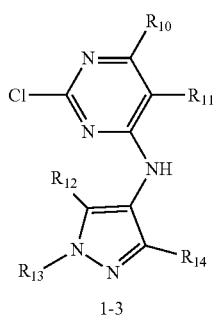

-continued

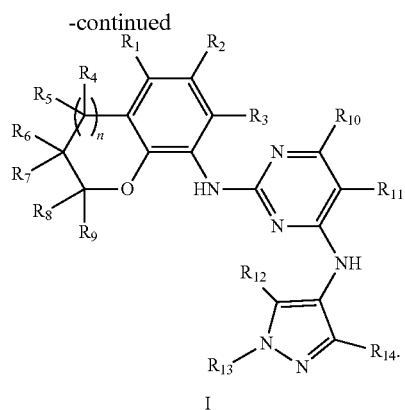

I

Based on the above total reaction route, the following synthetic method is included:

Step 1: To a solution of compound 1-1 in dry DMF was added DIPEA at 0° C., and then a solution of compound 1-2 was added into the solution under $N_2$. The solution was stirred at 100° C. for 14 h. The reaction was completed. The reaction was quenched with ice water. Then the extraction with EA was followed, and then the drying over anhydrous $Na_2SO_4$ and the rotary evaporation under reduced pressure were preformed to obtain compound 1-3.

Step 2: To a solution of compound 1-3, compound 1-4 in Dry dioxane were added $Cs_2CO_3$, $Pd(AcO)_2$ (20 mg) and Xantphos under $N_2$. The reaction was heated and stirred at Microwave for 30 minutes. After the reaction was completed, the filtration under reduced pressure was preformed. The residue was purified by column chromatography to obtain the target compound I.

In the above synthetic method, $R_1$ is selected from

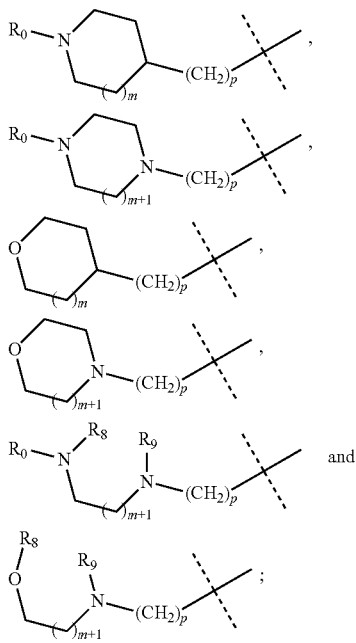

$R_0$, $R_8$ and $R_9$ are each independently selected from one or more of the group consisting of hydrogen, $C_{1-6}$ alkyl, $C_{2-6}$ alkenyl, $C_{2-6}$ alkynyl, acyl, amido, sulfo group, sulfanilamido, hydroxyl, aryl and heterocyclyl; $R_2$, $R_3$, $R_4$, $R_5$, $R_6$, $R_7$, $R_{10}$ and $R_{11}$ are each independently selected from the group consisting of hydrogen, halogen, $C_{1-6}$ alkyl, halogenated $C_{1-6}$ alkyl, $C_{1-6}$ alkoxy, halogenated $C_{1-6}$ alkoxy, $C_{2-6}$ alkenyl, $C_{2-6}$ alkynyl, cyano or amino; $R_{13}$ is selected from one or more of the group consisting of hydrogen, $C_{1-6}$ alkoxy, $C_{1-6}$ alkyl, $C_{3-6}$ cycloalkyl, $C_{2-6}$ alkenyl, $C_{2-6}$ alkynyl, amido, boryl, amino, hydroxyl, cyano, carbonyl, carboxy, aryl and heterocyclyl; $R_{12}$ and $R_{14}$ are each independently selected from one or more of the group consisting of hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl; $R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus; the heterocyclyl is a 3-12 membered heterocyclic ring containing one or more of N and O atoms; m is selected from any integer from 0 to 3; p is selected from any integer from 0 to 6; and n is 1 or 2.

The "compound" of the present invention comprises all stereoisomers, geometric isomers, tautomers and isotopes.

The "compound" of the present invention may be asymmetric, for example, having one or more stereoisomers. Unless otherwise indicated, all stereoisomers, such as enantiomers and diastereomers, are included. Compounds containing asymmetric carbon atoms in the present invention can be isolated in an optically active pure or racemic form. The optically pure form can be resolved from a racemic mixture or synthesized by using chiral starting materials or chiral reagents.

The "compound" of the present invention also includes tautomeric forms. Tautomeric forms result from the exchange between a single bond and an adjacent double bond which is accompanied by the migration of a proton.

The present invention also comprises all isotope atoms, whether in an intermediate or a final compound. Isotope atoms include those having the same atomic number but different mass number. For example, the isotopes of hydrogen include deuterium and tritium.

For compounds comprising the above general structural formulas, the terms used herein have the following meanings:

The term "halogen" refers to fluorine, chlorine, bromine or iodine, preferably fluorine, chlorine or bromine.

The term "cyano" refers to —CN.

The term "hydroxy" refers to —OH.

The term "alkyl" refers to a linear or branched saturated hydrocarbon group comprised of carbon atoms and hydrogen atoms, for example, $C_{1-20}$ alkyl, and preferably $C_{1-6}$ alkyl, such as methyl, ethyl, propyl (including n-propyl and isopropyl), butyl (including n-butyl, isobutyl, sec-butyl or t-butyl), pentyl (including n-pentyl, isopentyl and neopentyl), n-hexyl, 2-methylhexyl and the like. The alkyl group may be unsubstituted or substituted with one or more substituent(s) and the substituents include, but are not limited to, alkyl, alkoxy, cyano, hydroxyl, carbonyl, carboxyl, aryl, heteroaryl, amino, halogen, sulfonyl, sulfinyl and phosphoryl.

The term "amino" refers to —NH$_2$, —NH(alkyl), and —N(alkyl)$_2$, in which the meaning of alkyl is as previously provided. The structure of —NH(alkyl) is

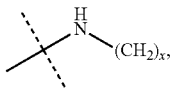

and specific examples thereof include, but are not limited to, —NHCH₃, —NHCH(CH₃)₂, —NHC₂H₅ and the like; and the structure of —N(alkyl)₂ is

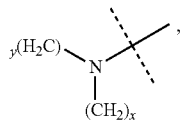

and specific examples thereof include, but are not limited to, —N(CH₃)₂, —N(CH₃)C₂H₅ and the like.

The term "aryl" refers to an all-carbon monocyclic or fused ring having a completely conjugated 2-electron system with generally 6-14 carbon atoms, preferably 6-12 carbon atoms, and most preferably 6 carbon atoms. The aryl may be unsubstituted or substituted with one or more substituent(s) including, but not limited to, alkyl, alkoxy, cyano, hydroxyl, carbonyl, carboxyl, aryl, aralkyl, amino, halogen, sulfonyl, sulfinyl and phosphoryl. Examples of unsubstituted aryl include, but are not limited to, phenyl, naphthyl and anthryl.

The term "heterocyclyl" refers to a monocyclic or fused ring having 3 to 12 (integer) ring atoms, wherein 1, 2 or 3 ring atom(s) is(are) selected from one or more of N and O, and the other ring atoms are C, and having a completely conjugated π-electron system. The heterocyclyl may be unsubstituted or substituted with one or more substituent(s) including, but not limited to, alkyl, alkoxy, cyano, hydroxyl, carbonyl, carboxyl, aryl, aralkyl, amino, halogen, sulfonyl, sulfinyl and phosphoryl. Examples of unsubstituted heterocyclyl include, but are not limited to, pyrrolyl, indolyl, pyrrolidinyl, imidazolyl, pyrazolyl, tetrazolyl, pyridyl, quinolyl, isoquinolyl, piperidyl, pyrimidyl, pyrazinyl, piperazinyl, furyl, pyranyl and morpholinyl.

The present invention also provides a pharmaceutical composition, comprising the compound or pharmaceutically acceptable salt thereof as described above as an active ingredient and one or more pharmaceutically acceptable carriers.

The "pharmaceutical composition" of the present invention refers to a formulation comprising one or more compound(s) of the present invention or a salt thereof, and carriers that is generally accepted for the delivery of biologically active compounds to an organism (such as human) in the art. The purpose of the pharmaceutical composition is to facilitate the drug delivery to the organism.

The term "pharmaceutically acceptable carrier" refers to a substance that is administered together with the active ingredient and beneficial to the administration of the active ingredient, including, but not limited to, any glidants, sweetening agents, diluents, preservatives, dyes/colorants, flavor enhancers, surfactants, wetting agents, dispersing agents, disintegrating agents, suspending agents, stabilizers, isotonic agents, solvents or emulsifiers which are licensed by the State Food and Drug Administration and acceptable for human or animal (such as livestock). Examples of the pharmaceutically acceptable carrier include, but are not limited to, calcium carbonate, calcium phosphate, various sugars and various types of starch, cellulose derivatives, gelatin, vegetable oil and polyethylene glycol.

The pharmaceutical composition of the present invention may be formulated into solid, semi-solid, liquid or gaseous formulations, such as tablets, pills, capsules, powders, granules, pastes, emulsions, suspensions, solutions, suppositories, injections, inhalants, gels, microspheres, aerosols and the like.

The pharmaceutical composition of the present invention may be manufactured by using the methods well known in the art, such as conventional mixing method, dissolution method, granulation method, dragee manufacture method, grinding method, emulsion method, lyophilization and the like.

The routes of administration of the compound, a pharmaceutically acceptable salt thereof or a pharmaceutical composition thereof of the present invention include, but are not limited to, oral, rectal, transmucosal and enteral administration, or topical, transdermal, inhalation, parenteral, sublingual, intravaginal, intranasal, intraocular, intraperitoneal, intramuscular, subcutaneous and intravenous administration. The preferred route of administration is oral administration.

For oral administration, the pharmaceutical composition can be formulated by mixing the active compounds with pharmaceutically acceptable carriers well-known in the art. These carriers enable the compounds of the present invention to be formulated as tablets, pills, lozenges, dragees, capsules, liquids, gels, syrups, suspending agents and the like, for oral administration to a patient. For example, the pharmaceutical composition for oral administration may be obtained as tablets by using the following method: combining the active ingredient with one or more solid carriers; and if necessary, granulating the resulting mixture, or if necessary, adding a small amount of excipients and processing into a mixture or granules to form a tablet or tablet core. The tablet core may be combined with optional coating materials suitable for enteric dissolution and processed into a coating formulation form that is more favourable for absorption by organisms (such as human).

The present invention also provides a use of the compound or pharmaceutically acceptable salt thereof as previously described in the preparation of the medication for treating or preventing diseases associated with protein kinases.

A use of the compound or pharmaceutically acceptable salt thereof as previously described in the preparation of the medication for treating or preventing diseases associated with anaplastic lymphoma kinase (ALK kinase) is provided.

Preferably, the disease associated with ALK kinase is selected from cellular proliferative diseases, and preferably tumor.

Preferably, the cellular proliferative diseases include non-small cell lung cancer, anaplastic large cell lymphoma, inflammatory myofibroblastic tumor, nasopharyngeal cancer, breast cancer, colorectal cancer, diffuse large B-cell lymphoma, liver cancer, gastric cancer, esophagus cancer, pancreatic cancer, ovarian cancer, systemic histiocytosis and neuroblastoma.

In the present invention, the inventors performed assays of ALK kinase inhibitory activity and the binding rate to ALK-related mutation sites for a series of synthetic benzofuran pyrazole amine compounds, and found that some of the compounds showed high inhibitory activity on ALK and good binding rate to ALK mutation sites (such as L1196M, G1202R). In addition, cell proliferation assays of various cancer cell strains, zebrafish phenotypic screening experiments and nude mice xenograft experiments were also performed, and it was found the some of the compounds have significant anti-tumor activity in vivo.

Compared with the prior art, the present invention obtains a series of compounds with a novel structure by the rational drug design of the target and the substitution modification of groups; and optimizes and screens a series of compounds with anti-tumor activity by the kinase activity experiments, cell proliferation assays, zebrafish phenotypic screening experiments and nude mice xenograft experiments. Based on that, the present invention provides the benzofuran pyrazole amine protein kinase inhibitor. Therefore, it can be used to develop a new generation of protein kinase inhibitor to solve the problem of the drug-resistance of the first generation and second generation ALK inhibitors, and has a great clinical application value for targeted therapy or the prevention of ALK-mediated diseases and thus has a considerable market potential.

EXAMPLES

Figure 1:
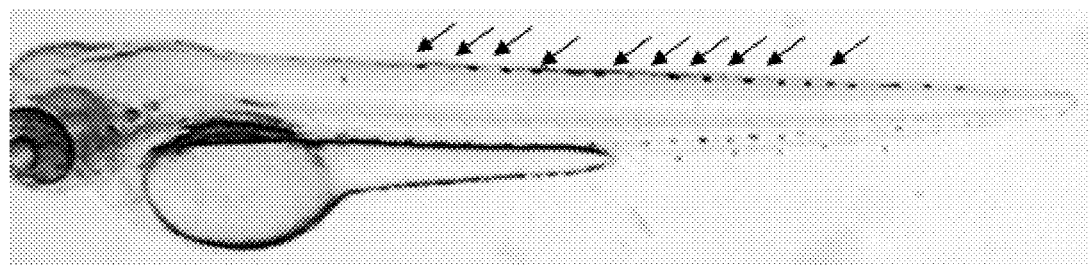
FIG. 1 shows the distribution of iridophores pigment cells in the spine of Albino zebrafish.

The following are specific embodiments of the present invention, and further describe the technical solutions of the present invention, but the scope of the present invention is not limited to these embodiments. All changes, equivalents and substitutions without departing from the concept of the present invention are included in the scope of protection of the present invention.

In the method for preparing the target compound provided by the present invention, a Waters Symmetry C18 column was used for liquid chromatography; a GF254 (0.25 mm) was used for thin layer chromatography (TLC); a Bruker-400 nuclear magnetic resonance instrument was used for Nuclear Magnetic Resonance Chromatography (NMR) assay; and the liquid chromatography (LC/MS) was performed using a Waters ZQ mass spectrometer detector (column: Waters Symmetry C18, mm, 5 micron, 35° C.) in ESI (+) ion mode.

In addition, all operations involving easily oxidizable materials or easily hydrolyzed materials are carried out under nitrogen protection. Unless otherwise specified, the starting materials used in the present invention are commercially available materials and can be used without further purification.

Example 1

(R)-5-chloro-$N^2$-(2,5-dimethyl-4-(piperidin-4-yl)-2,3-dihydrobenzofuran-7-yl)-$N^4$-(3-(isopropylsulfonyl)-1-methyl-1H-pyrazol-4-yl)pyrimidine-2,4-diamine [No. REX-D1]

Synthetic Routes:

Reaction 1

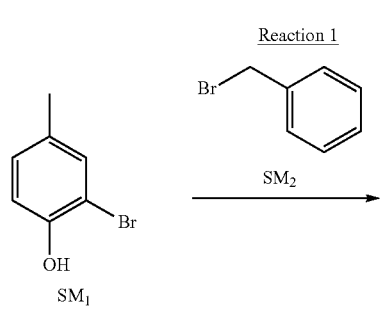

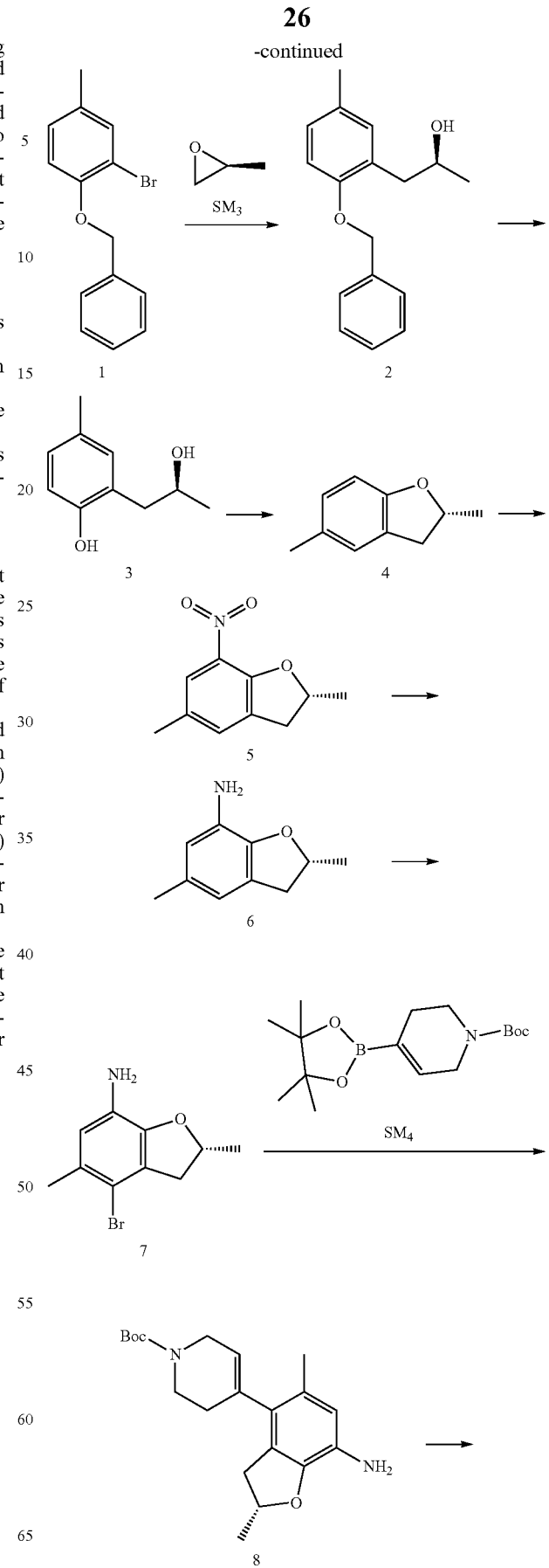

27
-continued

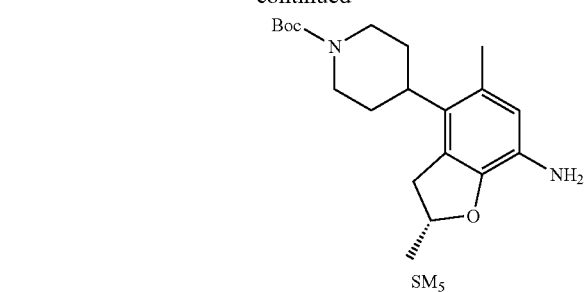

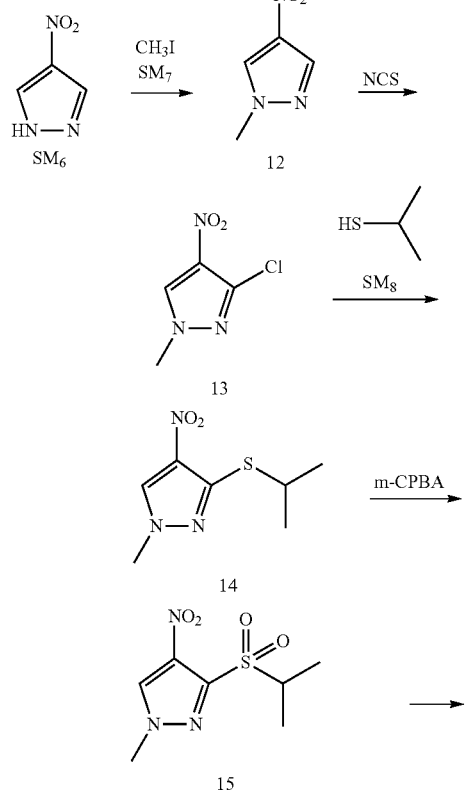

28
-continued
Reaction 3

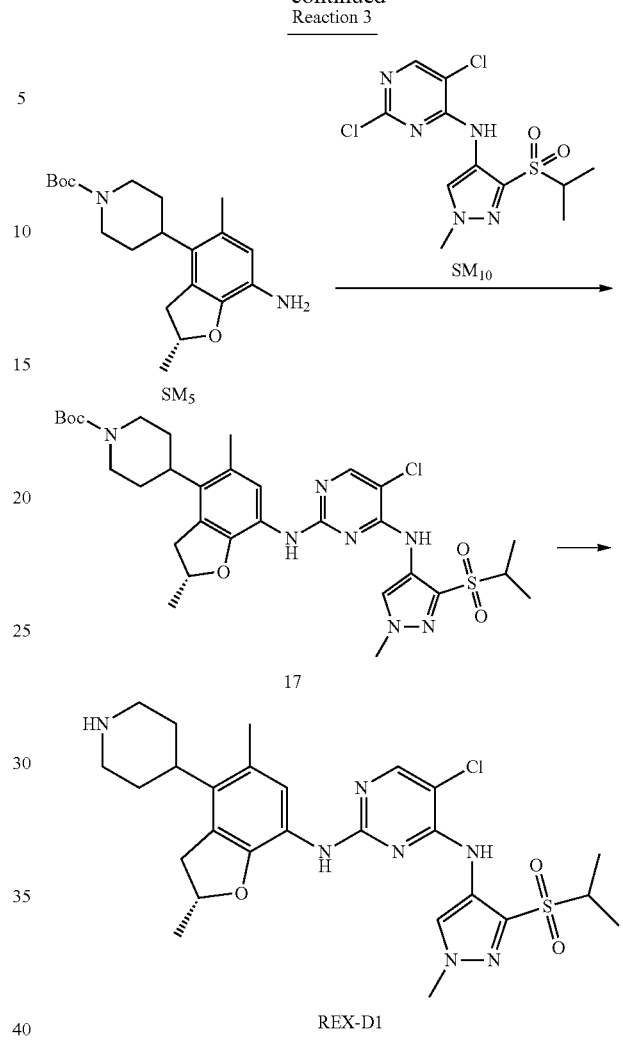

Reaction 1: The Preparation of the Compound SM5: (R)-tert-butyl-4-(7-amino-2,5-dimethyl-2,3-dihydrobenzofuran-4-yl)piperidine-1-carboxylate Step 1: The Preparation of 1-(benzyloxy)-2-bromo-4-methylbenzene (Compound 1)

To a solution of 2-bromo-4-methylphenol (SM1, 20 g, 0.107 mol) in acetone (240 ml) were added (bromomethyl)benzene (SM2, 15.2 ml, 21.95 g, 0.128 mol) and $K_2CO_3$ (44.3 g, 0.321 mol). The mixture was heated to reflux for 4 hours, and was cooled to room temperature. The solution was poured into water (400 ml) and extracted with EA. The organic layer was washed with water for two times, dried over anhydrous $Na_2SO_4$, filtered and concentrated under reduced pressure to obtain the crude product. The crude product was purified by column chromatography (PE:EA=98:2) to obtain the target compound 1 (23 g, 77.0% yield).

Step 2: The Preparation of (S)-1-(2-(benzyloxy)-5-methylphenyl)propan-2-ol (Compound 2)

To a solution of compound 1 (23 g, 0.083 mol) in dry THF (200 ml) under $N_2$ was added n-BuLi (2.5 M, 83 ml, 0.207 mol) at −65° C. After stirring at −55° C.~−65° C. for 2 h, (S)-2-methyloxirane (SM₃, 11.6 ml, 9.6 g, 0.166 mol) and BF₃Et₂O (20.5 ml, 23.6 g, 0.166 mol) were added and the reaction was stirred at −55° C.~−65° C. for 3 h. It was quenched with water (300 mL) and extracted with DCM. The organic layer was washed with aqueous NaCl, dried over anhydrous Na₂SO₄, filtered and evaporated. The residue was purified with column chromatography (PE:EA=98:2) to obtain the target compound 2 (9 g, 42.0% yield).
¹H-NMR (DMSO-d₆), δ: 1.009 (d, J=4 Hz, 3H), 2.208 (s, 3H), 2.545~2.750 (m, 2H), 3.835~3.946 (m, 1H), 4.475 (d, J=4.8 Hz, 1H), 5.064 (s, 2H), 6.857~6.985 (m, 3H), 7.290~7.473 (m, 5H).

Step 3: The Preparation of (S)-2-(2-hydroxypropyl)-4-methylphenol (Compound 3)

To a solution of compound 2 (12 g, 46.8 mmol) in MeOH (80 ml) was added Pd/C (33%, 2.4 g) at 0° C. for 15 min. The mixture was stirred under H2 at room temperature overnight, and then filtered. The filtrate was concentrated to obtain the target compound 3 (7.7 g, 99% yield).

Step 4: The Preparation of (R)-2,5-dimethyl-2,3-dihydrobenzofuran (Compound 4)

To a solution of compound 3 (7.78 g, 46.8 mmol) and PPh₃ (24.55 g, 93.6 mmol) in THF (300 ml) was added DEAD (14 ml, 16.3 g, 93.6 mmol). The mixture was stirred at 30° C. under N₂ for 4 h, It was quenched with water (300 mL) and extracted with DCM. The organic layer was washed with aqueous NaCl, dried over anhydrous Na₂SO₄, filtered and evaporated. The residue was purified with column chromatography to obtain the target compound 4 (4.3 g, 62% yield).
¹H-NMR (DMSO-d₆), δ: 1.350 (d, J=6.4 Hz, 3H), 2.207 (s, 3H), 2.665~2.748 (m, 1H), 3.194~3.281 (m, 1H), 4.788~4.888 (m, 1H), 6.586 (d, J=8 Hz, 1H), 6.855 (d, J=8 Hz, 1H), 6.972 (s, 1H).

Step 5: The Preparation of (R)-2,5-dimethyl-7-nitro-2,3-dihydrobenzofuran (Compound 5)

TFA (100 ml) was cooled to 0° C. and NaNO₂ (5.6 g, 80.97 mmol) was added in portions at 0° C. The mixture was stirred for 30 min at 0° C. A solution of compound 4 (10 g, 67.48 mmol) in TFA (30 ml) was added at 0° C. The reaction was stirred at the same temperature for 1 h and was warmed to room temperature. It was quenched with water (300 mL) and extracted with EA. The organic layer was washed with aqueous NaHCO₃, dried over anhydrous Na₂SO₄, filtered and evaporated. The residue was purified with column chromatography to obtain the target compound 5 (8.0 g, 61% yield).

Step 6: The Preparation of (R)-2,5-dimethyl-2,3-dihydrobenzofuran-7-amine (Compound 6)

To a solution of compound 5 (8 g, 41.4 mmol) in MeOH (80 ml) was added Pd/C (33%, 1.6 g) at 0° C. The mixture was stirred for 15 min at 0° C., and then stirred at room temperature under H₂ overnight and filtered. The filtrate was concentrated to obtain the target compound 6 (6.2 g, 92% yield).

Step 7: The Preparation of (R)-4-bromo-2,5-dimethyl-2,3-dihydrobenzofuran-7-amine (Compound 7)

To a solution of compound 6 (6.2 g, 37.99 mmol) in DMF (80 ml) was added NBS (6.76 g, 37.99 mmol) at 0° C. in portions. The mixture was stirred at 0° C. for 30 min, and then the organic layer was washed with aqueous NaHCO₃, dried over anhydrous Na₂SO₄, filtered and evaporated to obtain the target compound 7 (7 g, 76.1% yield).
¹H-NMR (DMSO-d₆), δ: 1.388 (d, J=6 Hz, 3H), 2.133 (s, 3H), 2.703 (q, J=8 Hz, 1H), 3.230 (q, J=8 Hz, 1H), 4.651 (s, 2H), 4.853~4.956 (m, 1H), 6.431 (s, 1H).

Step 8: The Preparation of (R)-tert-butyl-4-(7-amino-2,5-dimethyl-2,3-dihydrobenzofuran-4-yl)-5,6-dihydropyridine-1(2H)-carboxylate (Compound 8)

The mixture of compound 7 (100 mg, 0.413 mmol), tert-butyl-4-(4,4,5,5-tetramethyl-1,3,2-dioxaborolan-2-yl)-5,6-dihydropyridine-1(2H)-carboxylate (SM₄, 101.54 mg, 0.826 mmol), Cs₂CO₃ (336.44 mg, 1.033 mmol), Pd(PPh₃)₄ (47.7 mg, 0.0413 mmol) and H₂O (0.9 ml) in DMF (5 ml) was stirred at 135° C. for 1 h. Then the organic layer was washed with aqueous NaHCO₃, dried over anhydrous Na₂SO₄, filtered and evaporated. The residue was purified by column chromatography on silica gel to obtain the target compound 8 (80 mg, 80.6% yield).

Step 9: The Preparation of (R)-tert-butyl-4-(7-amino-2,5-dimethyl-2,3-dihydrobenzofuran-4-yl) piperidine-1-carboxylate (SM5)

To a solution of compound 8 (80 mg, 0.225 mmol) in MeOH (10 ml) was added Pd/C (33%, 300 mg) at 0° C. The mixture was stirred for 15 min at 0° C., and then stirred at room temperature under H₂ overnight and filtered. The filtrate was concentrated to obtain the target compound SM5 (56 mg, 63% yield).

Reaction 2: The Preparation of 2,5-dichloro-N-(3-(isopropylsulfonyl)-1-methyl-1H-pyrazol-4-yl)pyrimidin-4-amine Step 1: The Preparation of 1-methyl-4-nitro-1H-pyrazole (Compound 12)

The solution of 4-nitro-1H-pyrazole (SM₆, 10 g, 88.44 mmol), NaH (60%, 1.3 eq, 4.60 g, 114.97 mmol) and iodomethane (SM₇, 25 g, 177 mmol) in Dry DMF (100 ml) was stirred at 0° C. overnight, and then cooled to room temperature and quenched with water (200 mL) and extracted with EA. The organic layer was dried over anhydrous Na₂SO₄ to obtain the target compound 12(11 g, 92% yield).

Step 2: The Preparation of 3-chloro-1-methyl-4-nitro-1H-pyrazole (Compound 13)

The solution of compound 12 (11 g, 86.55 mmol) and NCS (1.2 eq, 13.87 g, 103.85 mmol) in dry THF (100 ml) was cooled to −78° C. under N₂. LiHMDS (1.5 eq, 26% in THF, 21.72 g, 129.82 mmol, 93.77 mL) was added dropwise into the solution while the inner temperature was maintained at −78° C. The reaction was stirred at same temperature for 2 h, and then warmed to room temperature and quenched with water (200 mL), extracted with EA, dried over anhydrous Na$_2$SO$_4$, filtered and evaporated. The residue was purified with column chromatography (PE:EA=20:1) to obtain the target compound 13 (7.0 g, 50% yield).

Step 3: The Preparation of 3-(isopropylthio)-1-methyl-4-nitro-1H-pyrazole (Compound 14)

The solution of compound 13 (7.0 g, 43.39 mmol), propane-2-thiol (SM$_8$, 3.97 g, 52.07 mmol) and K$_2$CO$_3$ (14.99 g, 108.48 mmol) in dry DMF (30 mL) under N$_2$ was stirred at 100° C. for 14 h. Then the solution was cooled to room temperature and quenched with water (100 mL), extracted with EA, dried over anhydrous Na$_2$SO$_4$, filtered and evaporated. The residue was purified with column chromatography (PE:EA=10:1) to obtain the target compound 14 (7.00 g, 80.3% yield).

Step 4: The Preparation of 3-(isopropylsulfonyl)-1-methyl-4-nitro-1H-pyrazole (Compound 15)

To a solution of compound 14 (7.00 g, 34.78 mmol) in DCM (50 mL), m-CPBA (15.01 g, 86.96 mol) was added into the solution. The reaction was stirred at room temperature for 14 h under N$_2$. The reaction was quenched with water (100 mL), extracted with DCM. The organic layer was dried over anhydrous Na$_2$SO$_4$, filtered and evaporated. The residue was purified with column chromatography (PE:EA=10:1) to obtain the target compound 15 (4.8 g, 60.3% yield).

Step 5: The Preparation of 3-(isopropylsulfonyl)-1-methyl-1H-pyrazol-4-amine (Compound 16)

To a solution of compound 15 (4.8 g, 20.58 mmol) in MeOH (50 ml) was added Pd/C (33%, 480 mg). The mixture was stirred at room temperature under H$_2$ for 14 h, and then filtered. The filtrate was concentrated to obtain the target compound 16 (3.8 g, 90.3% yield).

Step 6: The Preparation of 2,5-dichloro-N-(3-(isopropylsulfonyl)-1-methyl-1H-pyrazol-4-yl)pyrimidin-4-amine (SM10)

The solution of compound 16 (1.23 g, 6.05 mmol), DIPEA (3.13 g, 24.21 mmol) and 2,4,5-trichloropyrimidine (SM$_9$, 1.33 g, 7.26 mmol) in isopropanol (50 mL) under N$_2$ was stirred at 95° C. for 14 h. The reaction was quenched with water (100 mL), extracted with DCM. The organic layer was dried over anhydrous Na$_2$SO$_4$, filtered and evaporated. The residue was purified with column chromatography (PE:EA=2:1) to obtain the target compound SM$_{10}$ (0.8 g, 40.3% yield).

$^1$H-NMR (DMSO-d$_6$), δ: 1.260~1.230 (d, J=6 Hz, 3H), 3.751~3.756 (m, 1H), 4.081 (S, 3H), 8.230 (S, 1H), 8.501 (S, 1H), 8.2981 (S, 1H).

Reaction 3: The Preparation of (R)-5-chloro-N2-(2,5-dimethyl-4-(piperidin-4-yl)-2,3-dihydrobenzofuran-7-yl)-N4-(3-(isopropylsulfonyl)-1-methyl-1H-pyrazol-4-yl)pyrimidine-2,4-diamine (Compound REX-D1)

Step 1: The Preparation of (R)-tert-butyl-4-(7-((5-chloro-4-((3-(isopropylsulfonyl)-1-methyl-1H-pyrazol-4-yl)amino)pyrimidin-2-yl)amino)-2,5-dimethyl-2,3-dihydrobenzofuran-4-yl)piperidine-1-carboxylate (Compound 17)

The solution of compound SM$_5$ (100 mg, 288.63 μmol), SM$_{10}$ (151.63 mg, 432.95 μmol), Cs$_2$CO$_3$ (376.17 mg, 1.15 mmol), Pd(AcO)$_2$ (20 mg) and Xantphos (50 mg, 86.4 mol) in dry dioxane (10 mL) under N$_2$ was stirred at 95° C. for 14 h. The reaction was quenched with water (50 mL), extracted with EA. The organic layer was dried over anhydrous Na$_2$SO$_4$, filtered and evaporated. The residue was purified with column chromatography (PE:EA=2:1) to obtain the target compound 17 (40 mg, 20.3% yield).

Step 2: The Preparation of Compound REX-D1

The solution of compound 17 (40 mg, 60.59 μmol) in 4N HCl/Ether (10 mL) was stirred at room temperature for 4 h. Then the organic layer was washed with aqueous NaHCO$_3$ to obtain the target compound REX-D1 (32 mg, 94% yield).

MS m/z [ESI]: 561.2[M+1].

$^1$H-NMR (DMSO-d$_6$), δ: 1.260~1.230 (d, J=6 Hz, 3H), 1.358 (d, J=6 Hz, 3H), 1.460~1.545 (m, 2H), 1.545~1.715 (m, 2H), 2.124 (s, 3H), 2.620~2.860 (m, 4H), 3.238~3.318 (m, 1H), 3.751~3.756 (m, 1H) 3.920~4.140 (m, 2H), 4.081 (S, 3H), 4.289 (s, 2H), 4.683~4.783 (m, 1H), 6.258 (s, 1H). 8.230 (S, 1H), 8.501 (S, 1H), 8.2981 (S, 1H), 8.681-8.710 (m, 1H), 9.061 (S, 1H).

Example 2

(R)-5-chloro-N2-(2,5-dimethyl-4-(1-methylpiperidin-4-yl)-2,3-dihydrobenzofuran-7-yl)-N4-(3-(isopropylsulfonyl)-1-methyl-1H-pyrazol-4-yl)pyrimidine-2,4-diamine [No. REX-D2]

Synthetic Routes:

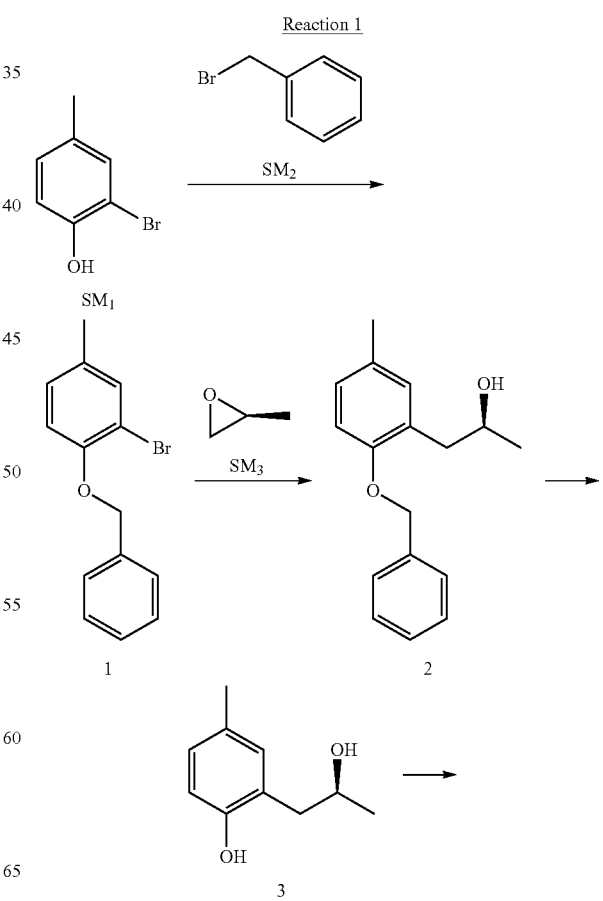

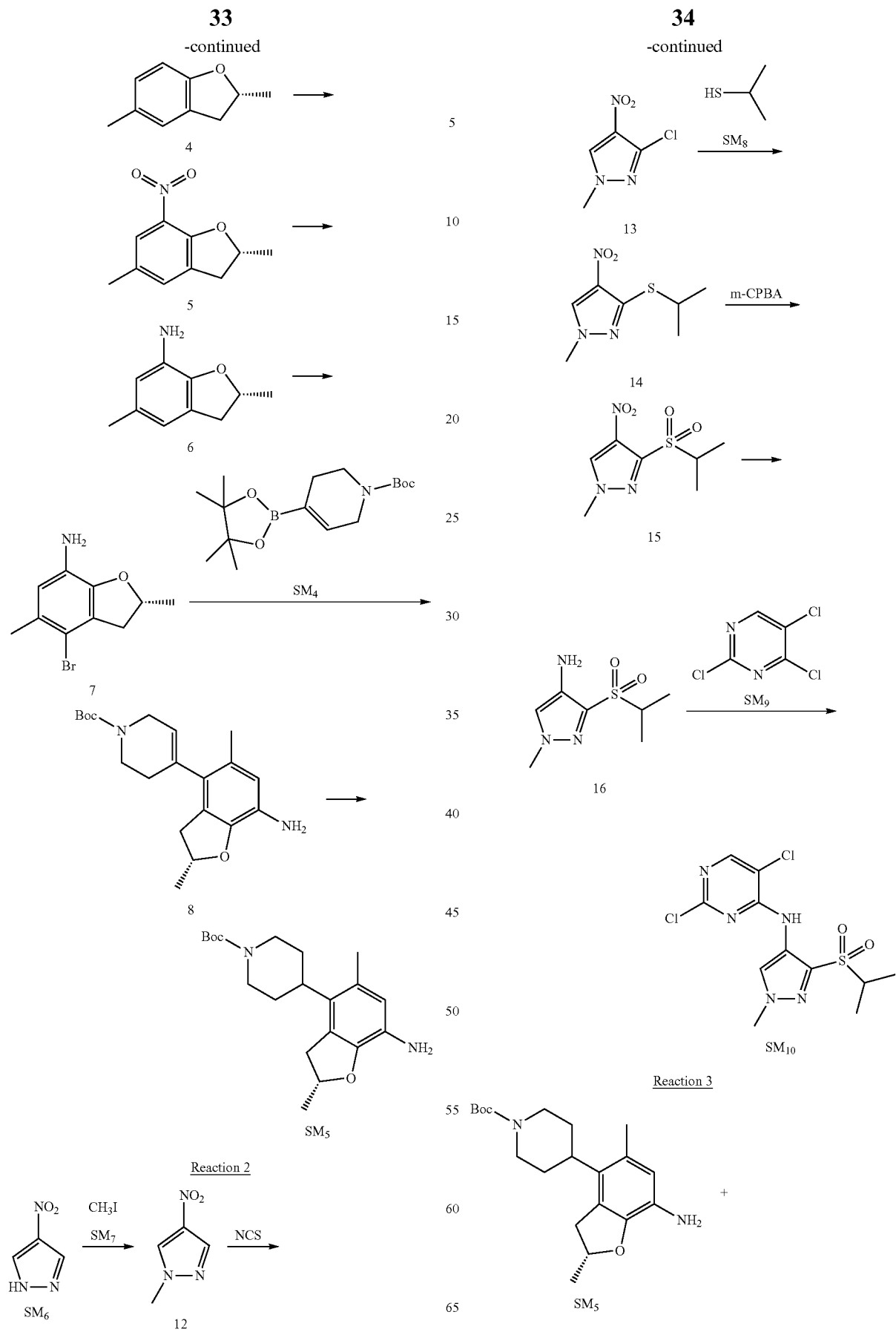

Example 3

(R)—N2-(2,5-dimethyl-4-(piperidin-4-yl)-2,3-dihydrobenzofuran-7-yl)-N4-(3-(isopropylsulfonyl)-1-methyl-1H-pyrazol-4-yl)-5-(trifluoromethyl)pyrimidine-2,4-diamine [No. REX-D3]

Synthetic Routes:

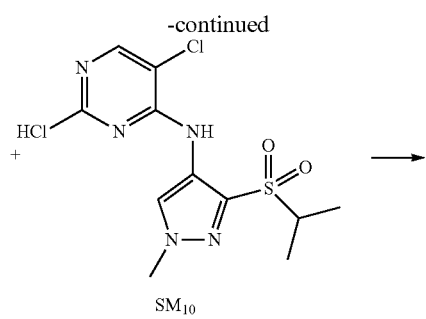

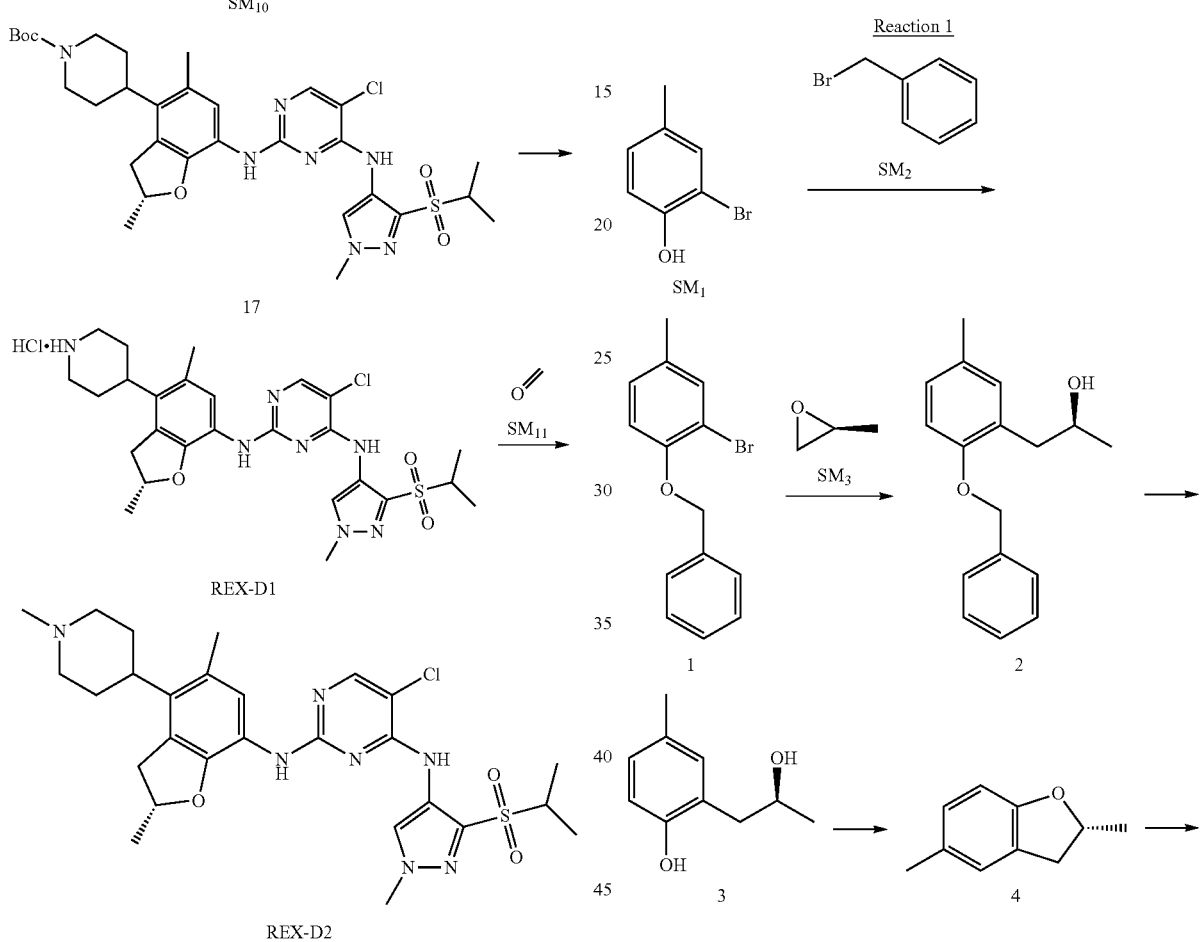

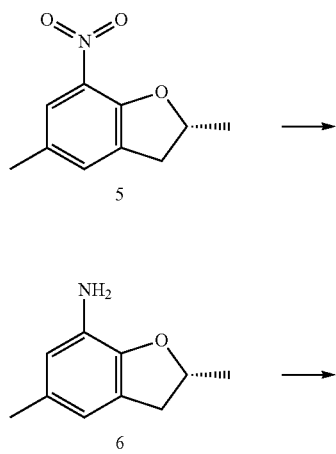

According to synthetic route as described in this example, the intermediate compound REX-D1 was obtained in the same synthetic method as in example 1 (5.0% yield), and then the target compound REX-D2 was prepared through one step reaction. The specific synthetic method was as follows:

The mixture of REX-D1 (40 mg, 70.14 μmol), Formaldehyde (22 mg, 710 μmol), CH$_3$COOH (11 mg, 170 μmol), MgSO$_4$ (200 mg) and Sodium triacetoxyborohydride (56 mg, 260 μmol) in DCM (10 mL) was stirred at 0° C. for 30 min under N$_2$. The reaction was quenched with water (50 mL) and extracted with EA. The organic layer was dried over anhydrous Na$_2$SO$_4$, filtered and evaporated. The residue was purified with column chromatography (DCM: MeOH=20:1) to obtain the target compound REX-D2 (30 mg, 78.3% yield).

MS m/z [ESI]: 576.1 [M+1].

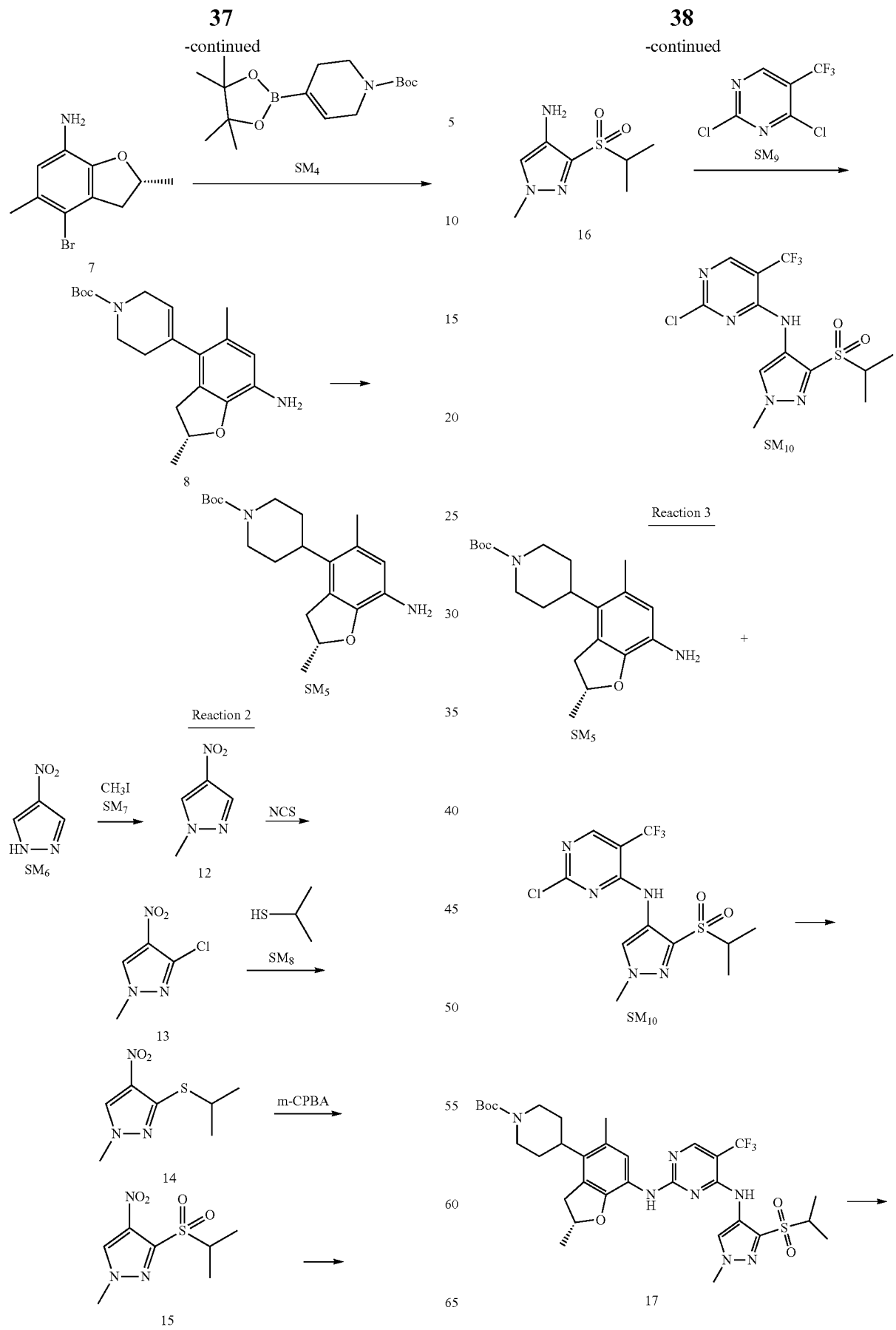

39

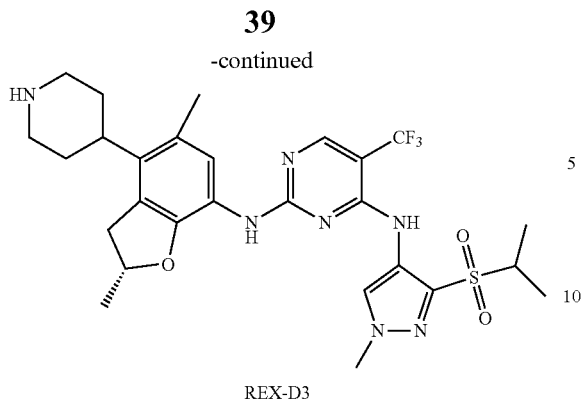

REX-D3

According to synthetic routes as described in this example, the intermediate compound SM10 ((R)—N2-(2,5-dimethyl-4-(piperidin-4-yl)-2,3-dihydrobenzofuran-7-yl)-N4-(3-(isopropylsulfonyl)-1-methyl-1H-pyrazol-4-yl)-5-(trifluoromethyl)pyrimidine-2,4-diamine) was obtained in the same manner as the reaction 1 and reaction 2 in example 1, except that the compound 2,5,6-trichloropyrimidine (SM9) was replaced by the compound 2,4-Dichloro-5-trifluoromethylpyrimidine (28% yield).

Then the target compound REX-D3 was prepared through two step reaction according to reaction 3 in this example. The specific synthetic method is as follows:

Step 1: The Preparation of (R)-tert-butyl-4-(7-((4-((3-(isopropylsulfonyl)-1-methyl-1H-pyrazol-4-yl)amino)-5-(trifluoromethyl)pyrimidin-2-yl)amino)-2,5-dimethyl-2,3-dihydrobenzofuran-4-yl)piperidine-1-carboxylate (Compound 17')

The solution of compound SM5 (100 mg, 288.63 μmol), SM10 (221.54 mg, 577.26 μmol), $Cs_2CO_3$ (376.17 mg, 1.15 mmol), $Pd(AcO)_2$ (20 mg) and Xantphos (50 mg, 86.4 μmol) in Dry dioxane (10 mL) under $N_2$ was stirred at 95° C. for 14 h. The reaction was quenched with water (50 mL), extracted with EA. The organic layer was dried over anhydrous $Na_2SO_4$, filtered and evaporated. The residue was purified with column chromatography (PE:EA=2:1) to give the target compound 17 (41 mg, 20.5% yield).

Step 2: The Preparation of REX-D3

The solution of compound 17 (41 mg, 61.59 μmol) in 4N HCl/Ether (10 mL) was stirred at room temperature for 4 h under $N_2$. Then the organic layer was washed with aqueous $NaHCO_3$ to obtain the target compound REX-D3 (33 mg, 94% yield).

MS m/z [ESI]: 594.6 [M+1].

$^1$H-NMR (DMSO-$d_6$), δ: 1.260~1.230 (m 3H), 1.337 (d, m, 3H), 1.758~1.778 (m, 2H), 1.830~1.840 (m, 2H), 2.222 (s, 3H), 2.940~3.005 (m, 4H), 3.238~3.318 (m, 1H), 3.339~3.456 (m, 1H) 4.000~4.007 (m, 2H), 4.030 (S, 3H), 4.089 (s, 2H), 4.683~4.783 (m, 1H), 4.830 (s, 1H). 7.171~7.650 (m, 2H), 8.380 (S, 1H), 9.191 (S, 1H). 9.480~9.650 (m, 1H). 10.061 (S, 1H).

40

Example 4

(R)—N2-(2,5-dimethyl-4-(1-methylpiperidin-4-yl)-2,3-dihydrobenzofuran-7-yl)-N4-(3-(isopropylsulfonyl)-1-methyl-1H-pyrazol-4-yl)-5-(trifluoromethyl)pyrimidine-2,4-diamine [No. REX-D4]

Synthetic Routes:

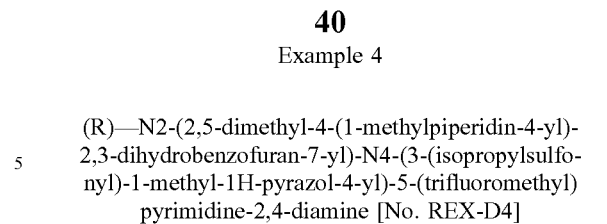

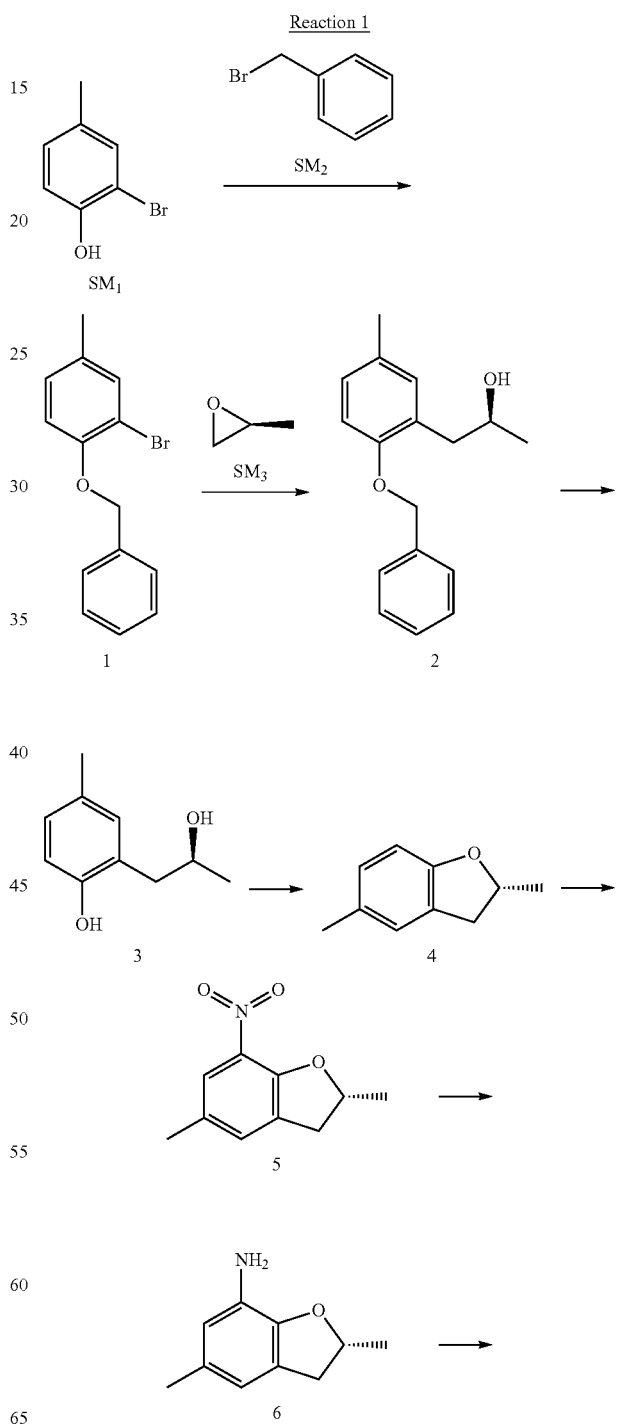

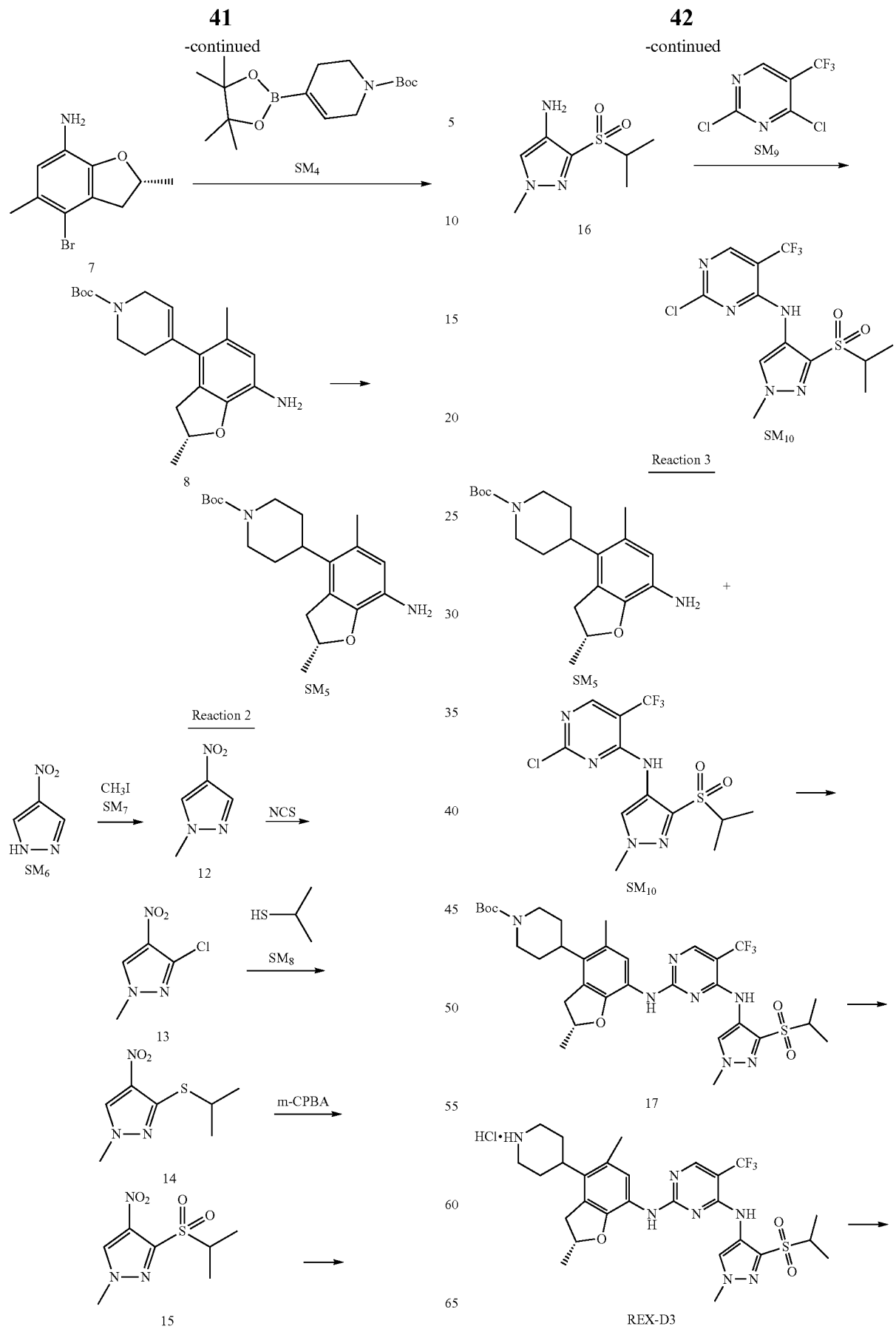

-continued

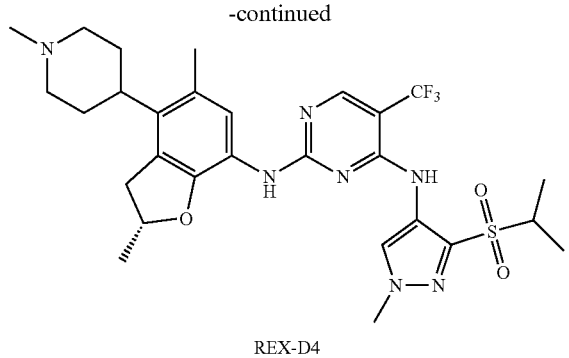

REX-D4

According to synthetic routes as described in this example, the intermediate compound REX-D3 was obtained in the same manner as in example 3 (3.0% yield), and then the target compound REX-D4 was prepared through one step reaction. The specific synthetic method was as follows:

to a mixture of REX-D3 (50 mg, 0.084 mmol) in DCM (10 mL) were added Formaldehyde (7 mg, 0.168 mmol), $CH_3COOH$ (12 mg, 0.168 mmol), $MgSO_4$ (200 mg) and Sodium triacetoxyborohydride (30.5 mg, 0.144 mmol). The mixture was stirred at 0° C. for 30 min under $N_2$. The reaction was quenched with water (50 mL) and extracted with EA. The organic layer was dried over anhydrous $Na_2SO_4$, filtered and evaporated. The residue was purified with column chromatography (DCM:MeOH=20:1) to obtain the target compound REX-D4 (35 mg, 79.3% yield).

MS m/z [ESI]: 609.1 [M+1].

1H-NMR (DMSO-d6): 1.15-1.20 (m, 8H), 1.23-1.30 (m, 3H), 1.78-1.81 (m, 2H), 2.02-2.19 (m, 2H), 2.25 (S, 3H), 2.73 (m, 3H), 2.87-2.98 (m, 4H), 3.42-2.983.48 (m, 1H), 3.98 (s, 3H), 4.78-4.88 (m, 1H), 8.31 (s, 1H), 8.42 (s, 1H), 9.34 (s, 1H).

Example 5

(R)-2-(4-(7-((4-((3-(isopropylsulfonyl)-1-methyl-1H-pyrazol-4-yl)amino)-5-(trifluoromethyl)pyrimidin-2-yl)amino)-2,5-dimethyl-2,3-dihydrobenzofuran-4-yl)piperidin-1-yl)ethanol [No. REX-D5]

Synthetic Routes:

Reaction 1

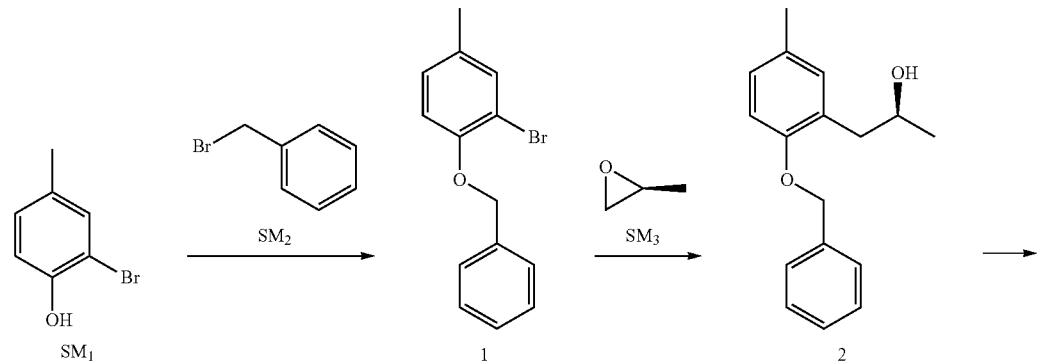

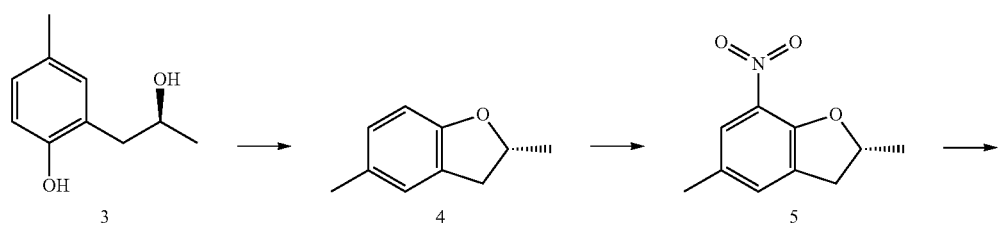

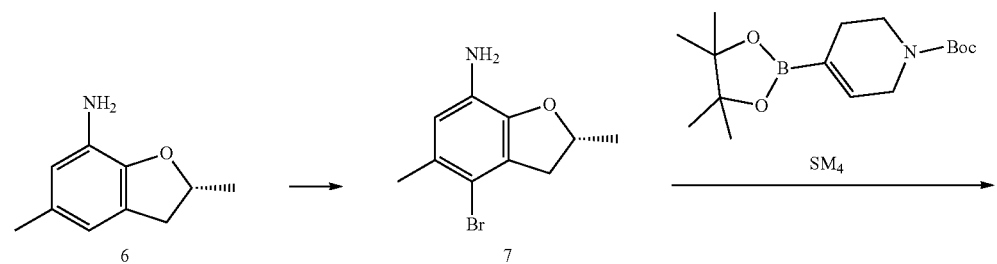

-continued
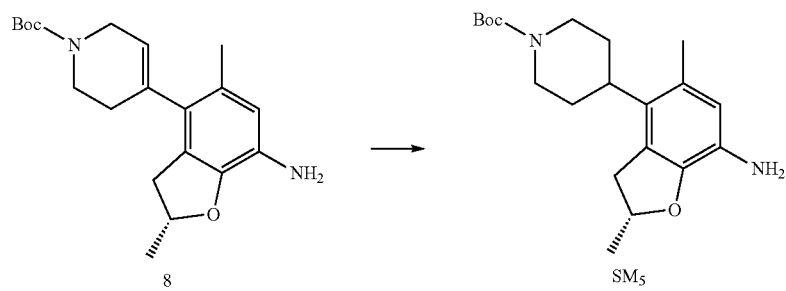
Reaction 2
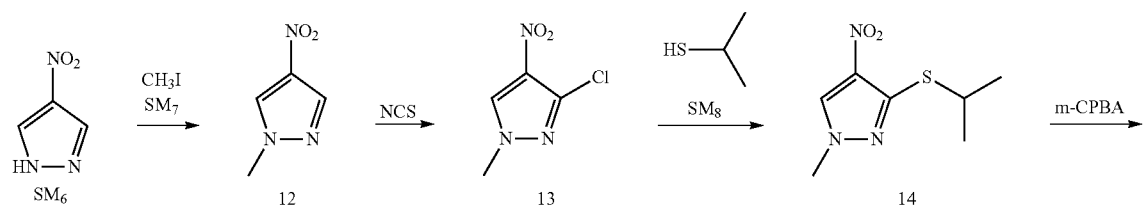
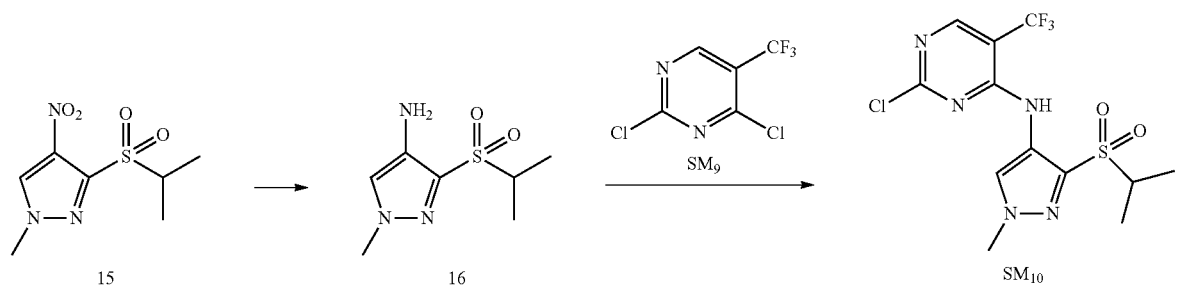
Reaction 3
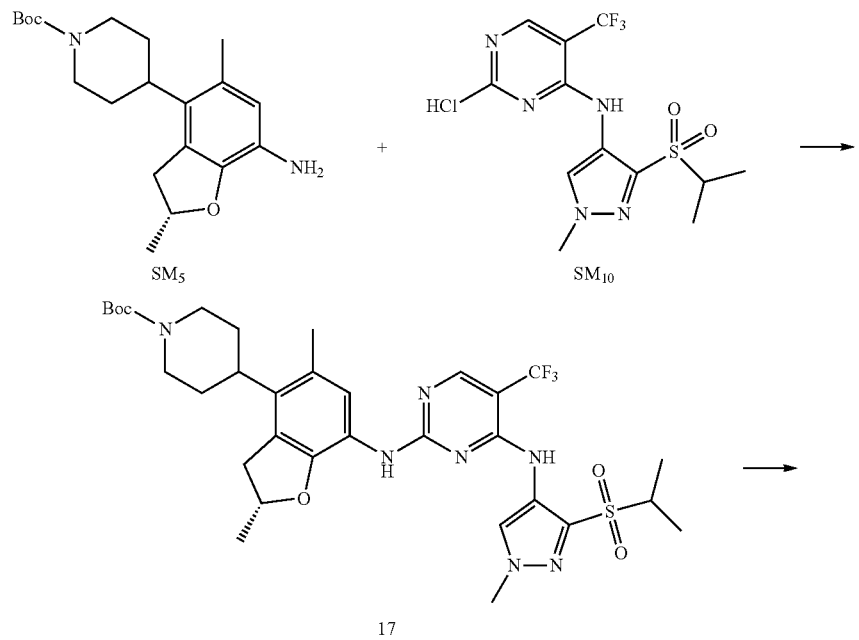

-continued

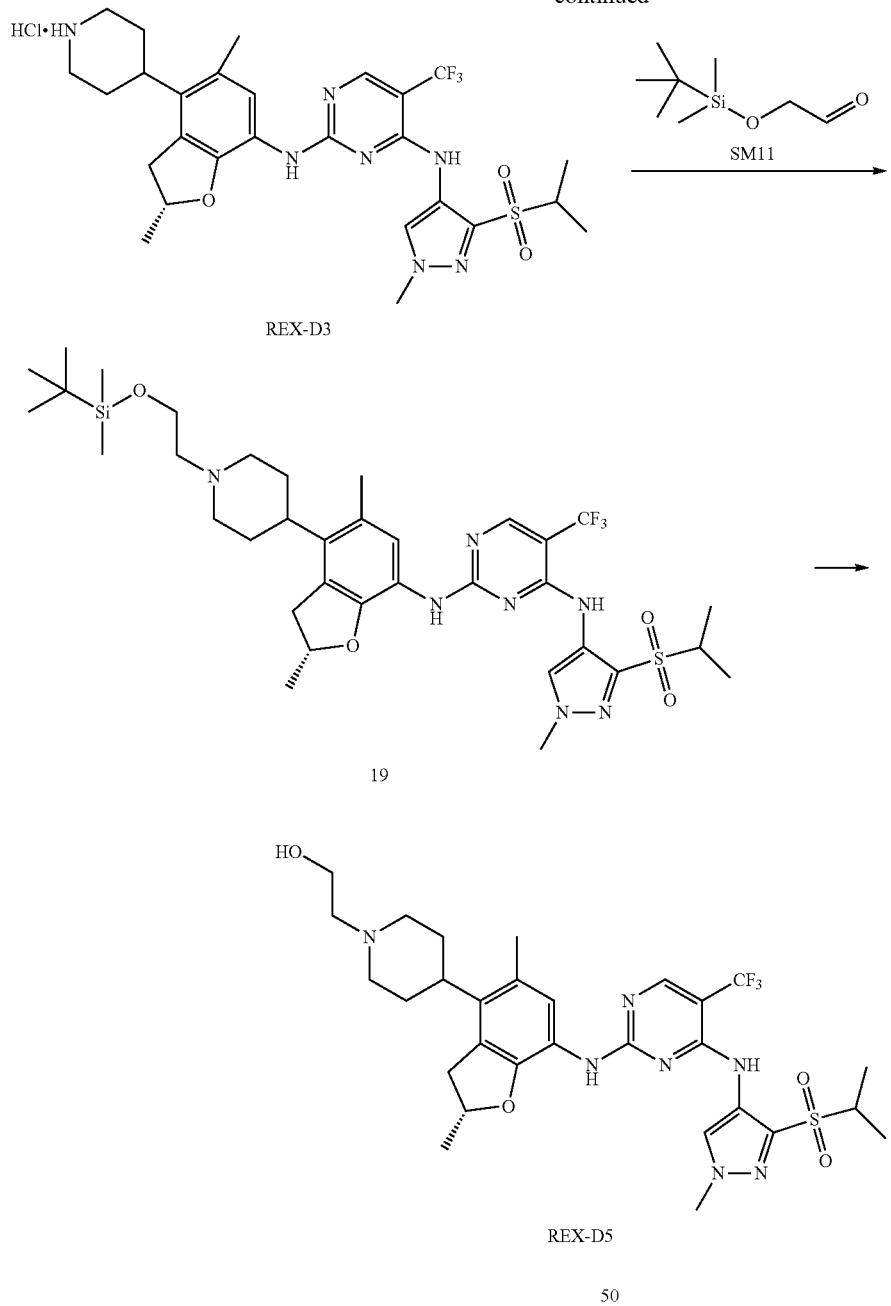

According to synthetic routes as described in this example, the intermediate compound REX-D3 was firstly obtained in the same synthetic method as in example 3 (5.0% yield), and then the target compound REX-D5 was prepared through two step reaction. The specific synthetic method was as follows:

Step 1: The Preparation of Compound 19

The mixture of REX-D3 (300 mg, 0.336 mmol), SM$_{11}$ (293 mg, 1.68 mmol), CH$_3$COOH (12 mg, 0.168 mmol), MgSO$_4$ (200 mg) and Sodium triacetoxyborohydride (30.5 mg, 0.144 mmol) in DCM (10 mL) at RT. The reaction was stirred at 0° C. for 30 min under N$_2$. The reaction was quenched with water (50 mL) and extracted with EA. The organic layer was dried over anhydrous Na$_2$SO$_4$, filtered and evaporated. The residue was purified with column chromatography (DCM:MeOH=50:1) to obtain the target compound 19 (150 mg, 59.3% yield).

MS m/z [ESI]: 752.1[M+1].

Step 2: the Preparation of REX-D5

The solution of compound 19 (150 mg, 0.199 mmol) in 4N HCl/Ether (10 mL) was stirred at room temperature for 4 h under N$_2$. Then the organic layer was washed with aqueous NaHCO$_3$ to obtain the target compound REX-D5 (30 mg, 24% yield).

MS m/z [ESI]: 655.6 [M+1].

$^1$H-NMR (DMSO-d$_6$): 1.21-1.27 (m, 9H), 1.36-1.39 (m, 2H), 1.65-1.68 (m, 2H), 2.29-2.31 (m, 4H), 2.57-2.60 (m, 2H), 2.93-2.98 (m, 1H), 3.10-3.11 (m, 1H), 3.52-3.59 (m, 8H), 3.95-3.99 (m, 4H), 4.79 (s, 1H), 8.35 (s, 1H), 8.46 (s, 1H), 9.38 (s, 1H).

Example 6
(R)—N2-(5-fluoro-2-methyl-4-(1-methylpiperidin-4-yl)-2,3-dihydrobenzofuran-7-yl)-N4-(3-(isopropyl-sulfonyl)-1-methyl-1H-pyrazol-4-yl)-5-(trifluoromethyl)pyrimidine-2,4-diamine [No. REX-D8]
Synthetic Routes:
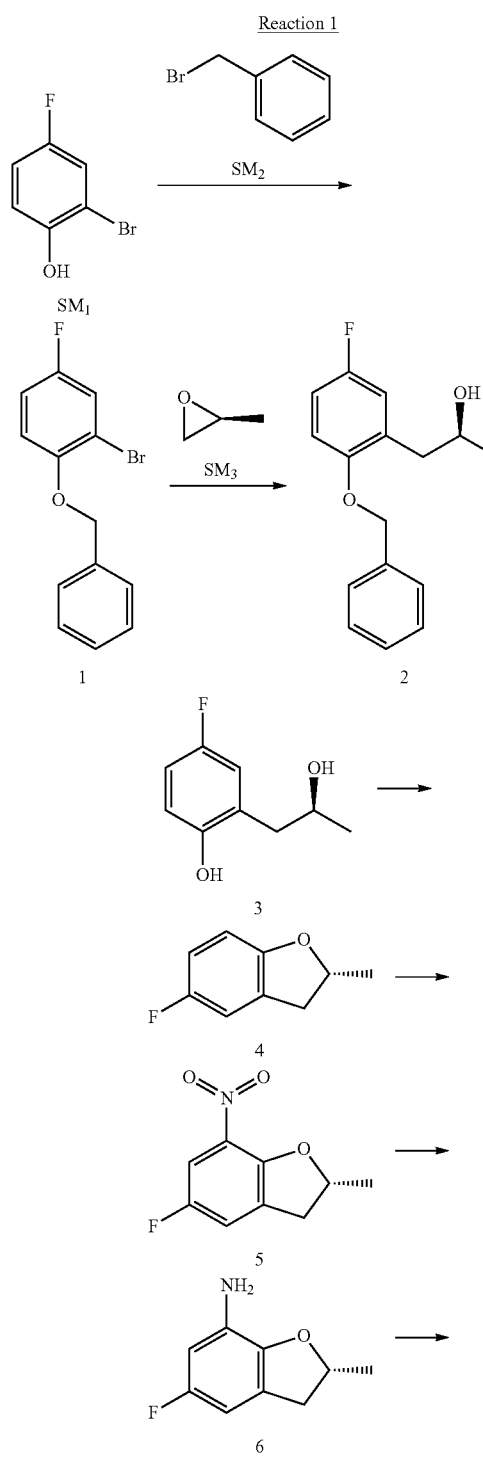
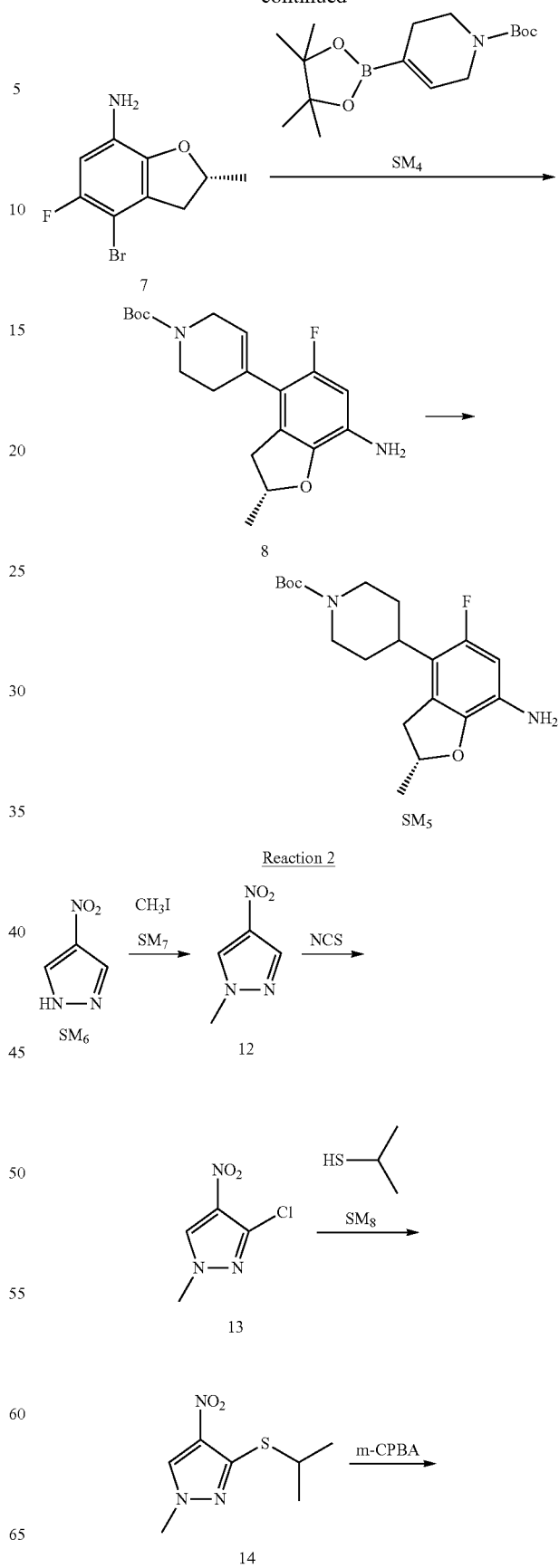

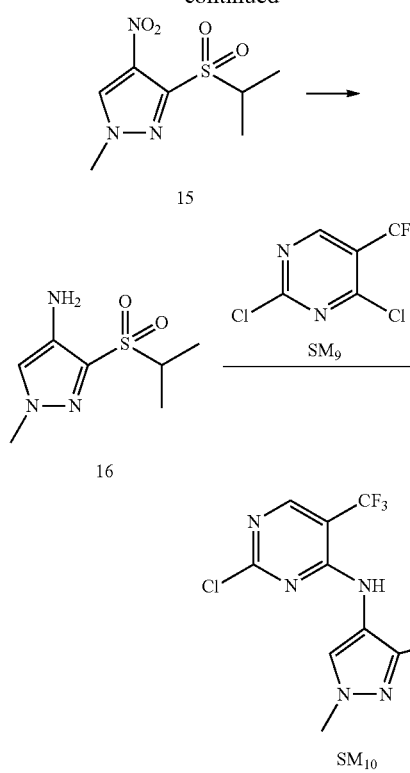

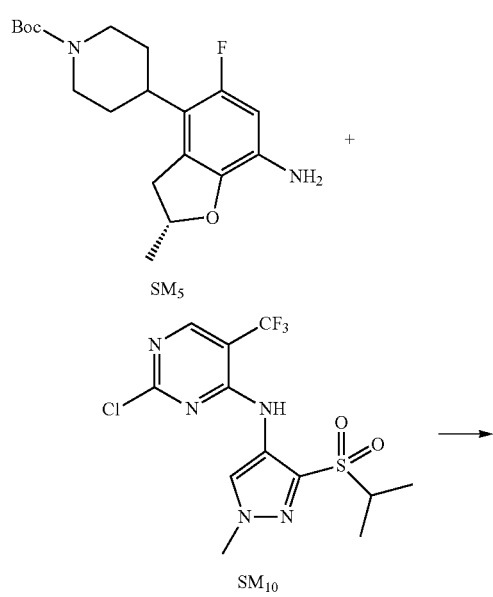

According to synthetic routes as described in this example, the intermediate compound SM5 ((R)-tert-butyl4-(7-amino-5-fluoro-2-methyl-2,3-dihydrobenzofuran-4-yl)piperidine-1-carboxylate) was prepared in the same manner as the reaction 1 and reaction 2 in example 1, except that the compound 2-bromo-4-methylphenol (SM1) in example 1 was replaced by the compound 2-bromo-4-fluorophenol. (25% yield).

According to synthetic routes as described in this example, the compound REX-D8 was obtained in the same synthetic method as in example 4. (5.0% yield).

MS m/z [ESI]: 612.6 [M+1].

Example 7

(R)—N4-(1-cyclopropyl-3-(isopropylsulfonyl)-1H-pyrazol-4-yl)-N2-(2,5-dimethyl-4-(1-methylpiperidin-4-yl)-2,3-dihydrobenzofuran-7-yl)-5-(trifluoromethyl)pyrimidine-2,4-diamine [No. REX-D9]

Synthetic Routes:

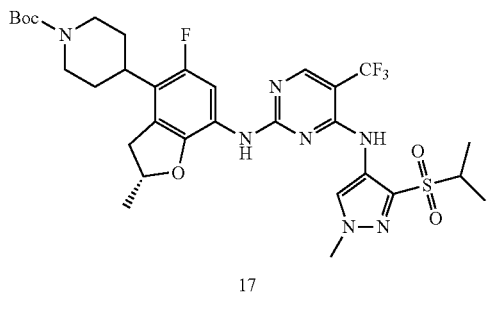

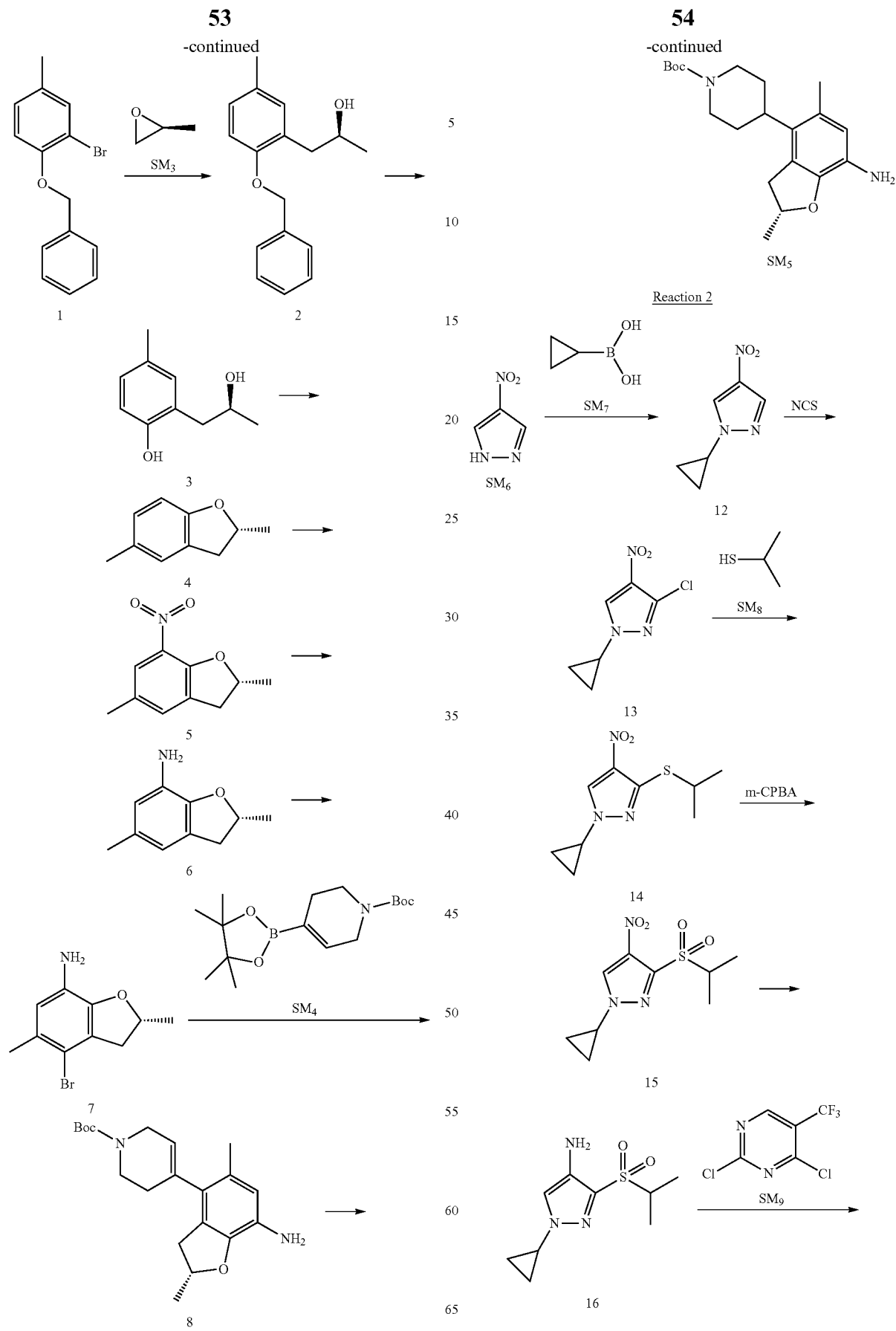

-continued

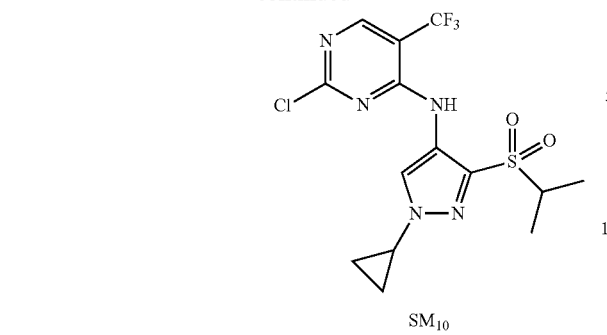

SM10

Reaction 3

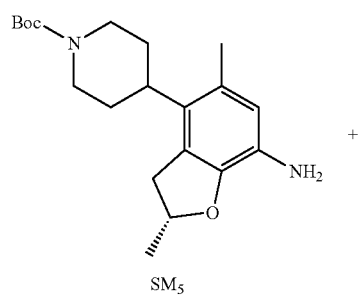

SM5

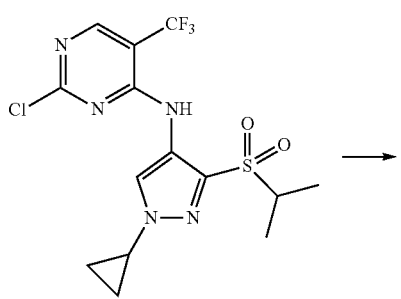

SM10

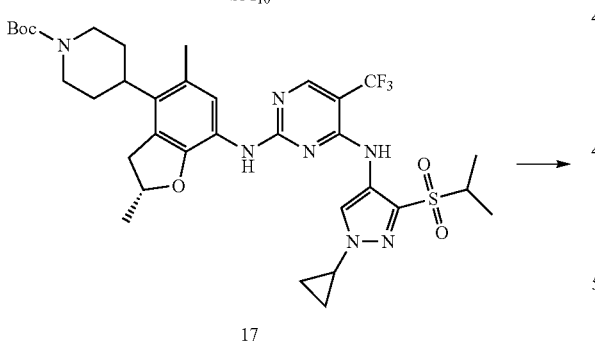

17

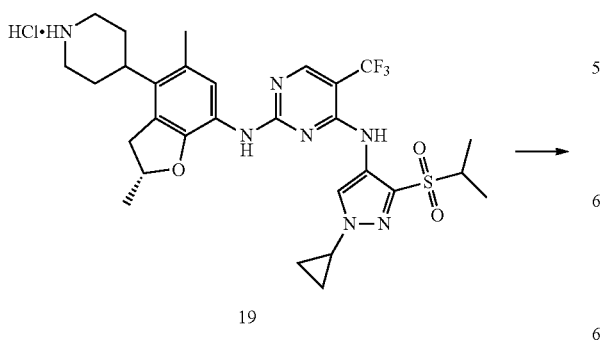

19

-continued

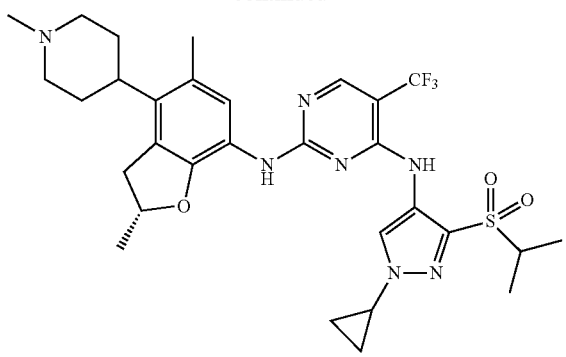

REX-D9

According to synthetic routes as described in this example, the intermediate compound SM10 (2-chloro-N-(1-cyclopropyl-3-(isopropylsulfonyl)-1H-pyrazol-4-yl)-5-(trifluoromethyl) pyrimidin-4-amine) was obtained in the same manner as the reaction 1 and reaction 2 in example 4, except that the compound iodomethane (SM7) in example 4 was replaced by the compound cyclopropylboronic acid. (30% yield).

According to synthetic routes as described in this example, the compound REX-D9 was obtained in the same synthetic method as in example 4. (6.2% yield).

MS m/z [ESI]: 634.6 [M+1].

$^1$H-NMR (DMSO-$d_6$): 1.21-1.27 (m, 9H), 1.40-1.41 (m, 3H), 1.80-1.83 (m, 2H), 2.27-2.29 (m, 4H), 2.91-3.03 (m, 4H), 3.47-3.50 (m, 1H), 3.52-3.58 (m, 1H), 4.76 (s, 1H), 4.96 (s, 1H), 8.35 (s, 1H), 8.50 (s, 1H), 9.36 (s, 1H).

Example 8

(R)—N2-(2,5-dimethyl-4-(1-methylpiperidin-4-yl)-2,3-dihydrobenzofuran-7-yl)-N4-(3-(isobutylsulfonyl)-1-methyl-1H-pyrazol-4-yl)-5-(trifluoromethyl) pyrimidine-2,4-diamine [No. REX-D10]

Synthetic Routes:

Reaction 1

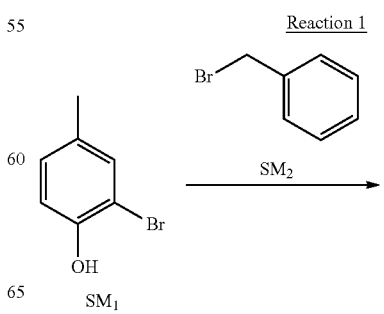

SM1

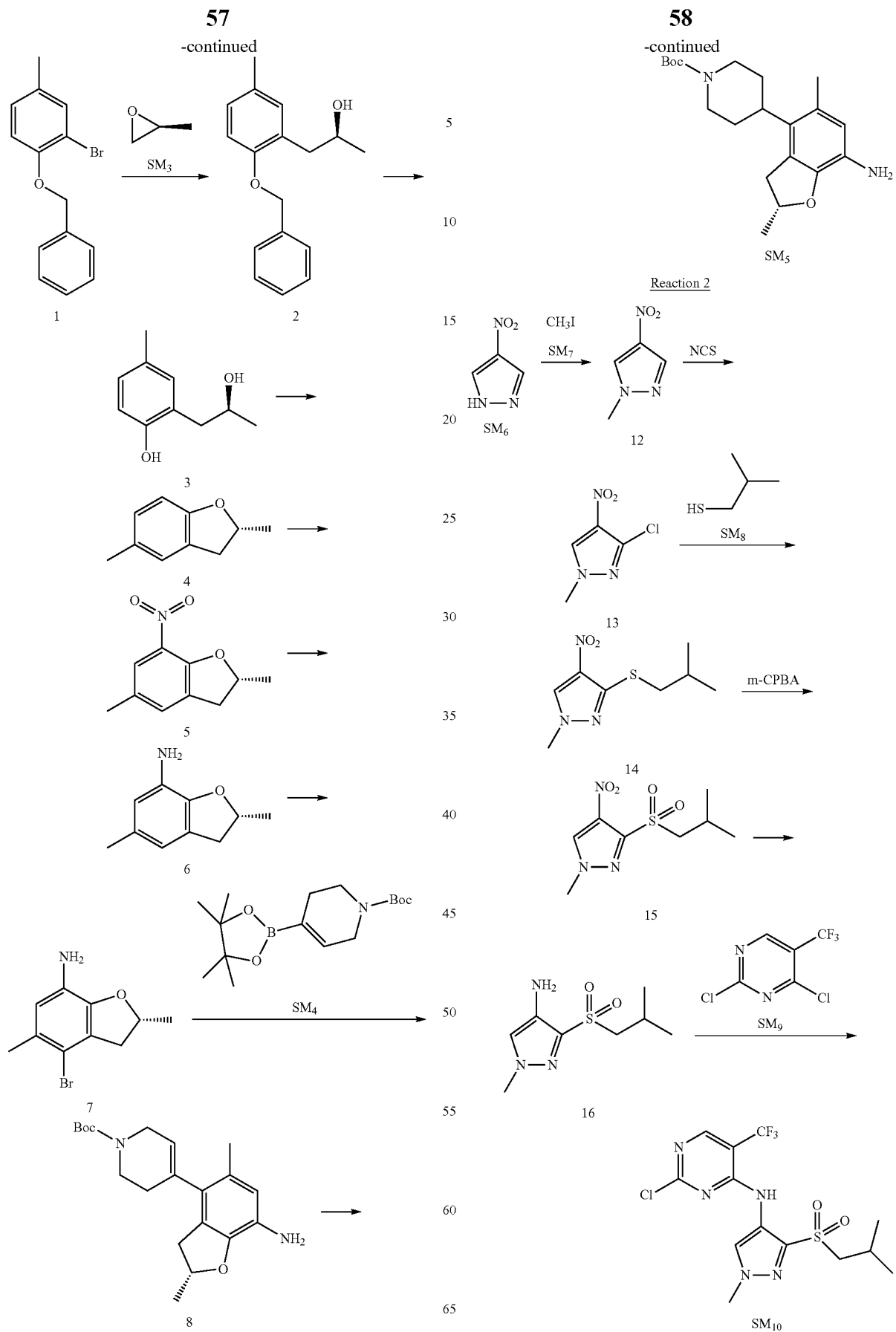

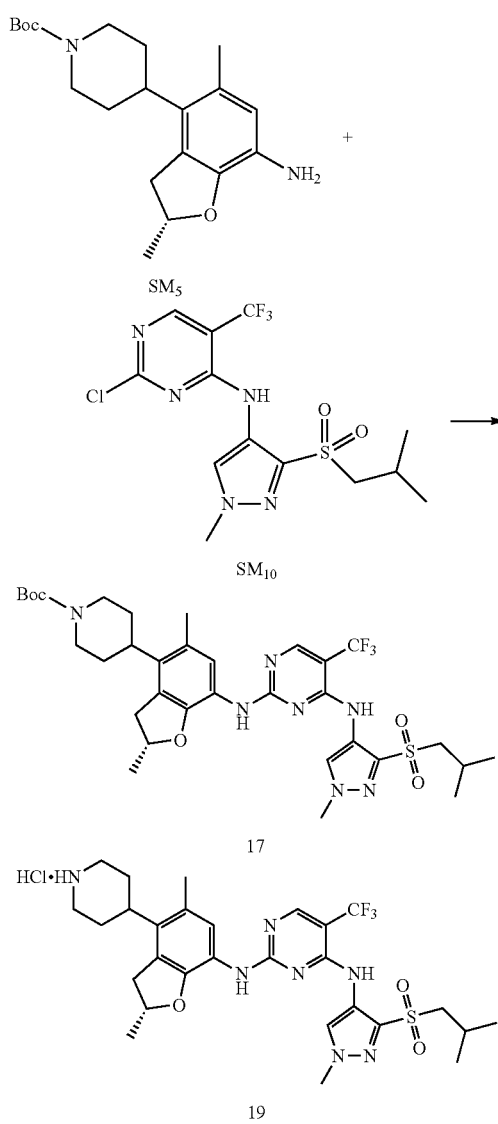

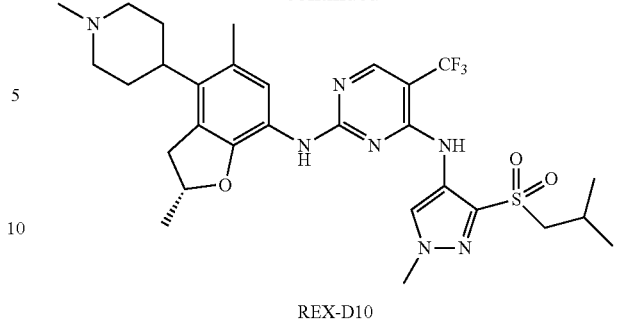

According to synthetic routes as described in this example, the intermediate compound SM10 (2-chloro-N-(3-(isobutylsulfonyl)-1-methyl-1H-pyrazol-4-yl)-5-(trifluoromethyl) pyrimidin-4-amine) was obtained in the same manner as the reaction 1 and reaction 2 in example 4, except that the compound propane-2-thiol (SM8) in example 4 was replaced by the compound 2-methylpropane-1-thiol. (35.0% yield).

According to synthetic routes as described in this example, the compound REX-D10 was obtained in the same synthetic method as in example 4. (4.2% yield).

MS m/z [ESI]: 622.6 [M+1].

$^1$H-NMR (DMSO-$d_6$), δ: 0.98-0.99 (m, 6H), 1.23-1.31 (m, 4H), 1.73-1.76 (m, 2H), 1.2.00-2.03 (m, 1H), 2.26-2.28 (m, 4H), 2.95-3.10 (m, 2H), 3.13-3.17 (m, 1H), 3.33-3.35 (m, 2H), 3.57 (s, 3H), 4.03 (s, 3H), 4.83-4.84 (m, 1H), 6.99-7.00 (m, 1H), 8.13-8.15 (m, 1H), 8.81 (s, 1H), 9.15-9.17 (m, 1H), 9.34-9.37 (m, 1H), 9.74 (s, 1H).

Example 9

(R)-2-(4-(7-((5-chloro-4-((3-(isopropylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanol [No. REX-D11]

Synthetic Routes:

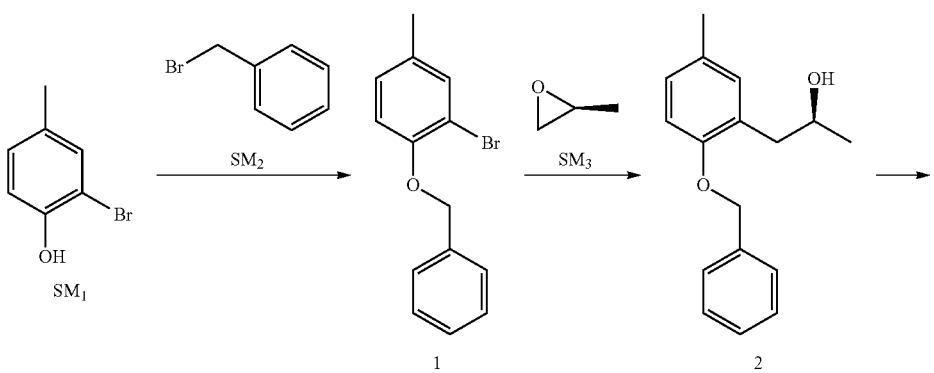

-continued
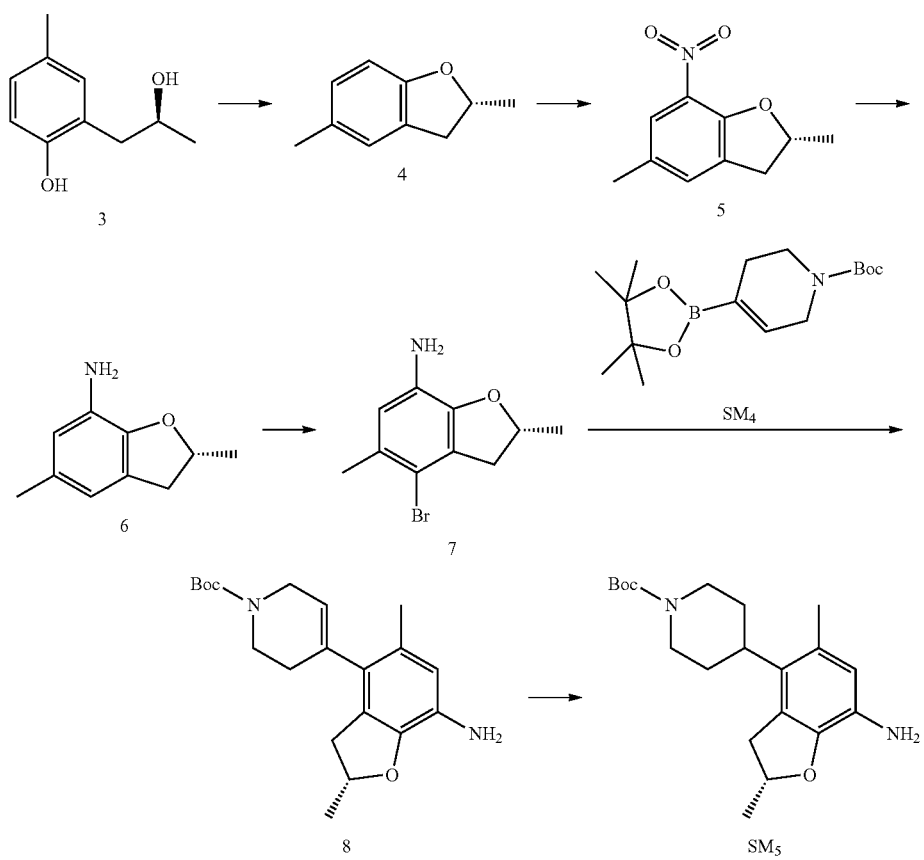
Reaction 2
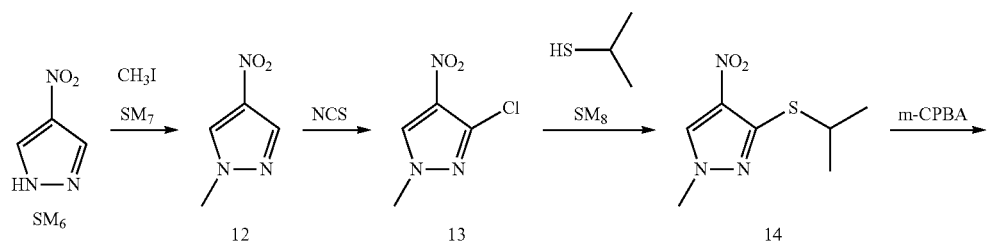
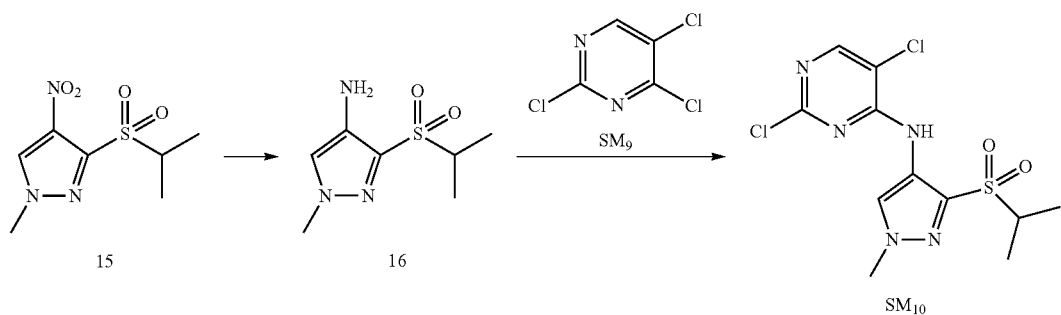

-continued
Reaction 3
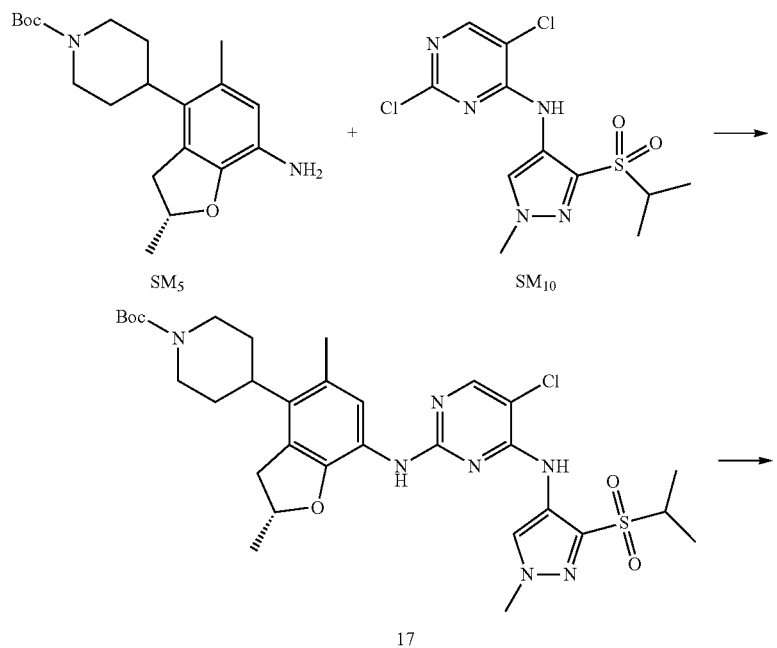
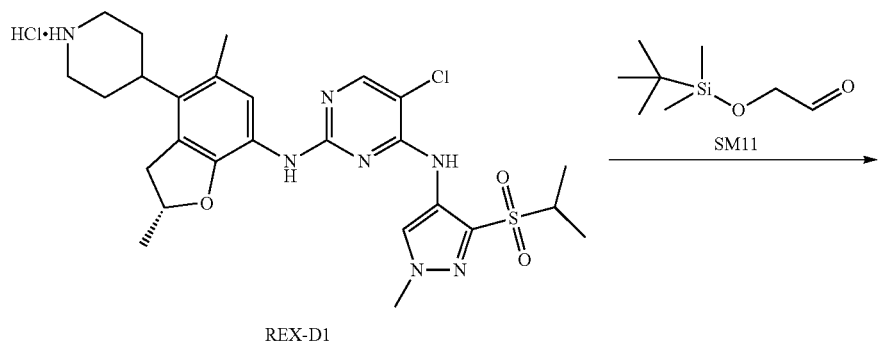
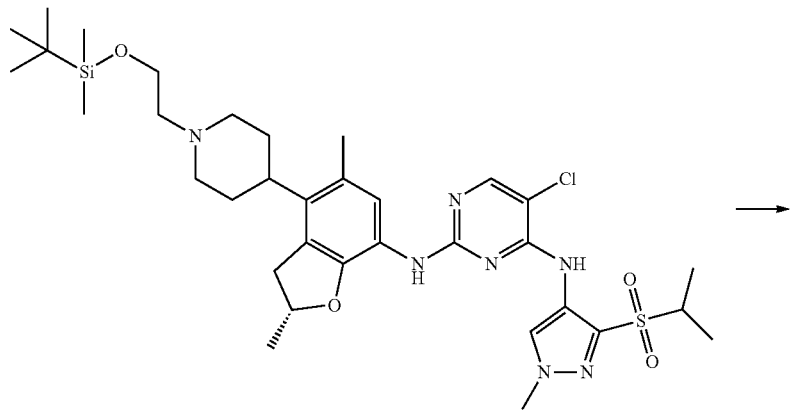

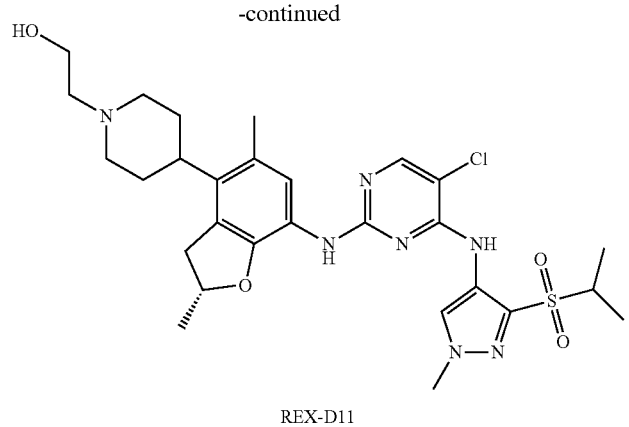

REX-D11

According to synthetic routes as described in this example, the intermediate compound SM10 (2,5-dichloro-N-(3-(isopropylsulfonyl)-1-methyl-1H-pyrazol-4-yl)pyrimidin-4-amine) was prepared in the same manner as the reaction 1 and reaction 2 in example 5, except that the compound 2,4-dichloro-5-(trifluoromethyl)pyrimidine (SM9) in example 5 was replaced by the compound 2,4,5-trichloropyrimidine. (45.0% yield).

According to synthetic routes as described in this example, the compound REX-D11 was obtained in the same synthetic method as in example 5. (8.2% yield).

MS m/z [ESI]: 605.1 [M+1].

Example 10

(R)-1-(4-(7-((5-chloro-4-((3-(isopropylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanone [No. REX-D12]

Synthetic Routes:

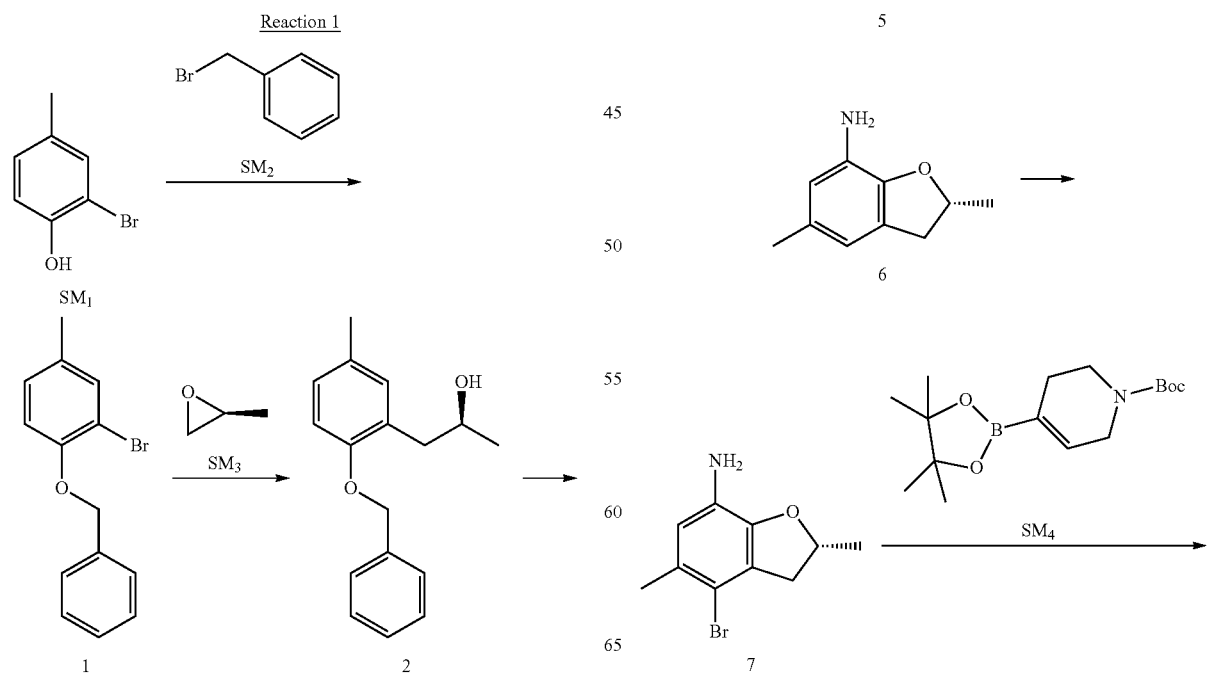

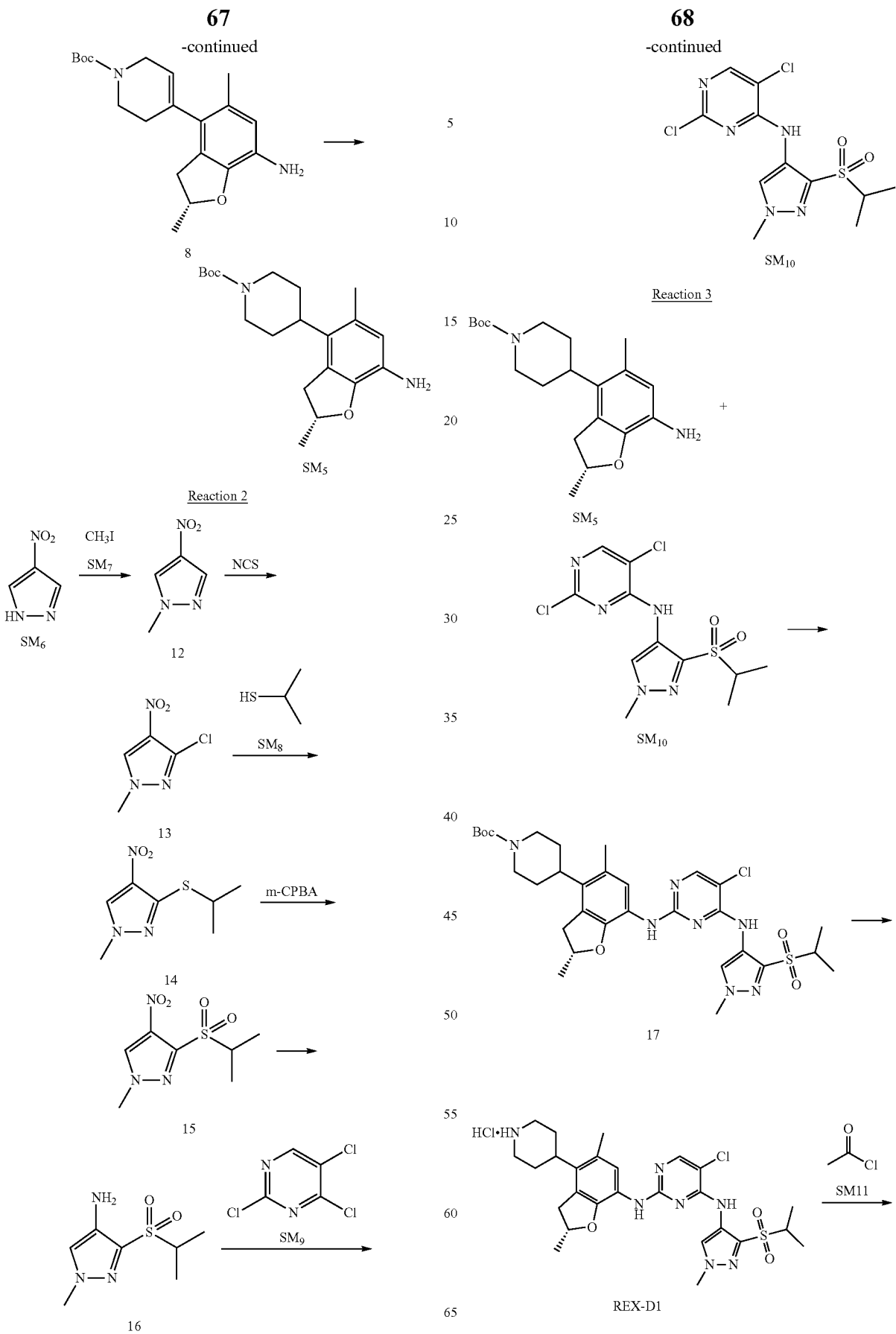

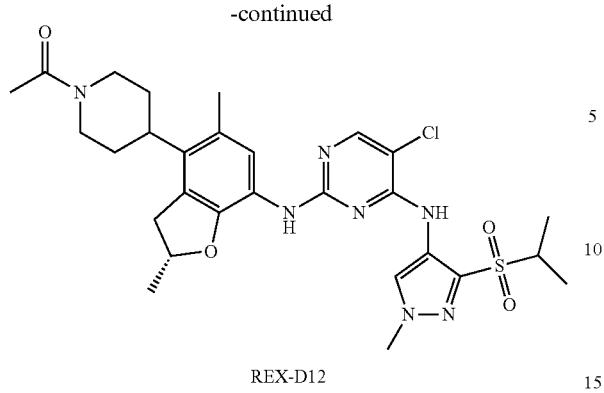

REX-D12

According to synthetic routes as described in this example, the compound REX-D12 was obtained in the same manner as the reaction 1, reaction 2 and reaction 3 in example 2, except that the compound Formaldehyde (SM11) in example 2 was replaced by the compound acetyl chloride. (5.2% yield). MS m/z [ESI]: 603.1 [M+1].

Example 11

(R)—N2-(4-([1,4'-bipiperidin]-4-yl)-2,5-dimethyl-2,3-dihydrobenzofuran-7-yl)-5-chloro-N4-(3-(isopropylsulfonyl)-1-methyl-1H-pyrazol-4-yl)pyrimidine-2,4-diamine [No. REX-D13]

Synthetic Routes:

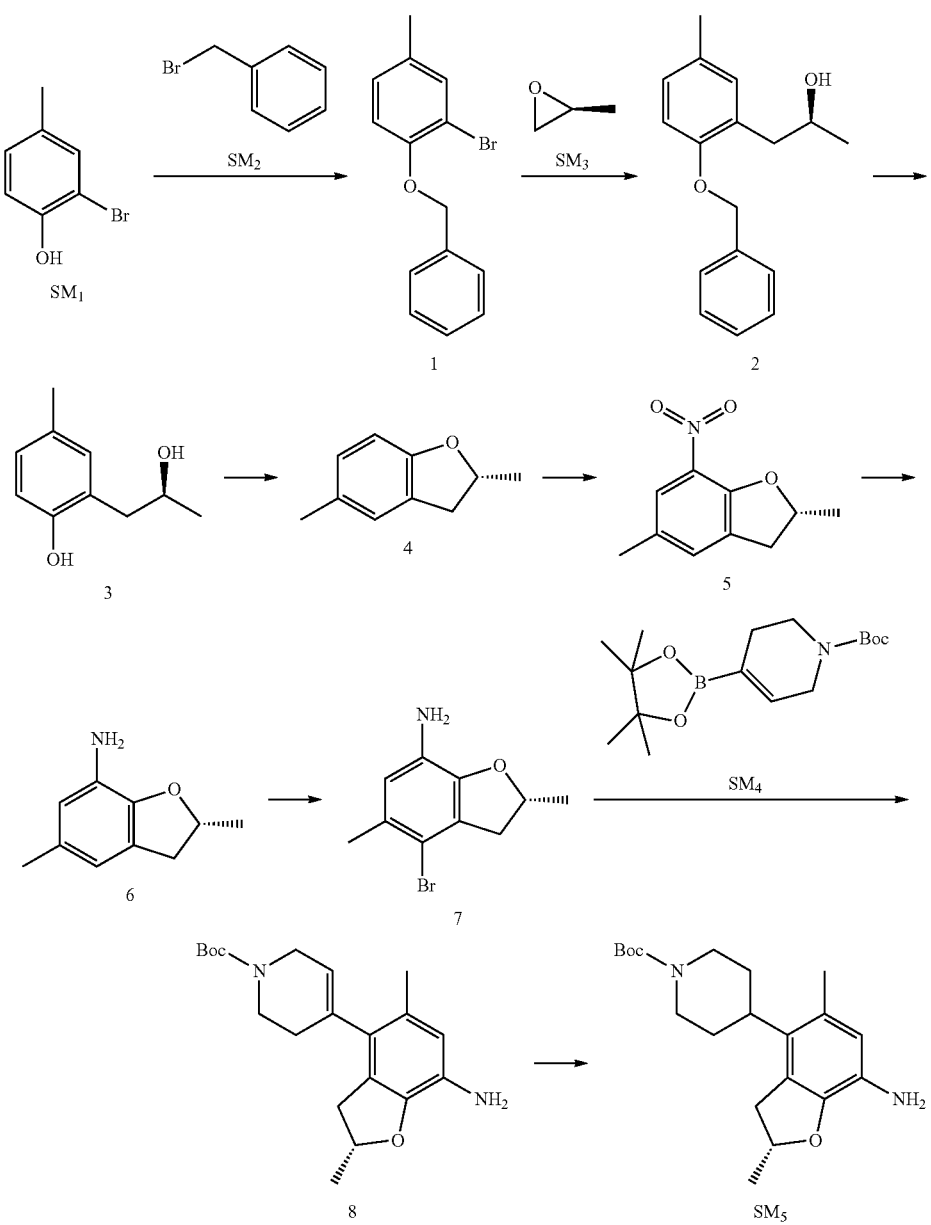

-continued
Reaction 2
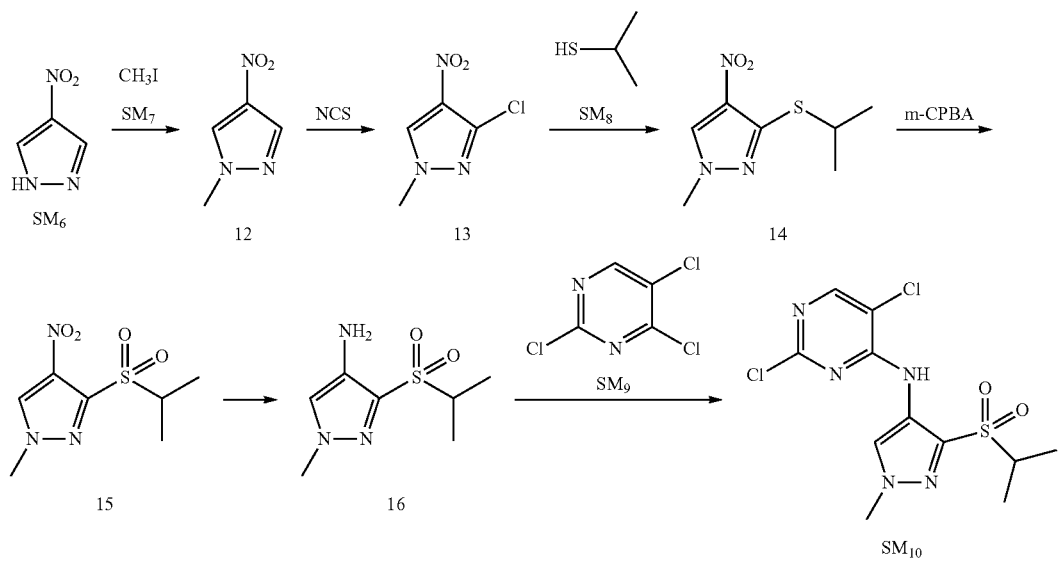
Reaction 3
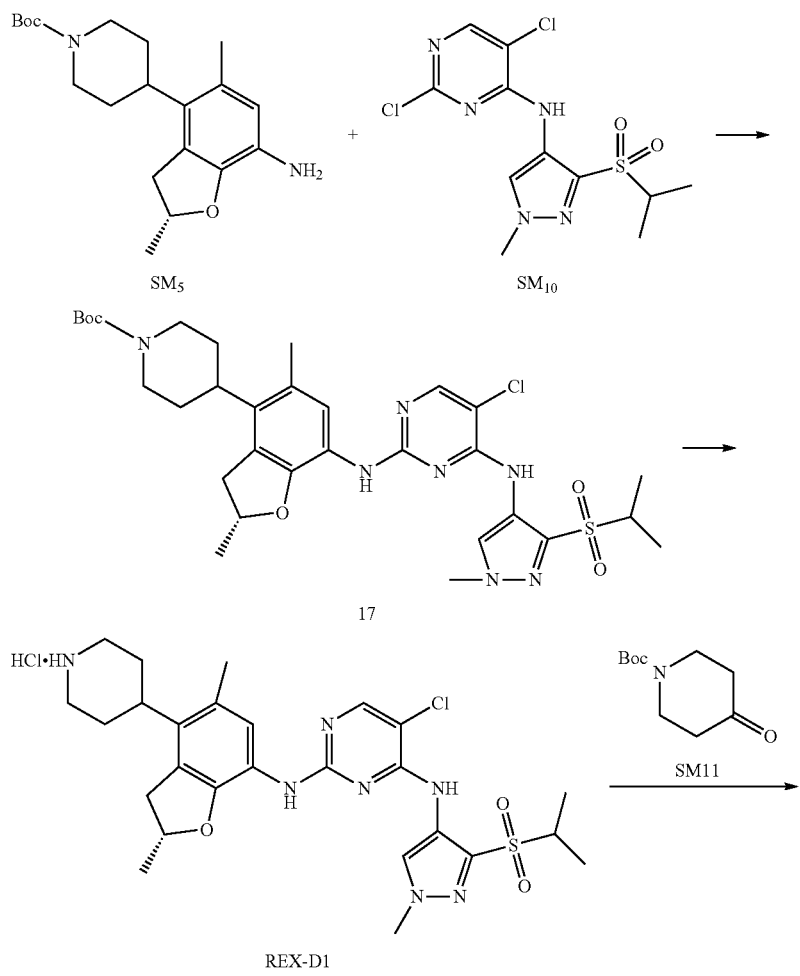

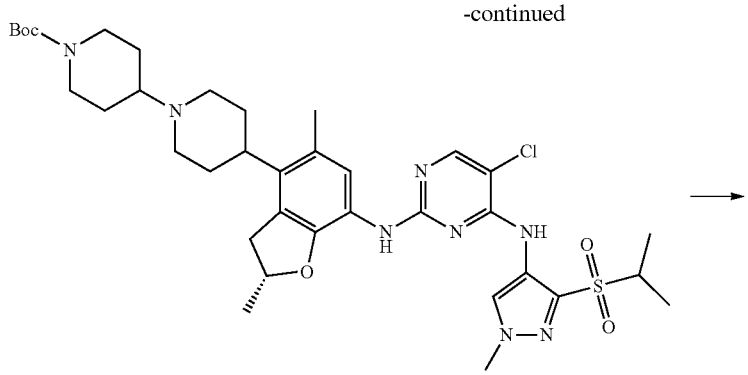

19

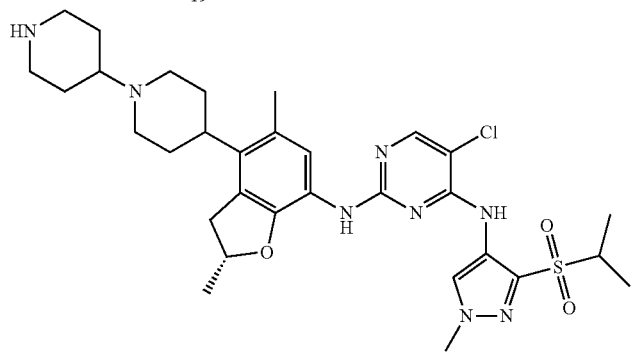

REX-D13

According to synthetic routes as described in this example, the compound REX-D13 was obtained in the same manner as the reaction 1, reaction 2 and reaction 3 in example 2, except that the compound Formaldehyde (SM11) in example 2 was replaced by the compound tert-butyl-4-oxopiperidine-1-carboxylate. (3.0% yield).

MS m/z [ESI]: 644.1 [M+1].

Example 12

(R)-5-chloro-N2-(4-(1-isopropylpiperidin-4-yl)-2,5-dimethyl-2,3-dihydrobenzofuran-7-yl)-N4-(3-(isopropylsulfonyl)-1-methyl-1H-pyrazol-4-yl)pyrimidine-2,4-diamine [No. REX-D14]

Synthetic Routes:

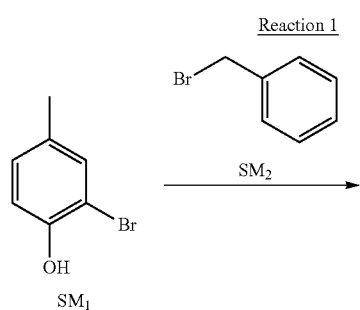

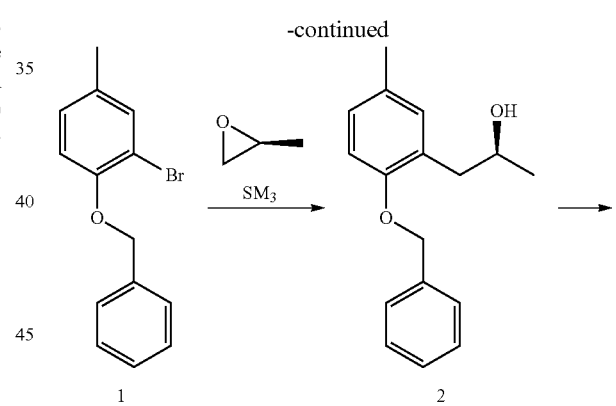

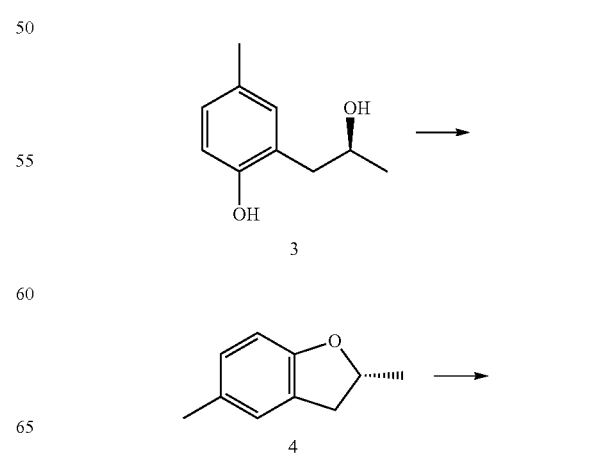

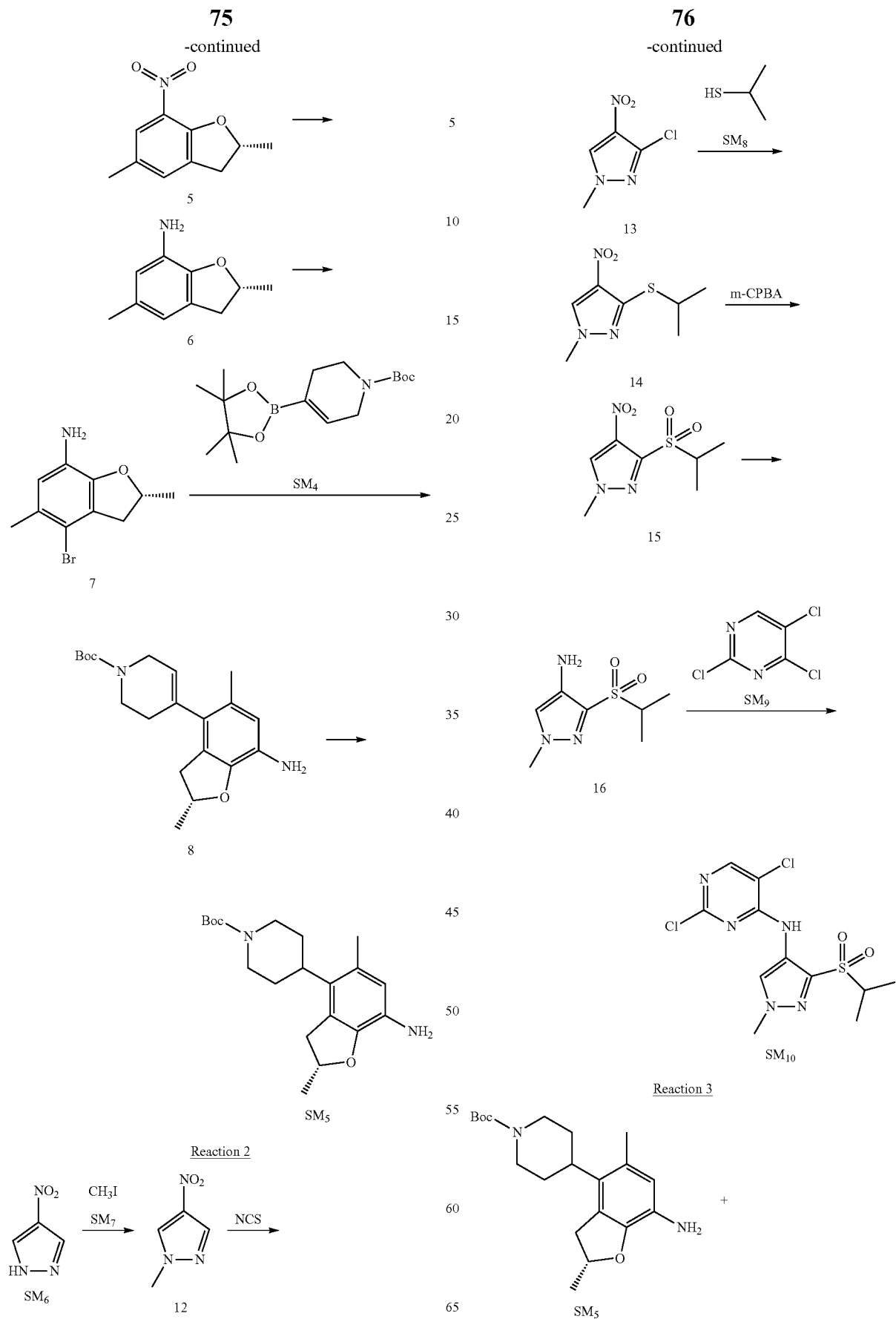

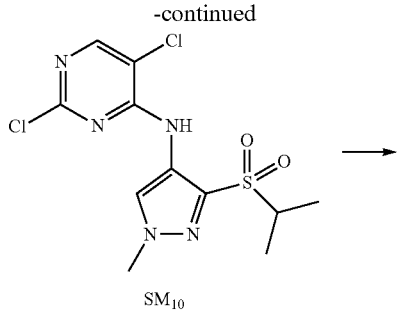
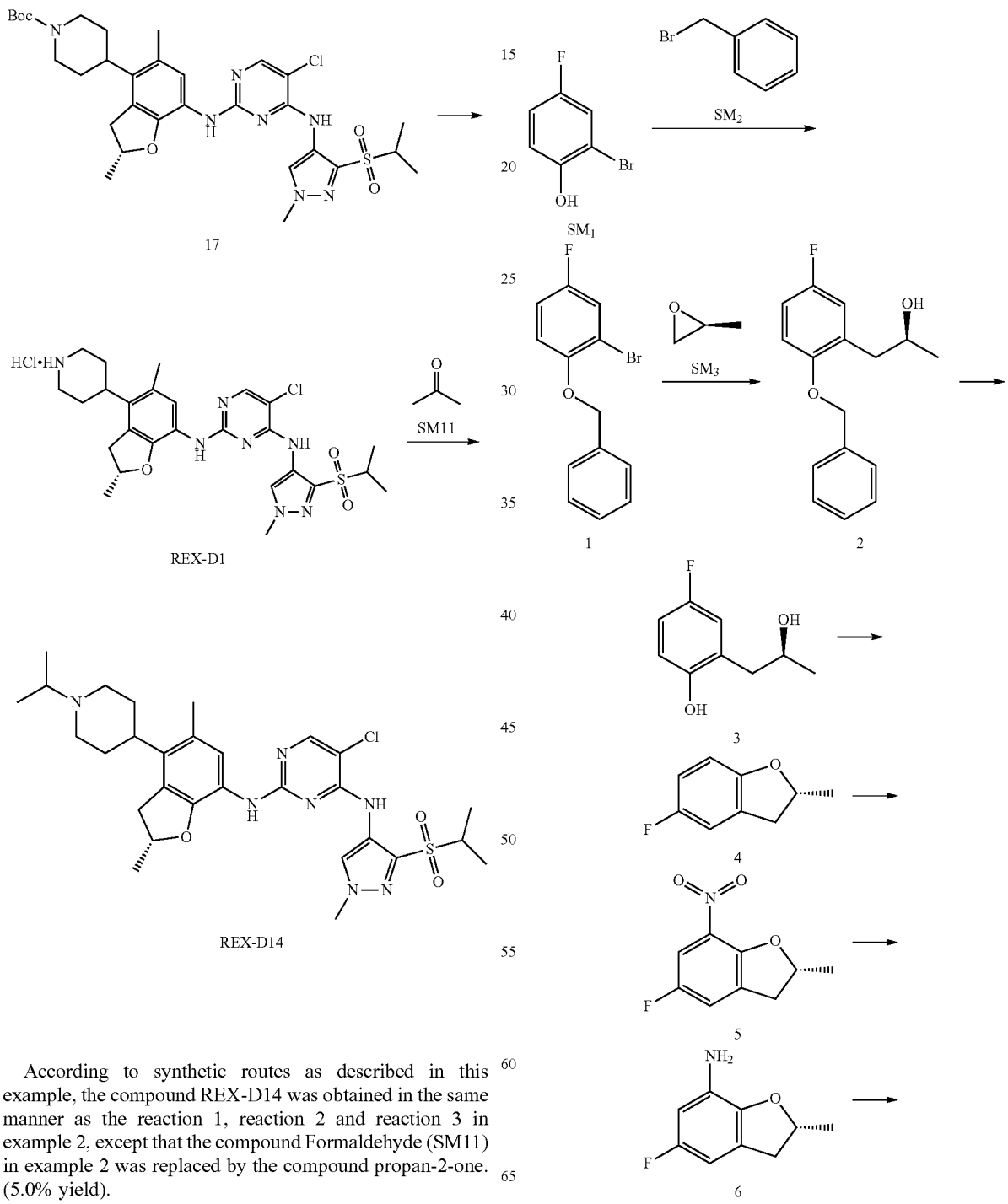

Example 13

(R)-5-chloro-N2-(4-(1-isopropylpiperidin-4-yl)-2,5-dimethyl-2,3-dihydrobenzofuran-7-yl)-N4-3-(isopropylsulfonyl)-1-methyl-1H-pyrazol-4-yl)pyrimidine-2,4-diamine [No. REX-D21]

Synthetic Routes:

According to synthetic routes as described in this example, the compound REX-D14 was obtained in the same manner as the reaction 1, reaction 2 and reaction 3 in example 2, except that the compound Formaldehyde (SM11) in example 2 was replaced by the compound propan-2-one. (5.0% yield).

MS m/z [ESI]: 603.1 [M+1].

79
-continued
80
-continued
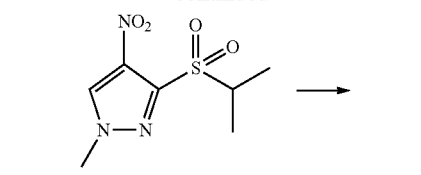
15
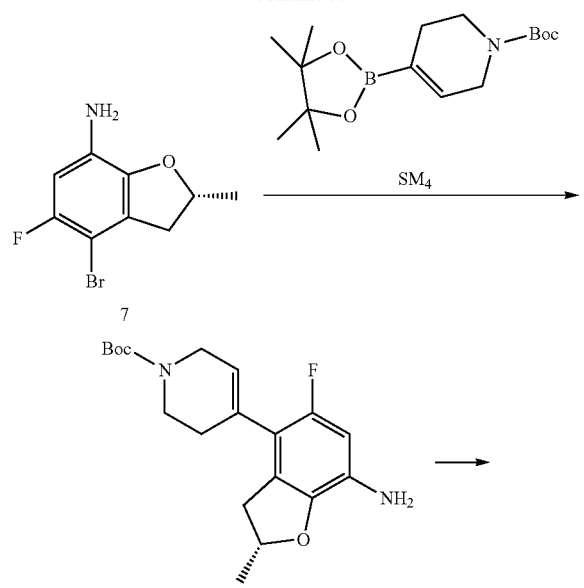
7
8
SM₅
Reaction 2
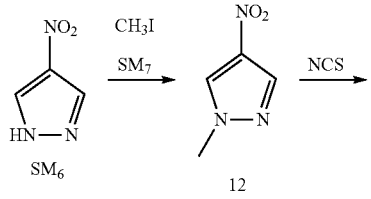
SM₆
12
13
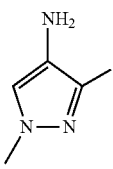
14
16
SM₁₀
Reaction 3
SM₅
+
SM₁₀
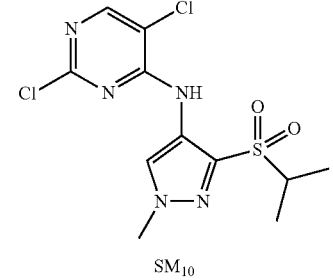
17

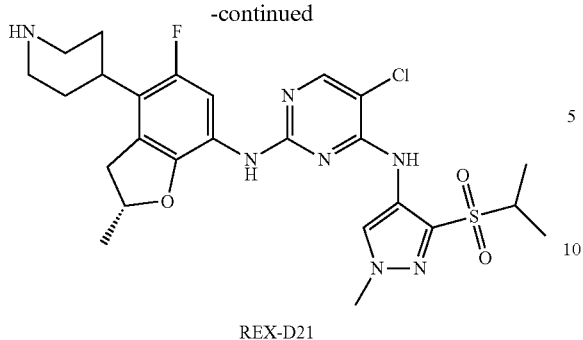

REX-D21

According to synthetic routes as described in this example, the intermediate compound SM5 ((R)-tert-butyl-4-(7-amino-5-fluoro-2-methyl-2,3-dihydrobenzofuran-4-yl)piperidine-1-carboxylate) was obtained in the same manner as the reaction 1 and reaction 2 in example 1, except that the compound 2-bromo-4-methylphenol (SM1) in example 1 was replaced by the compound 2-bromo-4-fluorophenol. (24.0% yield).

According to synthetic routes as described in this example, the compound REX-D21 was obtained in the same synthetic method as in example 1. (6.0% yield).

MS m/z [ESI]: 565.1 [M+1].

$^1$H-NMR (DMSO-$d_6$), δ: 1.23-1.26 (m, 6H), 1.35-1.38 (m, 3H), 1.81-1.84 (m, 2H), 2.13-2.16 (m, 2H), 3.51-3.35 (m, 4H), 3.66-3.67 (m, 2H), 4.02 (S, 3H), 4.92 (s, 2H), 7.33 (s, 1H). 8.19-8.20 (m, 1H), 8.53-8.62 (m, 2H), 8.77-8.79 (m, 1H). 9.12 (S, 1H).

Example 14

5-chloro-N2-(2,6-dimethyl-5-(piperidin-4-yl)chroman-8-yl)-N4-(3-(isopropylsulfonyl)-1-methyl-1H-pyrazol-4-yl)pyrimidine-2,4-diamine [No. REX-D22]

Synthetic Routes:

Reaction 1

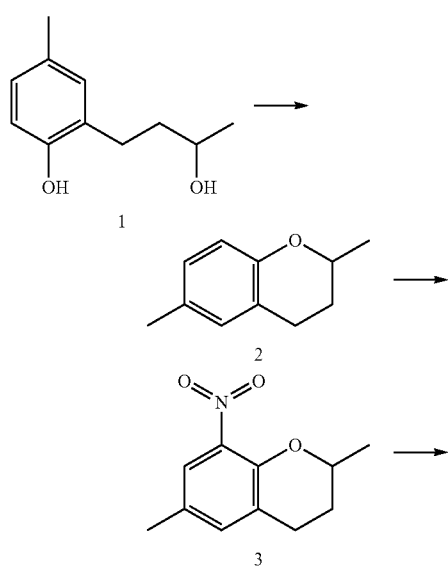

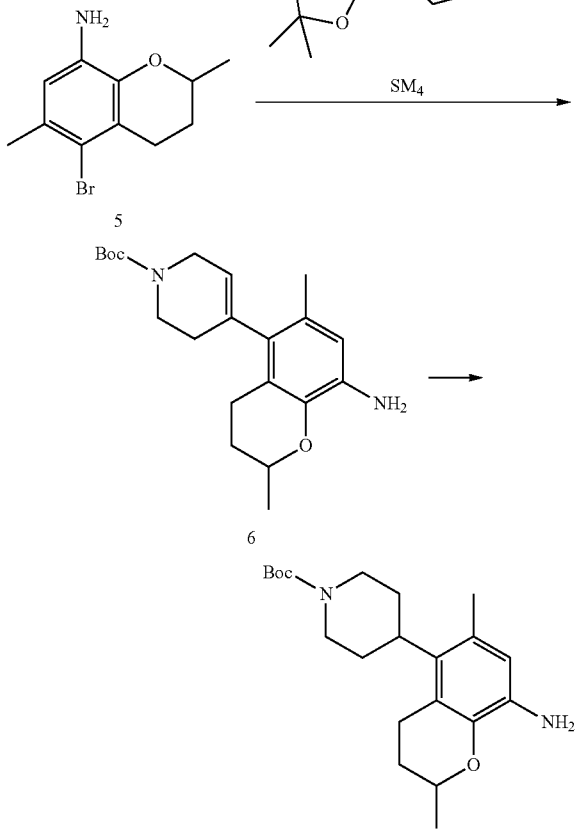

Reaction 2

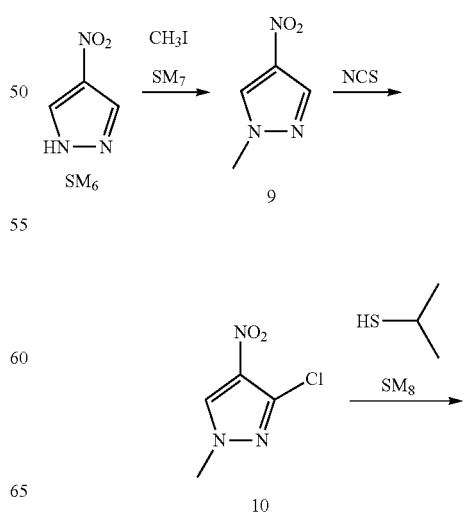

-continued

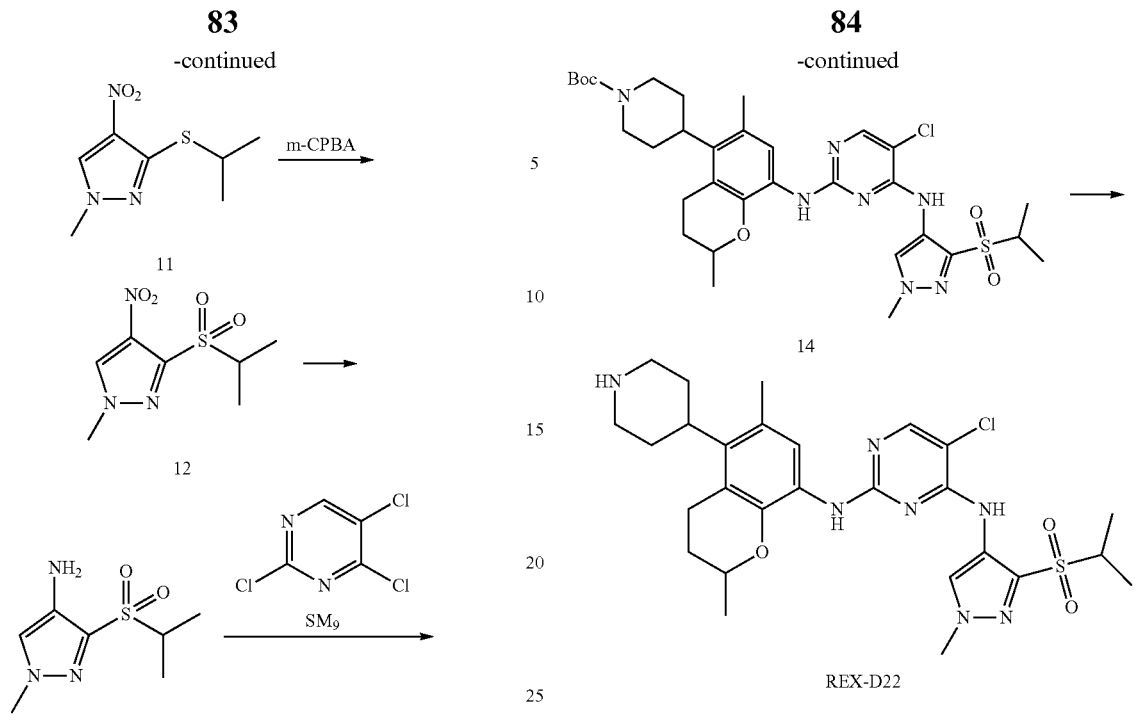

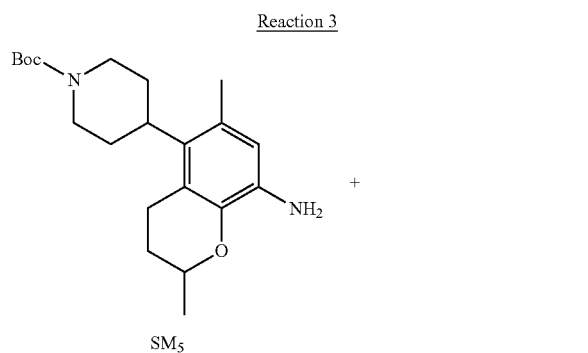

According to synthetic routes as described in this example, the intermediate compound SM5 (tert-butyl-4-(8-amino-2,6-dimethylchroman-5-yl)piperidine-1-carboxylate) was prepared in the same manner as the reaction 1 and reaction 2 in example 1, except that the compound (S)-2-(2-hydroxypropyl)-4-methylphenol (SM3) in example 1 was replaced by the compound 2-(3-hydroxybutyl)-4-methylphenol. (22.0% yield).

According to synthetic routes as described in this example, the compound REX-D22 was obtained in the same synthetic method as in example 1 (3.0% yield).

MS m/z [ESI]: 575.1 [M+1].

$^1$H-NMR (CDCl$_3$), δ: 1.22-1.29 (m, 3H), 1.39-1.43 (m, 6H), 2.06-2.09 (m, 2H), 2.35-2.49 (m, 4H), 3.01-3.05 (m, 2H), 3.20-3.30 (m, 2H), 3.61-3.75 (m, 4H), 4.09 (S, 3H), 7.32 (s, 1H), 8.03 (s, 1H), 9.51-9.81 (m, 2H).

Example 15

(R)-5-chloro-N2-(5-fluoro-2-methyl-4-(1-methylpiperidin-4-yl)-2,3-dihydrobenzofuran-7-yl)-N4-(3-(isopropylsulfonyl)-1-methyl-1H-pyrazol-4-yl)pyrimidine-2,4-diamine [No. REX-D24]

Synthetic Routes:

Reaction 1

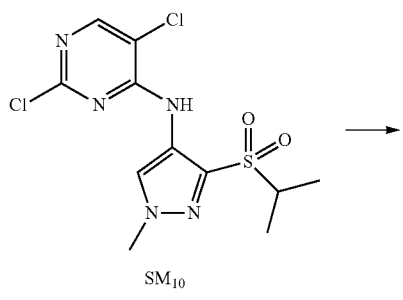

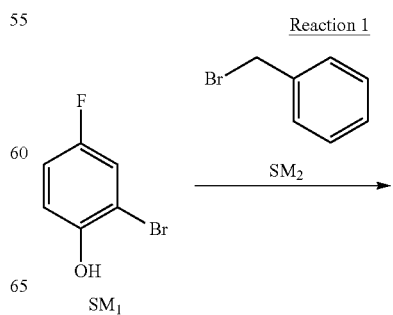

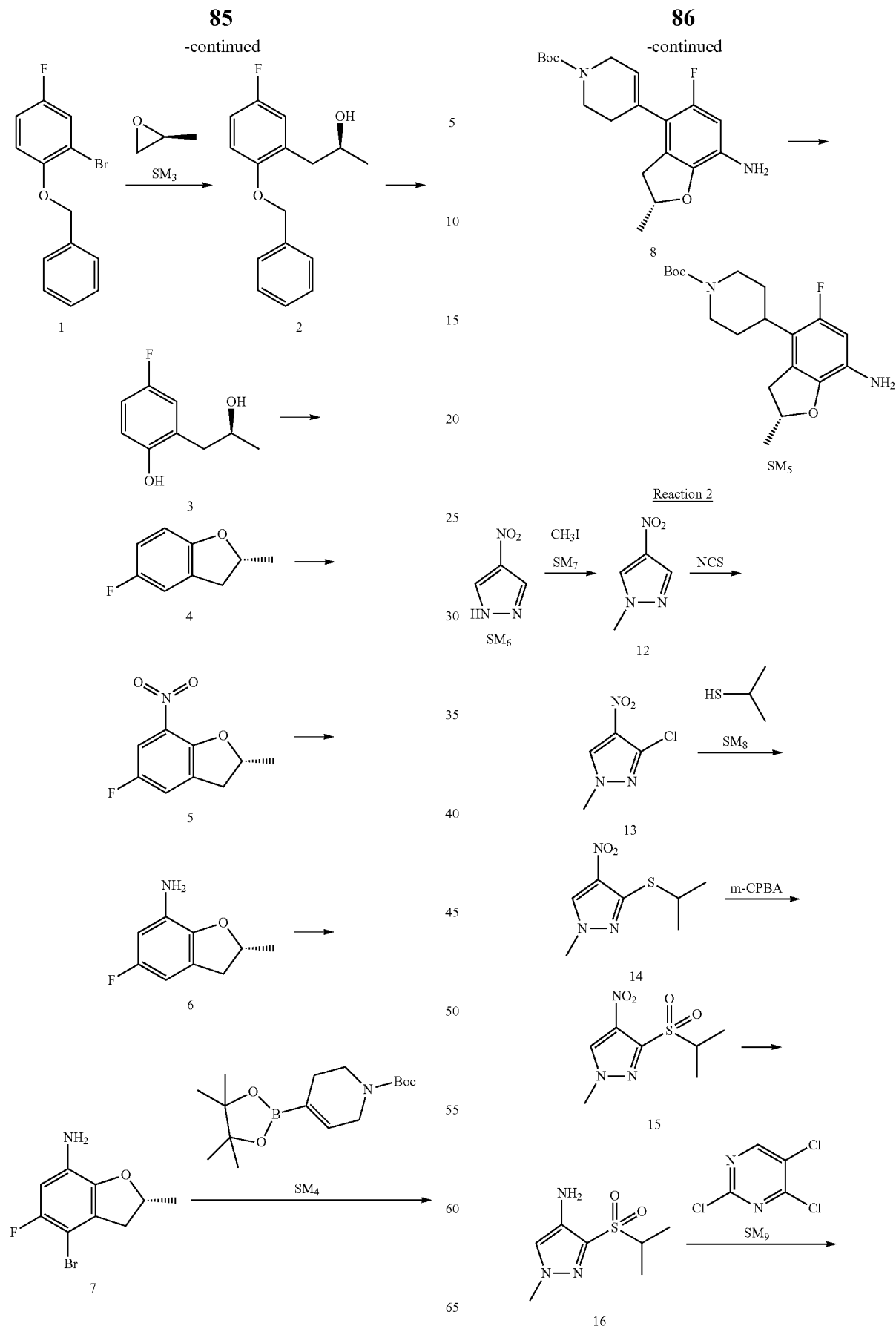

87
-continued

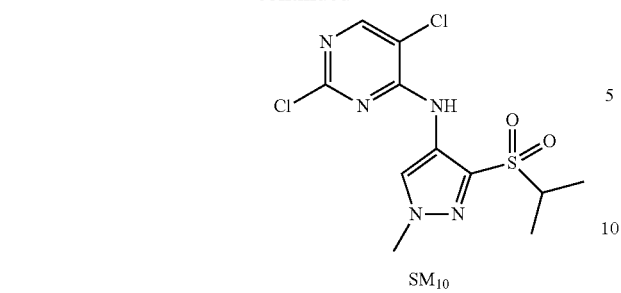

SM₁₀

Reaction 3

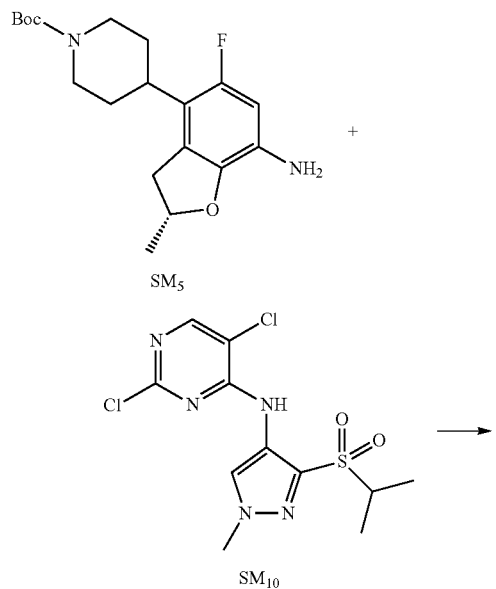

88
-continued

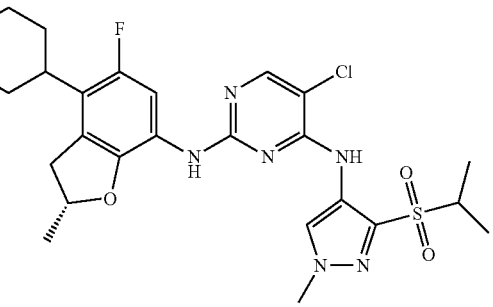

REX-D24

According to synthetic routes as described in this example, the intermediate compound SM5 ((R)-tert-butyl-4-(7-amino-5-fluoro-2-methyl-2,3-dihydrobenzofuran-4-yl)piperidine-1-carboxylate) was prepared in the same manner as the reaction 1 and reaction 2 in example 2, except that the compound 2-Bromo-p-cresol (SM1) in example 2 was replaced by the compound 2-bromo-4-fluorophenol (24.0% yield).

According to synthetic routes as described in this example, the compound REX-D24 was obtained in the same synthetic method as in example 2 (4.0% yield). MS m/z [ESI]: 579.1 [M+1].

Example 16

5-chloro-N2-(2,6-dimethyl-5-(1-methylpiperidin-4-yl)chroman-8-yl)-N4-(3-(isopropylsulfonyl)-1-methyl-1H-pyrazol-4-yl)pyrimidine-2,4-diamine [No. REX-D25]

Synthetic Routes:

Reaction 1

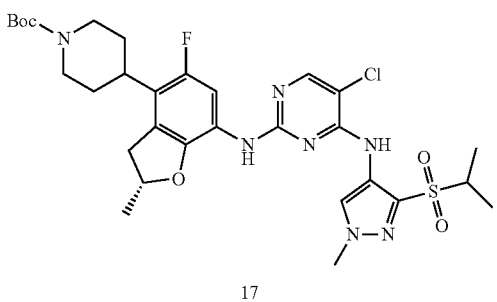

17

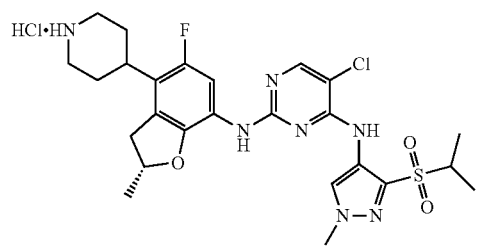

REX-D21

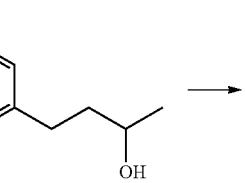

SM₁₁

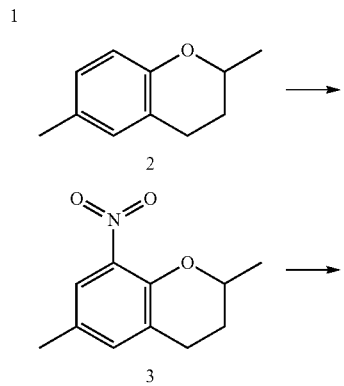

-continued
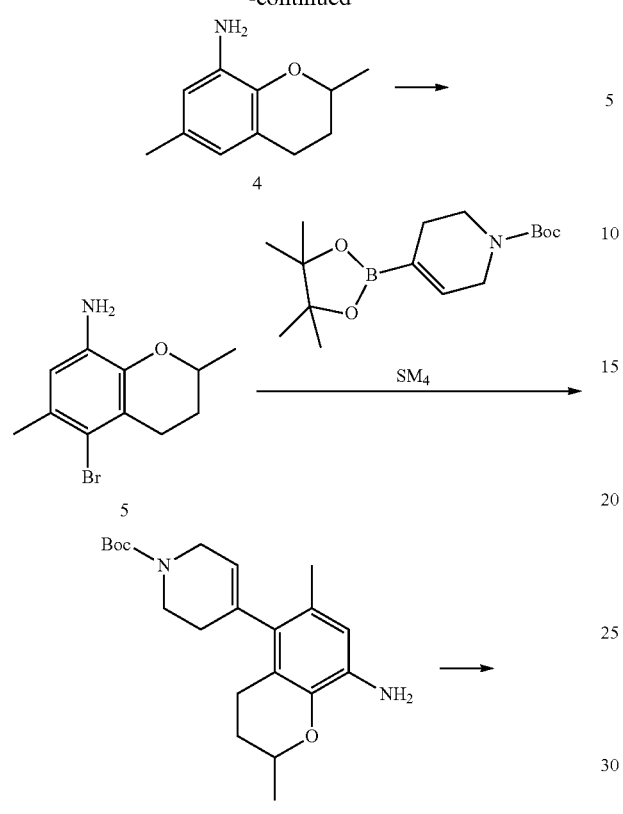
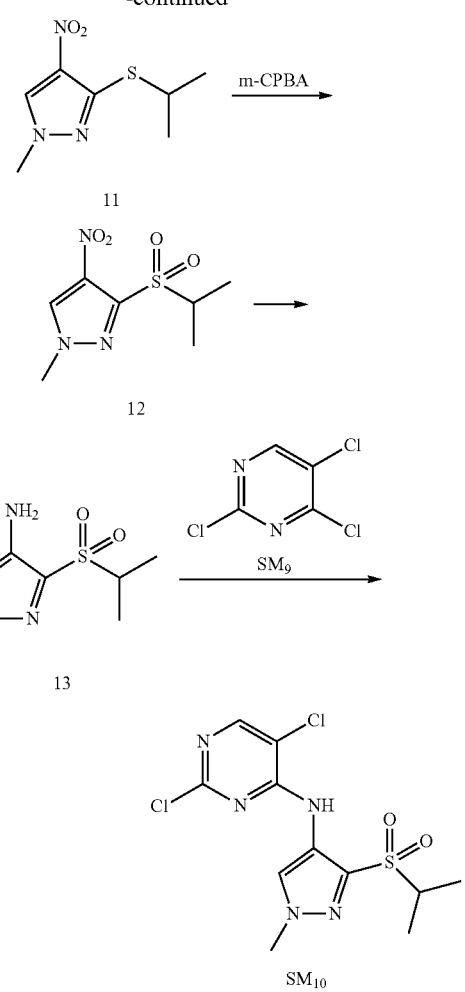
Reaction 2
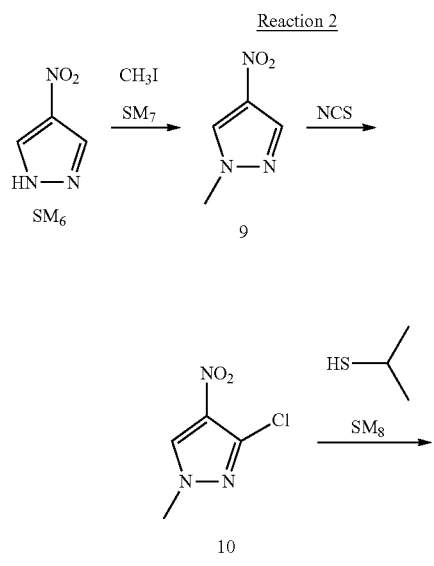
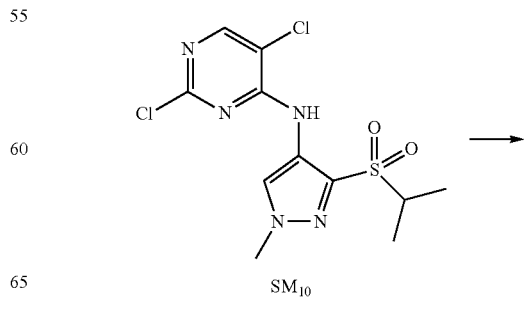

91
-continued

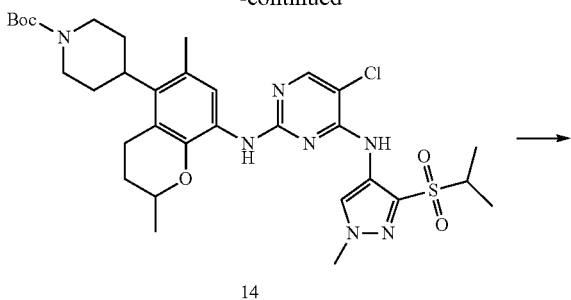

14

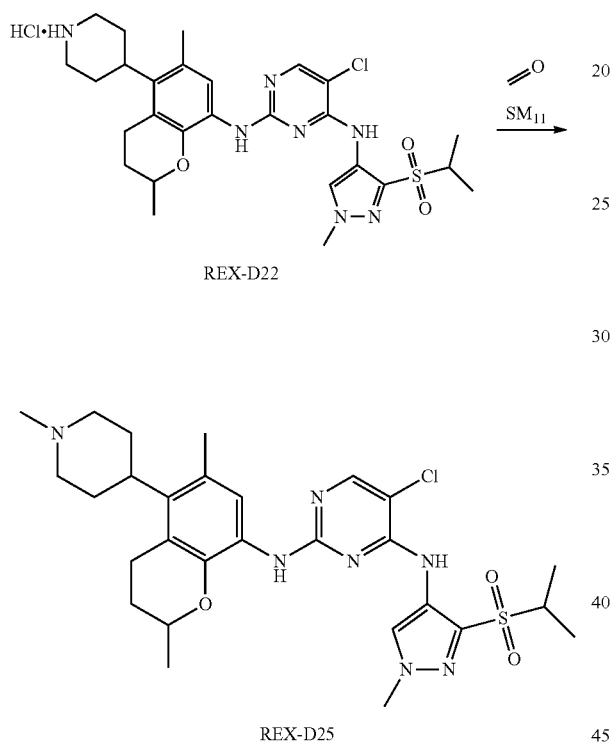

REX-D22

REX-D25

According to synthetic routes as described in this example, the intermediate compound SM5 (tert-butyl-4-(8-amino-2,6-dimethylchroman-5-yl)piperidine-1-carboxylate) was prepared in the same manner as the reaction 1 and reaction 2 in example 2, except that the compound (S)-2-(2-hydroxypropyl)-4-methylphenol (SM3) in example 2 was replaced by the compound 2-(3-hydroxybutyl)-4-methylphenol. (21.0% yield).

According to synthetic routes as described in this example, the compound REX-D25 was obtained in the same synthetic method as in example 2. (2.8% yield).

MS m/z [ESI]: 589.1 [M+1].

92

Example 17

5-chloro-N2-(2,6-dimethyl-5-(1-methylpiperidin-4-yl)chroman-8-yl)-N4-(3-(isopropylsulfonyl)-1-methyl-1H-pyrazol-4-yl)pyrimidine-2,4-diamine
[No. REX-D29]

Synthetic Routes:

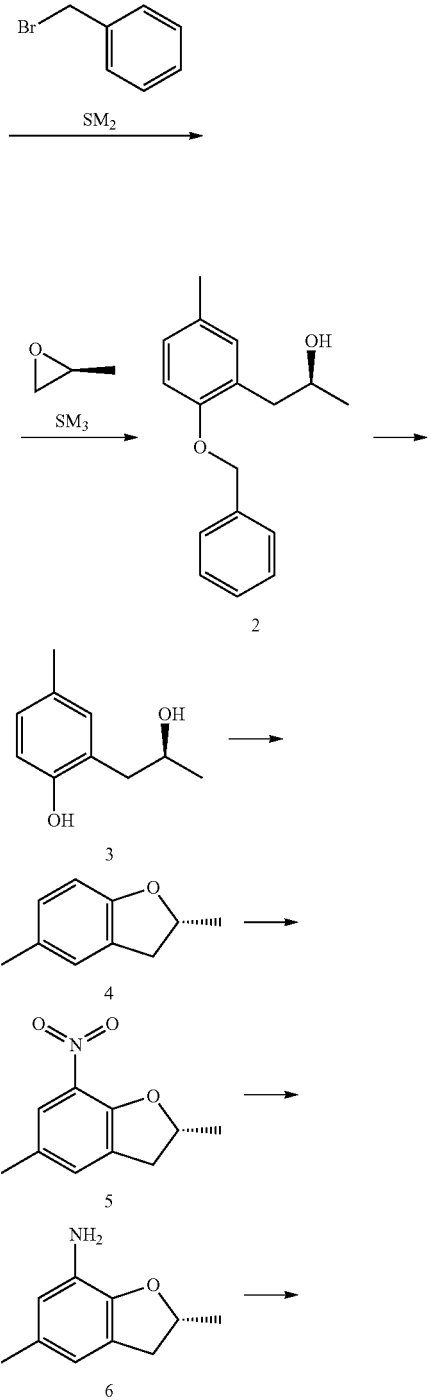

-continued
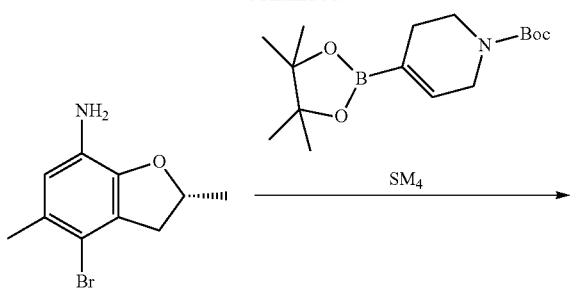
SM4
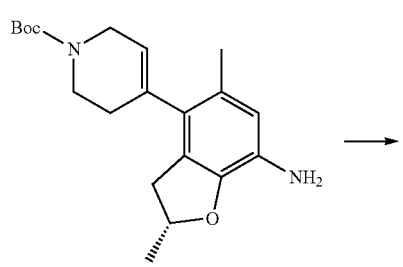
8
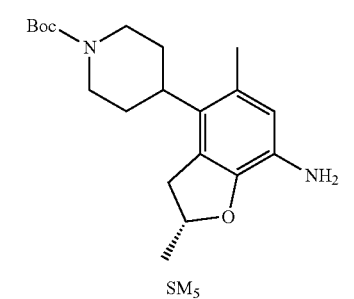
SM5
-continued
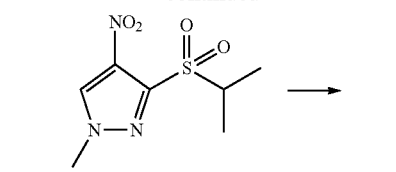
15
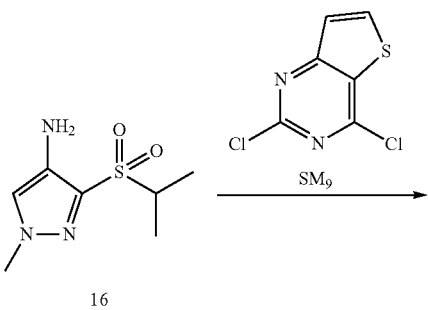
SM9
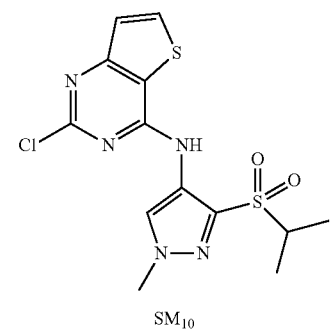
SM10
Reaction 2
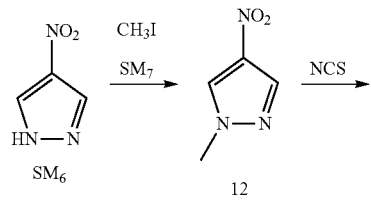
SM6 → 12 → 13 → 14
Reaction 3
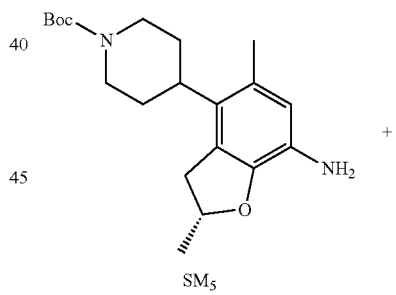
SM5 +
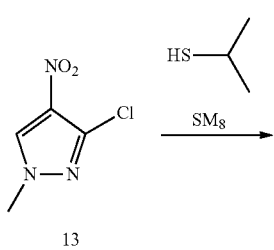
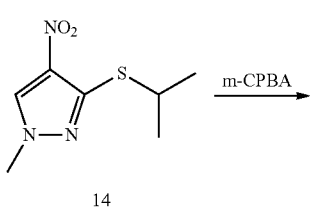
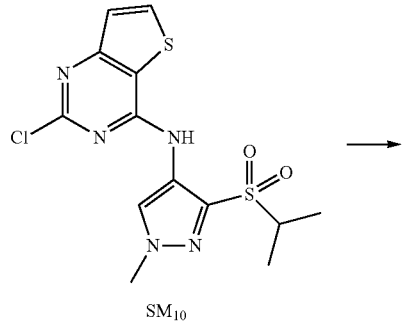
SM10

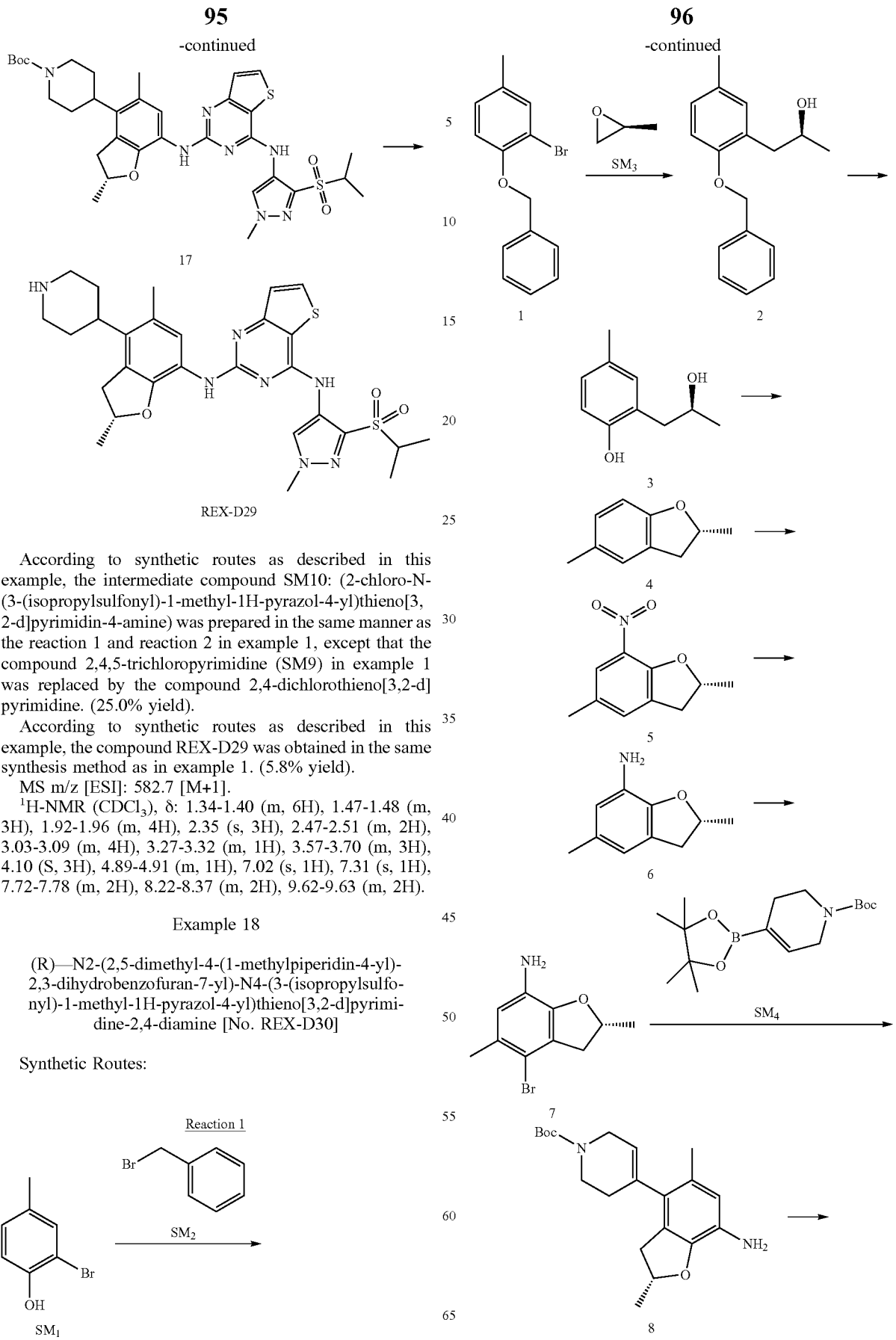

According to synthetic routes as described in this example, the intermediate compound SM10: (2-chloro-N-(3-(isopropylsulfonyl)-1-methyl-1H-pyrazol-4-yl)thieno[3,2-d]pyrimidin-4-amine) was prepared in the same manner as the reaction 1 and reaction 2 in example 1, except that the compound 2,4,5-trichloropyrimidine (SM9) in example 1 was replaced by the compound 2,4-dichlorothieno[3,2-d]pyrimidine. (25.0% yield).

According to synthetic routes as described in this example, the compound REX-D29 was obtained in the same synthesis method as in example 1. (5.8% yield).

MS m/z [ESI]: 582.7 [M+1].

$^1$H-NMR (CDCl$_3$), δ: 1.34-1.40 (m, 6H), 1.47-1.48 (m, 3H), 1.92-1.96 (m, 4H), 2.35 (s, 3H), 2.47-2.51 (m, 2H), 3.03-3.09 (m, 4H), 3.27-3.32 (m, 1H), 3.57-3.70 (m, 3H), 4.10 (S, 3H), 4.89-4.91 (m, 1H), 7.02 (s, 1H), 7.31 (s, 1H), 7.72-7.78 (m, 2H), 8.22-8.37 (m, 2H), 9.62-9.63 (m, 2H).

Example 18

(R)—N2-(2,5-dimethyl-4-(1-methylpiperidin-4-yl)-2,3-dihydrobenzofuran-7-yl)-N4-(3-(isopropylsulfonyl)-1-methyl-1H-pyrazol-4-yl)thieno[3,2-d]pyrimidine-2,4-diamine [No. REX-D30]

Synthetic Routes:

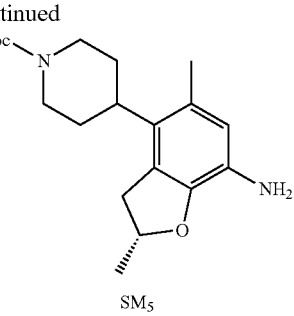
SM5
Reaction 2
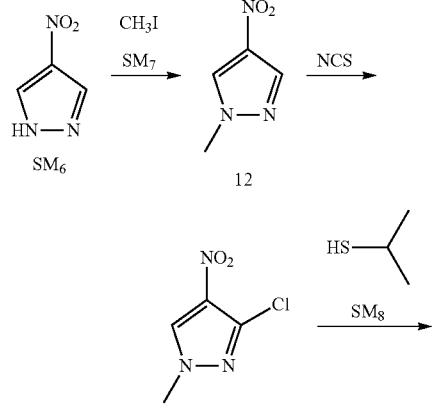
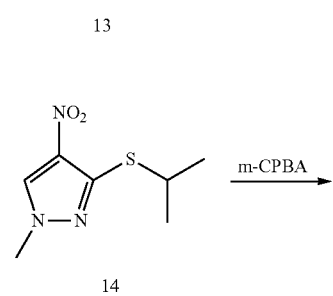
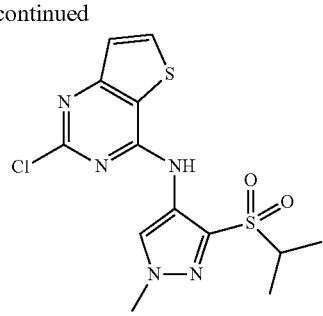
SM10
Reaction 3
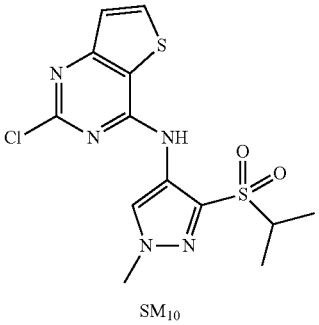
SM5
SM10
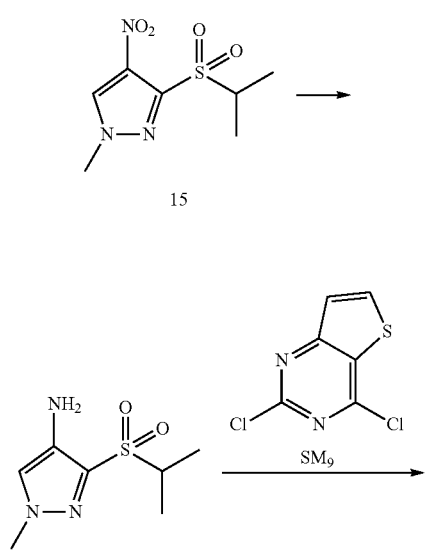
17
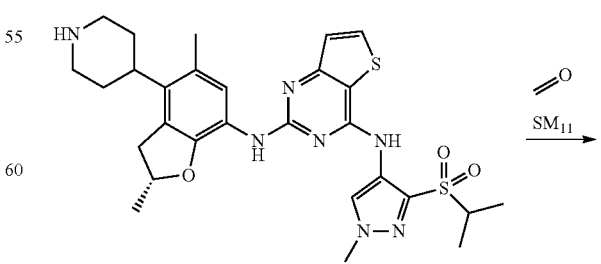
REX-D29

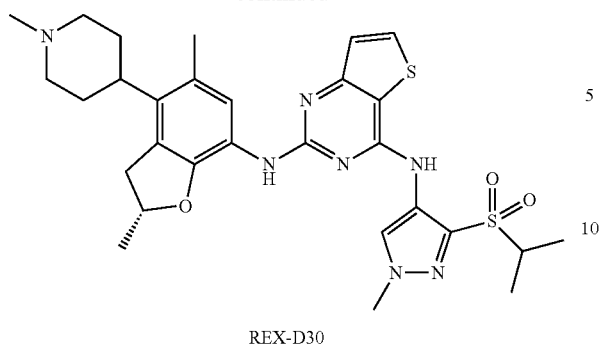

REX-D30

According to synthetic routes as described in this example, the intermediate compound SM10: (2-chloro-N-(3-(isopropylsulfonyl)-1-methyl-1H-pyrazol-4-yl)thieno[3,2-d]pyrimidin-4-amine) was prepared in the same manner as the reaction 1 and reaction 2 in example 2, except that the compound 2,4,5-trichloropyrimidine (SM9) in example 2 was replaced by the compound 2,4-dichlorothieno[3,2-d]pyrimidine. (24.0% yield).

According to synthetic routes as described in this example, the compound REX-D30 was obtained in the same synthesis method as in example 2. (3.5% yield).

MS m/z [ESI]: 596.7 [M+1].

$^1$H-NMR (CDCl$_3$), δ: 1.27-1.29 (m, 6H), 1.34-1.40 (m, 6H), 1.90-2.00 (m, 2H), 2.31-2.35 (m, 4H), 2.85-3.05 (m, 4H), 3.09-3.10 (m, 2H), 3.29-3.30 (m, 1H), 3.49 (S, 3H), 3.67-3.69 (m, 2H), 4.06 (S, 3H), 4.75-4.76 (m, 1H), 7.02 (s, 1H), 7.41 (s, 1H), 7.52-7.53 (m, 1H), 7.85-7.86 (m, 1H), 8.88-8.89 (m, 1H).

Example 19

(R)-5-chloro-N4-(1-cyclopropyl-3-(isopropylsulfonyl)-1H-pyrazol-4-yl)-N2-(2,5-dimethyl-4-(piperidin-4-yl)-2,3-dihydrobenzofuran-7-yl)pyrimidine-2,4-diamine [No. REX-D30]

Synthetic Routes:

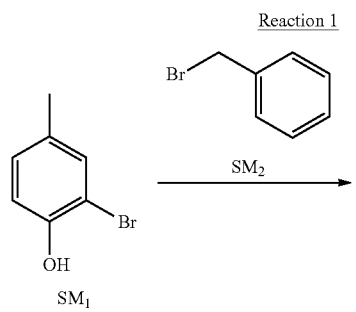

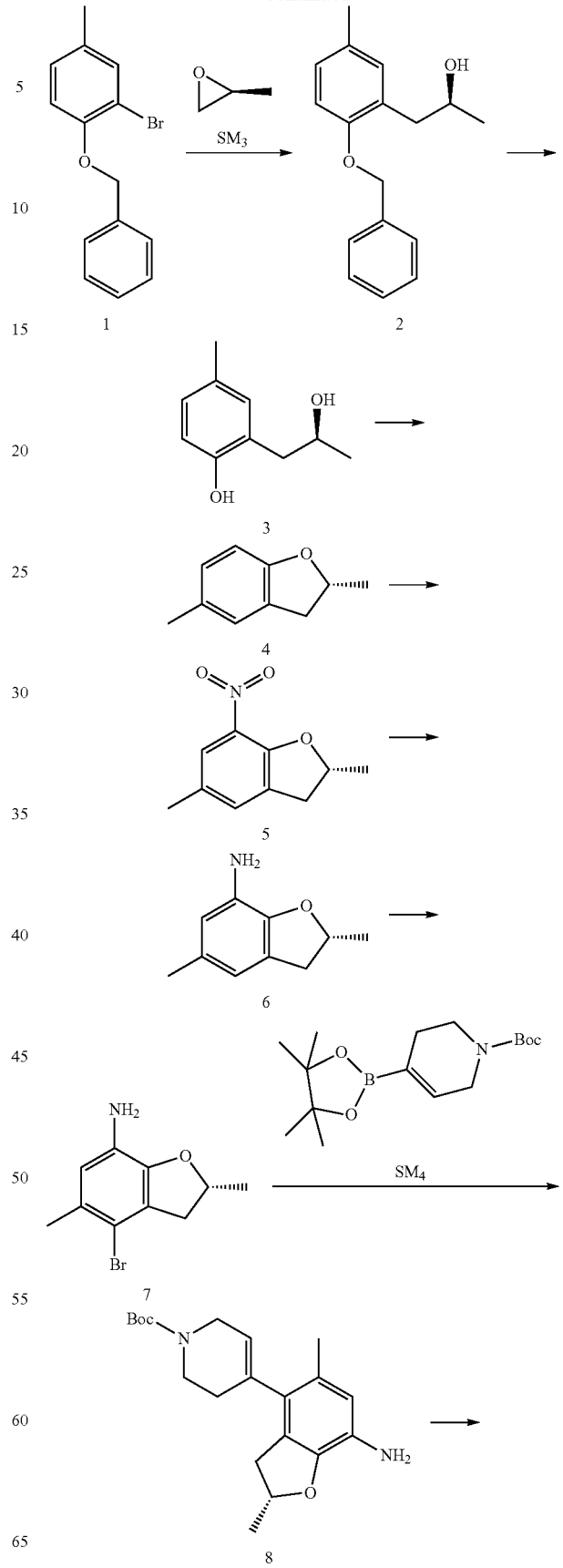

101
-continued
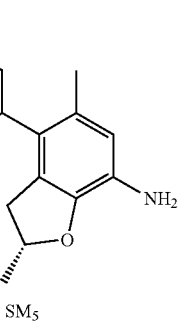
SM₅
Reaction 2
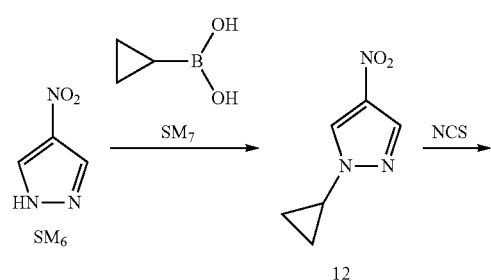
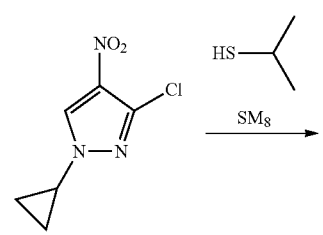
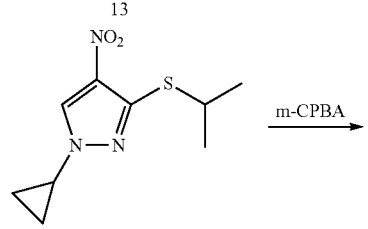
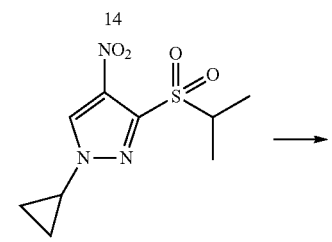
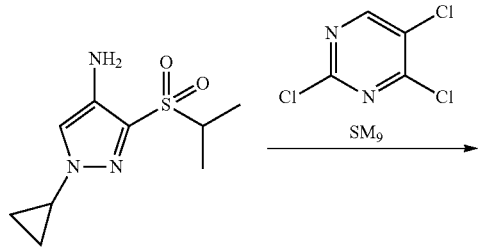
102
-continued
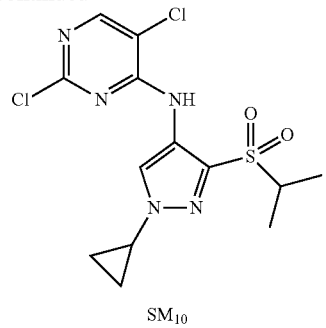
SM₁₀
Reaction 3
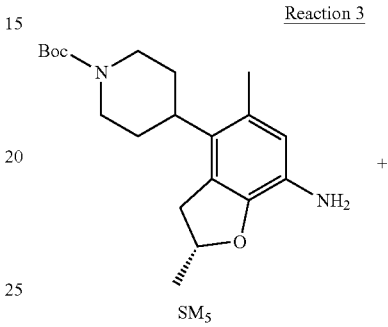
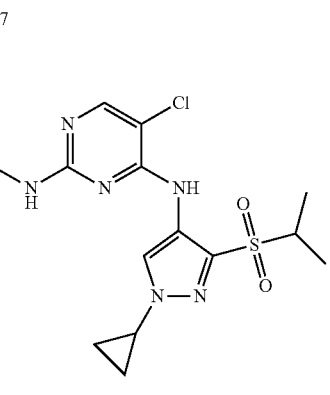
REX-D31

According to synthetic routes as described in this example, the intermediate compound SM10: (2,5-dichloro-N-(1-cyclopropyl-3-(isopropylsulfonyl)-1H-pyrazol-4-yl)pyrimidin-4-amine) was prepared in the same manner as the reaction 1 and reaction 2 in example 1, except that the compound iodomethane (SM7) in example 1 was replaced by the compound cyclopropylboronic acid. (34.0% yield).

According to synthetic routes as described in this example, the compound REX-D31 was obtained in the same synthesis method as in example 1. (3.5% yield).

MS m/z [ESI]: 587.1 [M+1].

$^1$H-NMR DMSO-d$_6$), δ: 1.06-1.08 (m, 2H), 1.21-1.31 (m, 9H), 1.73-1.76 (m, 1H), 2.13-2.15 (m, 1H), 2.26-2.27 (m, 2H), 3.01-3.10 (m, 3H), 3.51-3.52 (m, 1H), 3.69-3.70 (m, 1H), 4.07-4.09 (m, 1H), 4.79-4.81 (m, 1H), 7.08 (s, 1H), 8.12 (s, 1H), 8.58 (s, 1H), 8.77 (s, 1H).

Example 20

(R)-5-chloro-N2-(2,5-dimethyl-4-(piperidin-4-yl)-2,3-dihydrobenzofuran-7-yl)-N4-(1-isopropyl-3-(isopropylsulfonyl)-1H-pyrazol-4-yl)pyrimidine-2,4-diamine [No. REX-D32]

Synthetic Routes:

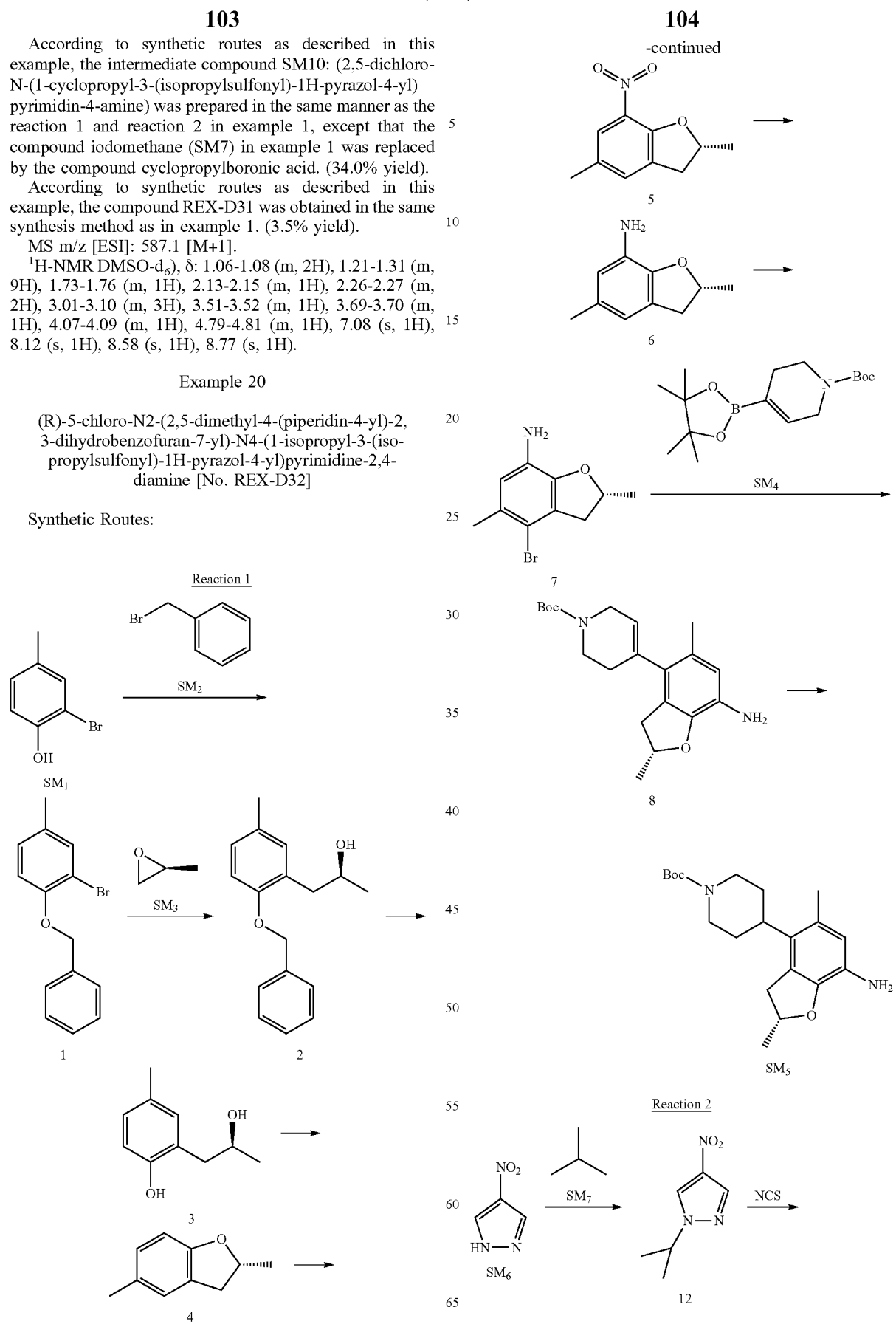

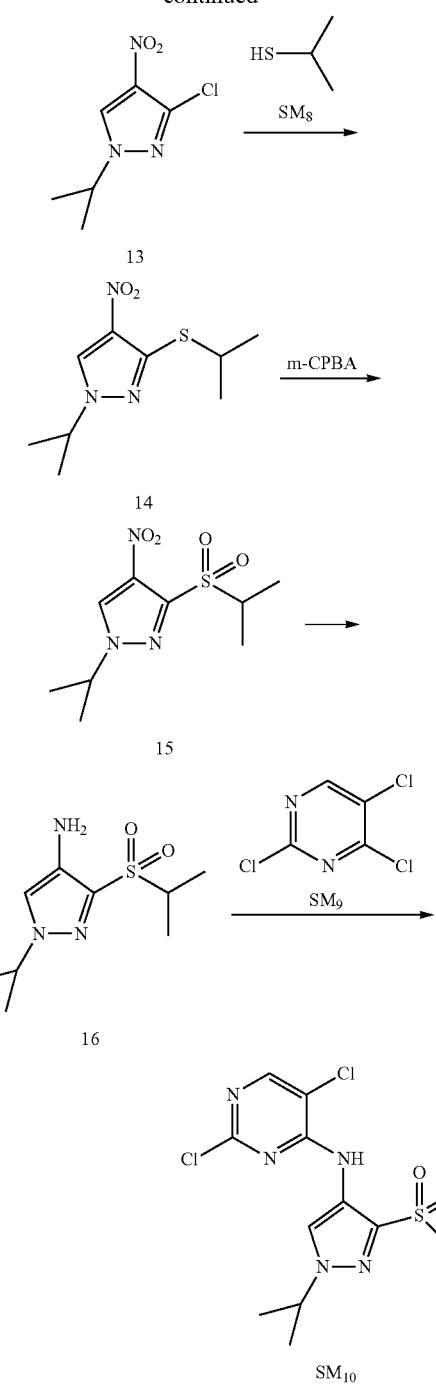

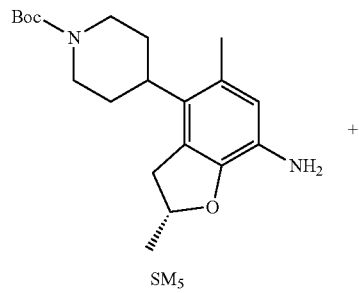

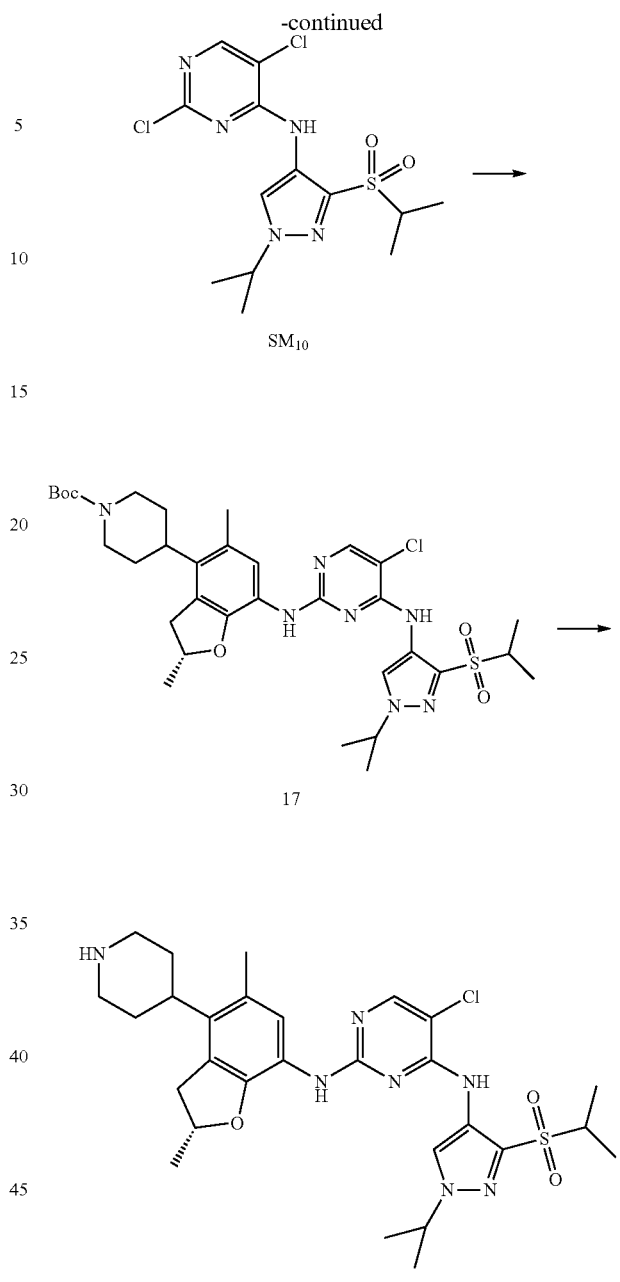

According to synthetic routes as described in this example, the intermediate compound SM10: (2,5-dichloro-N-(1-isopropyl-3-(isopropylsulfonyl)-1H-pyrazol-4-yl)pyrimidin-4-amine) was prepared in the same manner as the reaction 1 and reaction 2 in example 1, except that the compound iodomethane (SM7) in example 1 was replaced by the compound 2-iodopropane (24.0% yield).

According to synthetic routes as described in this example, the compound REX-D32 was obtained in the same synthesis method as in example 1. (5.5% yield).

MS m/z [ESI]: 589.1 [M+1].

$^1$H-NMR DMSO-$d_6$), δ: 1.21-1.27 (m, 9H), 1.40-1.42 (m, 6H), 1.71-1.74 (m, 2H), 2.26-2.30 (m, 5H), 3.11-3.16 (m, 3H), 3.17-3.18 (m, 1H), 3.42-3.53 (m, 4H), 4.79-4.81 (m, 1H), 4.97-4.98 (m, 1H), 7.04 (s, 1H), 8.26 (s, 1H), 8.98 (s, 1H).

Example 21
(R)-5-chloro-N2-(2,5-dimethyl-4-(piperidin-4-yl)-2,3-dihydrobenzofuran-7-yl)-N4-(1-ethyl-3-(isopropylsulfonyl)-1H-pyrazol-4-yl)pyrimidine-2,4-diamine [No. REX-D33]
Synthetic Routes:
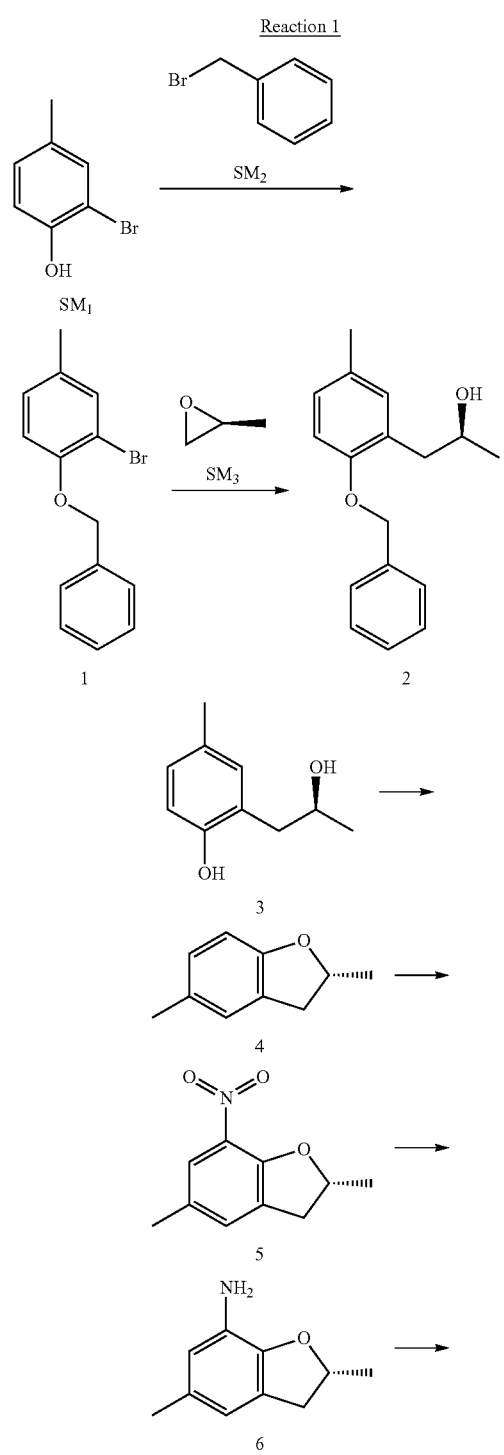
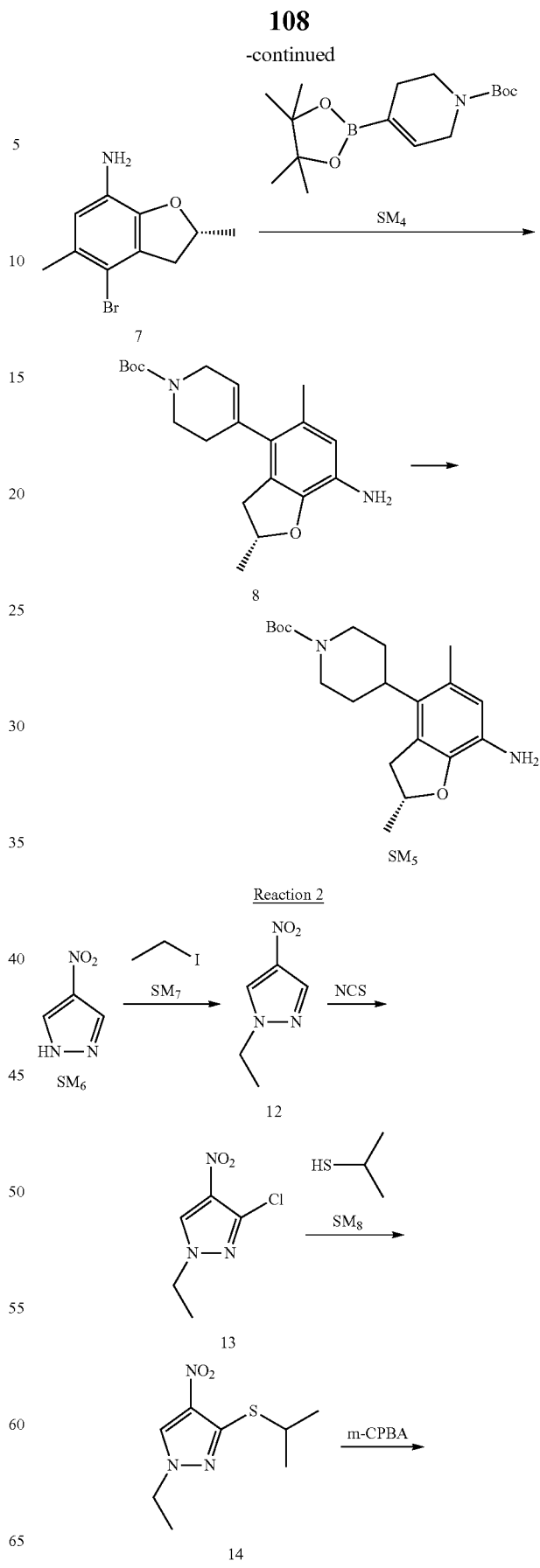

-continued

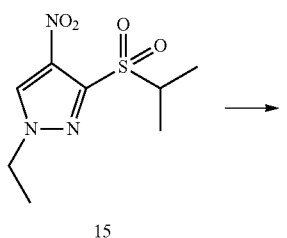

15

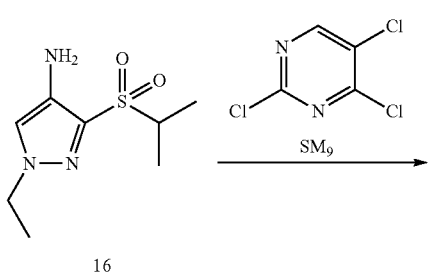

16

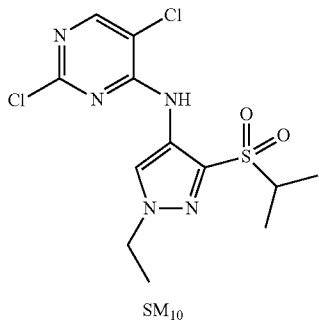

SM₁₀

Reaction 3

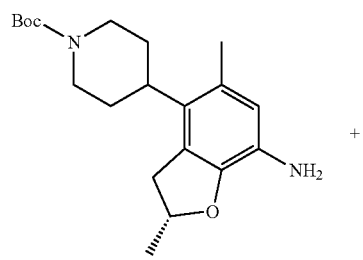

SM₅

+

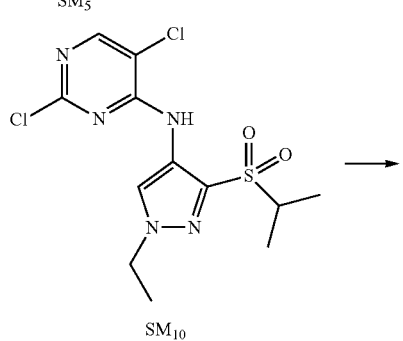

SM₁₀

-continued

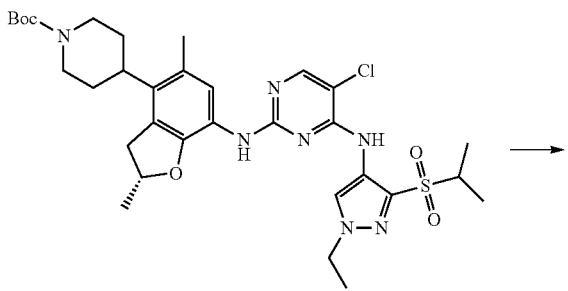

17

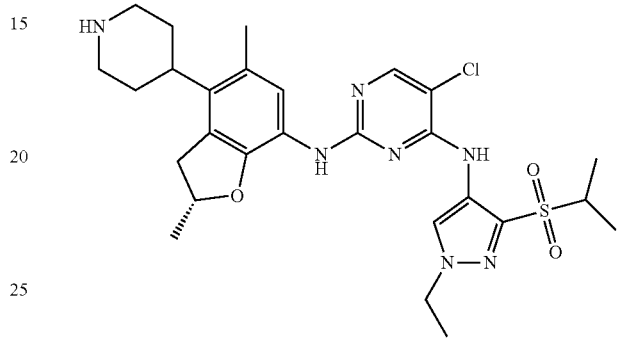

REX-D33

According to synthetic routes as described in this example, the intermediate compound SM10: (2,5-dichloro-N-(1-ethyl-3-(isopropylsulfonyl)-1H-pyrazol-4-yl)pyrimidin-4-amine) was prepared in the same manner as the reaction 1 and reaction 2 in example 1, except that the compound iodomethane (SM7) in example 1 was replaced by the compound iodoethane. (27.0% yield).

According to synthetic routes as described in this example, the compound REX-D33 was obtained in the same synthesis method as in example 1. (4.5% yield). MS m/z [ESI]: 575.1 [M+1].

Example 22

(R)-5-chloro-N4-(1-cyclopropyl-3-(isopropylsulfonyl)-1H-pyrazol-4-yl)-N2-(2,5-dimethyl-4-(1-methylpiperidin-4-yl)-2,3-dihydrobenzofuran-7-yl)pyrimidine-2,4-diamine [No. REX-D34]

Synthetic Routes:

Reaction 1

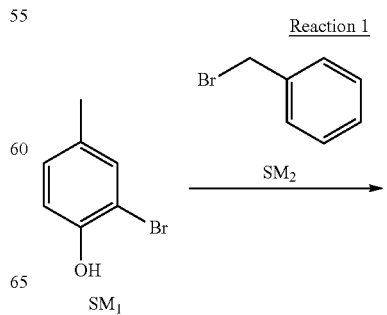

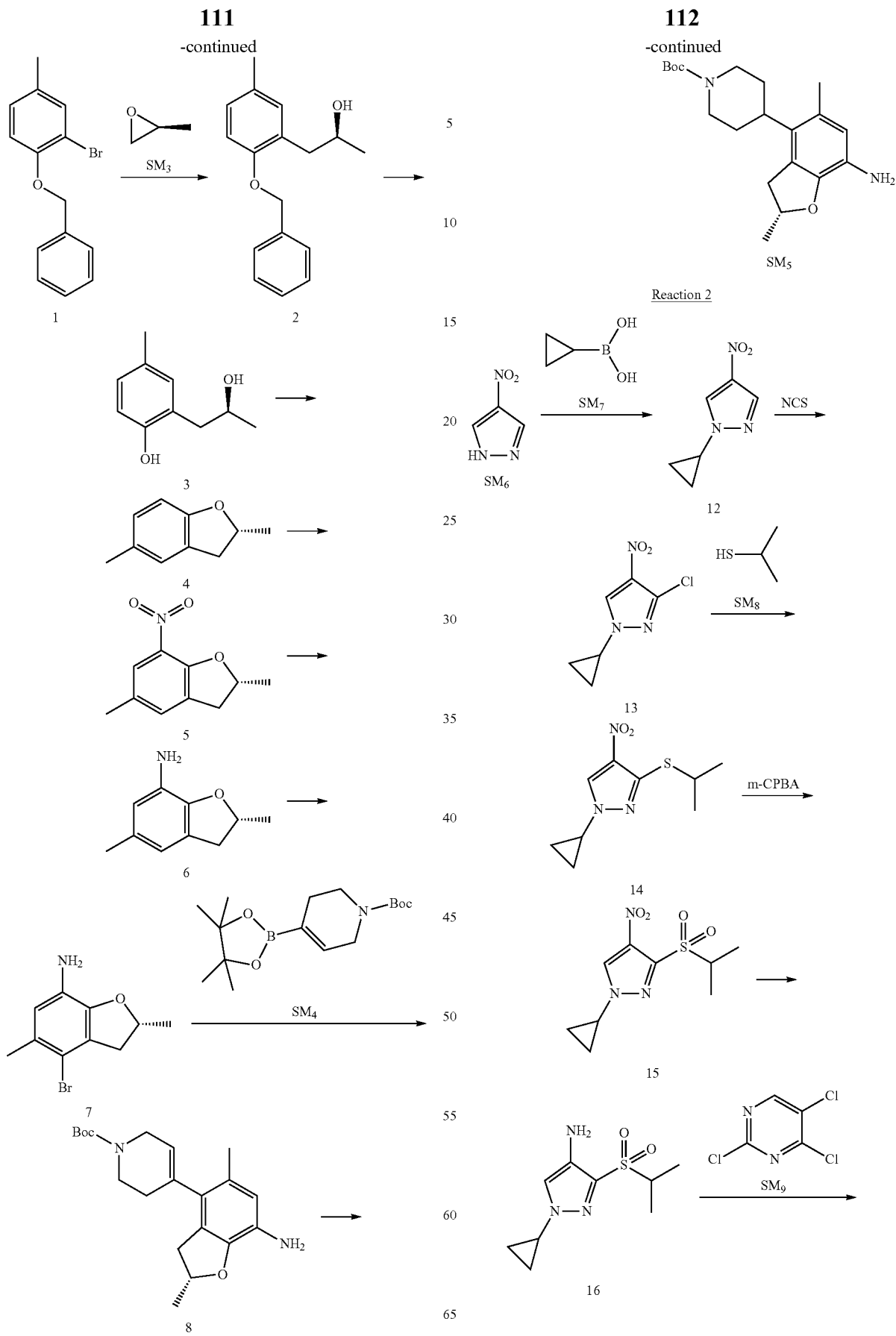

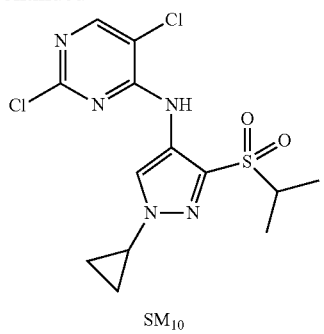

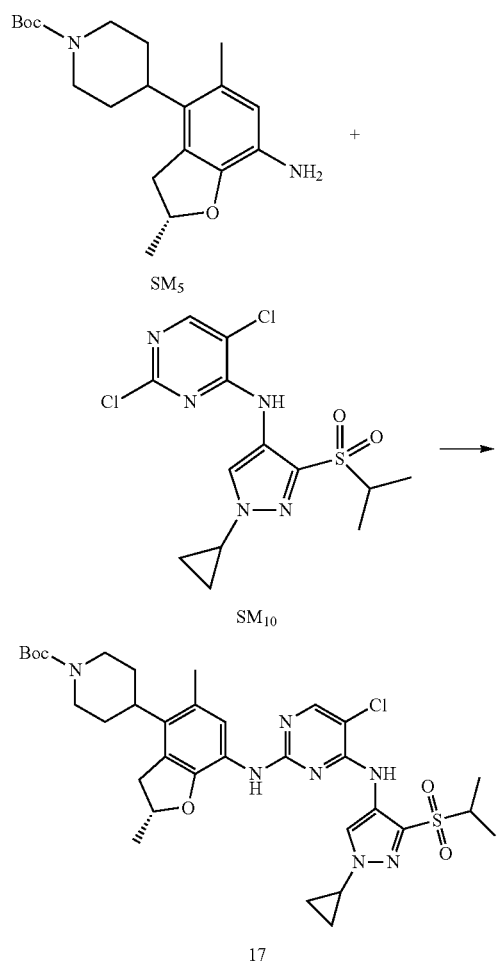

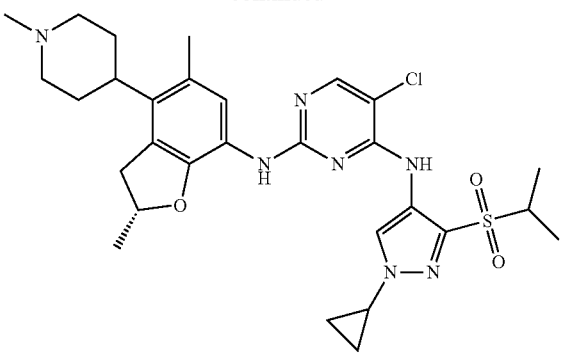

According to synthetic routes as described in this example, the intermediate compound SM10: (2,5-dichloro-N-(1-cyclopropyl-3-(isopropylsulfonyl)-1H-pyrazol-4-yl)pyrimidin-4-amine) was prepared in the same manner as the reaction 1 and reaction 2 in example 2, except that the compound iodomethane (SM7) in example 2 was replaced by the compound cyclopropylboronic acid. (34.0% yield).

According to synthetic routes as described in this example, the compound REX-D34 was obtained in the same synthesis method as in example 2. (4.5% yield).

MS m/z [ESI]: 600.1 [M+1].

$^1$H-NMR DMSO-$d_6$), δ: 1.06-1.08 (m, 2H), 1.19-1.24 (m, 10H), 1.76-1.79 (m, 2H), 2.26 (s, 3H), 2.73-2.74 (m, 2H), 2.93-3.04 (m, 3H), 3.49-3.52 (m, 1H), 3.68-3.71 (m, 1H), 4.06-4.09 (m, 1H), 4.77-4.81 (m, 1H), 7.08 (s, 1H), 8.12 (s, 1H), 8.58 (s, 1H), 8.78 (s, 1H).

Example 23

(R)-5-chloro-N2-(2,5-dimethyl-4-(1-methylpiperidin-4-yl)-2,3-dihydrobenzofuran-7-yl)-N4-(1-isopropyl-3-(isopropylsulfonyl)-1H-pyrazol-4-yl)pyrimidine-2,4-diamine [No. REX-D35]

Synthetic Routes:

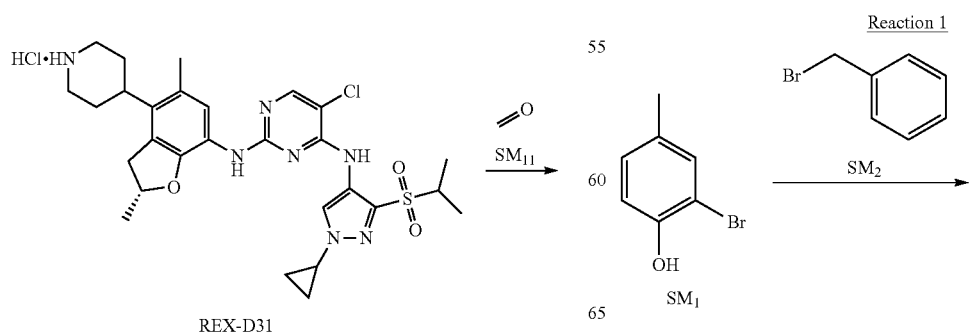

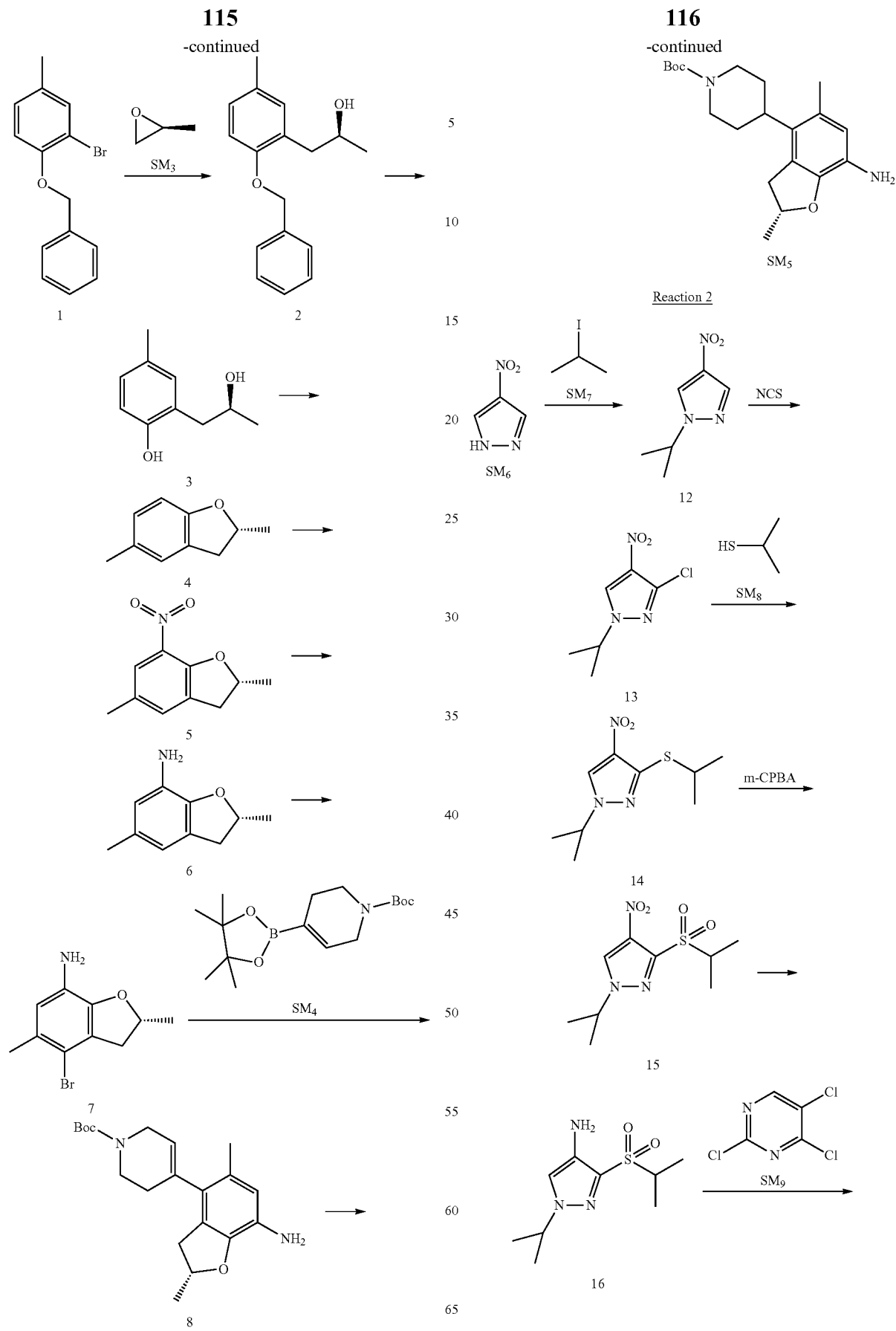

117
-continued

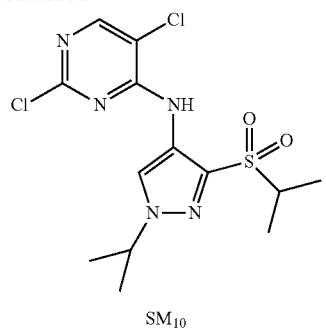

SM10

Reaction 3

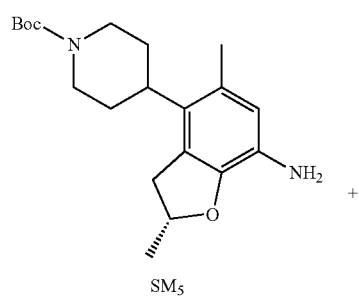

SM5

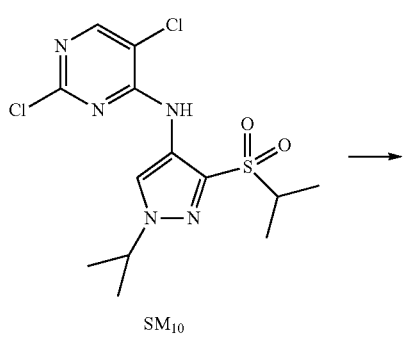

SM10

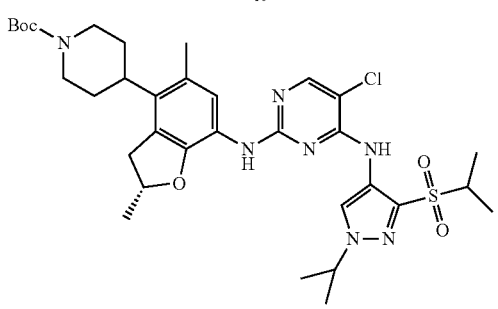

17

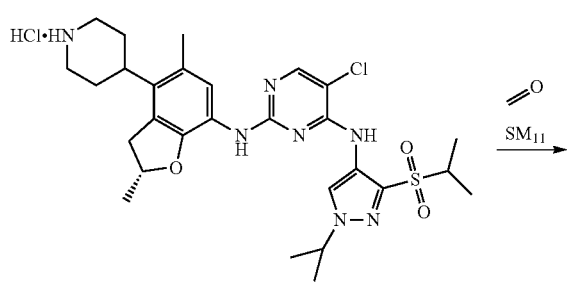

REX-D32

118
-continued

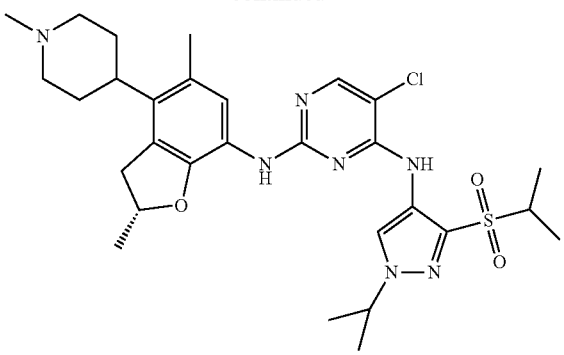

REX-D35

According to synthetic routes as described in this example, the intermediate compound SM10: (2,5-dichloro-N-(1-isopropyl-3-(isopropylsulfonyl)-1H-pyrazol-4-yl)pyrimidin-4-amine) was prepared in the same manner as the reaction 1 and reaction 2 in example 2, except that the compound iodomethane (SM7) in example 2 was replaced by the compound 2-iodopropane (22.0% yield).

According to synthetic routes as described in this example, the compound REX-D35 was obtained in the same synthesis method as in example 2. (4.8% yield). MS m/z [ESI]: 602.1 [M+1].

$^1$H-NMR DMSO-$d_6$), δ: 1.23-1.27 (m, 9H), 1.41-1.42 (m, 6H), 1.76-1.79 (m, 2H), 2.26-2.30 (m, 4H), 2.69-2.70 (m, 3H), 2.92-3.03 (m, 3H), 3.48-3.52 (m, 1H), 3.58-3.61 (m, 1H), 4.77-4.79 (m, 1H), 4.97-4.98 (m, 1H), 7.09 (s, 1H), 8.12 (s, 1H), 8.54 (s, 1H), 8.75 (s, 1H).

Example 24

(R)-5-chloro-N2-(2,5-dimethyl-4-(1-methylpiperidin-4-yl)-2,3-dihydrobenzofuran-7-yl)-N4-(1-ethyl-3-(isopropylsulfonyl)-1H-pyrazol-4-yl)pyrimidine-2,4-diamine [No. REX-D36]

Synthetic Routes:

Reaction 1

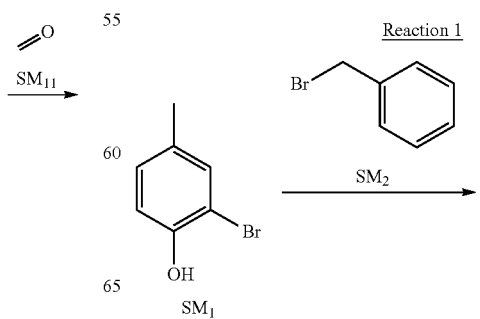

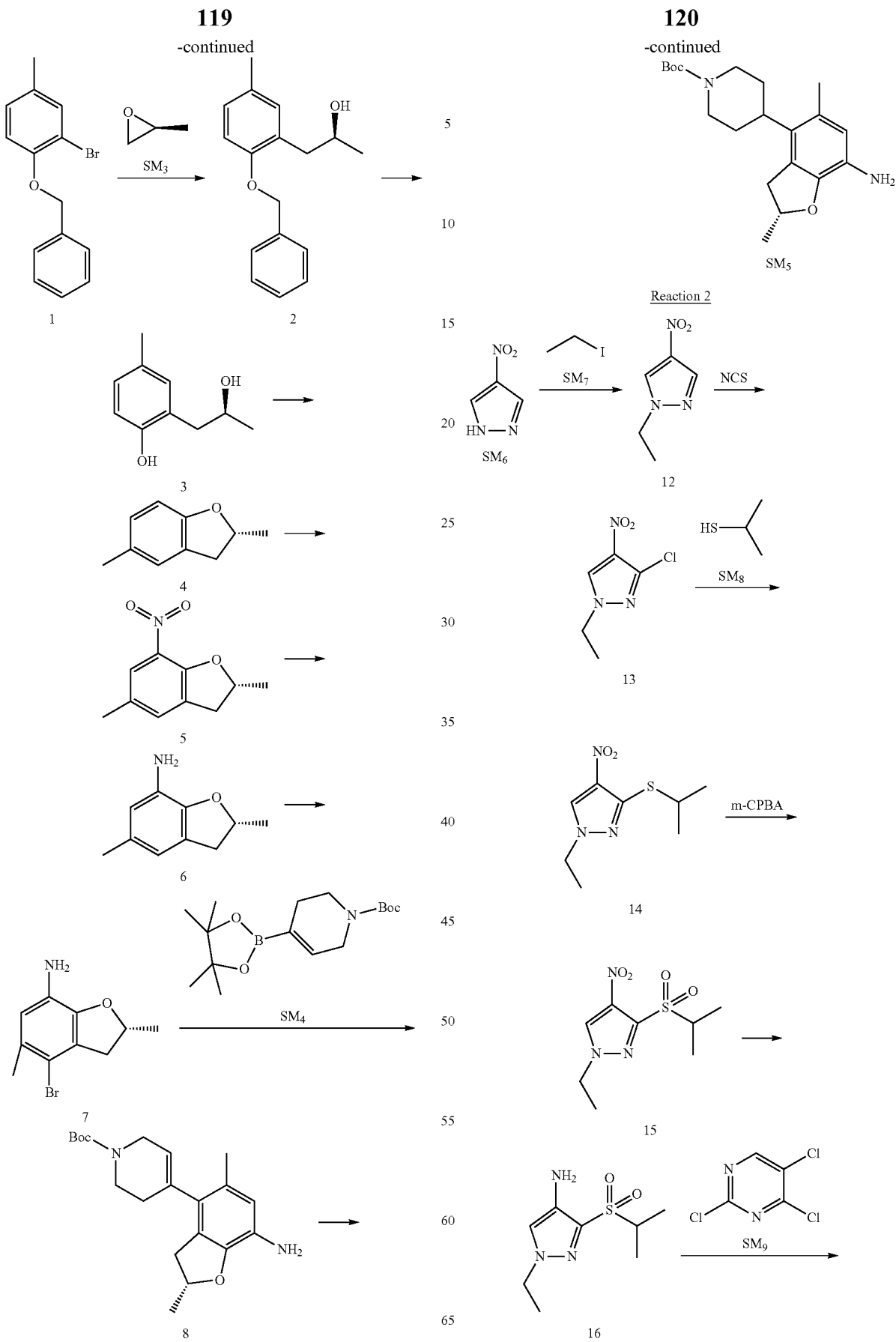

121
-continued

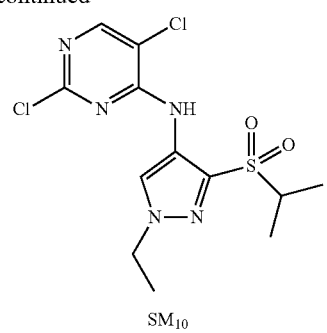

SM₁₀

Reaction 3

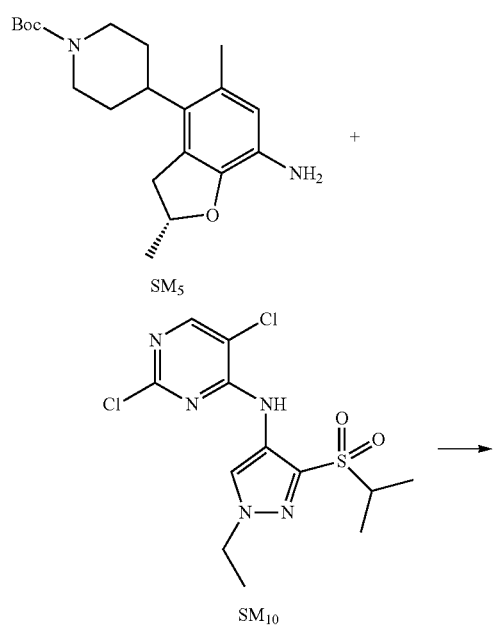

122
-continued

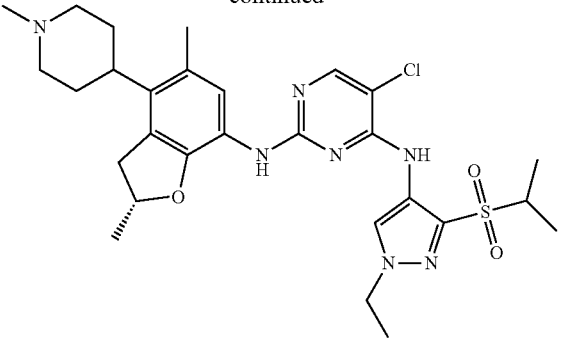

REX-D36

According to synthetic routes as described in this example, the intermediate compound SM10: (2,5-dichloro-N-(1-ethyl-3-(isopropylsulfonyl)-1H-pyrazol-4-yl)pyrimidin-4-amine) was prepared in the same manner as the reaction 1 and reaction 2 in example 2, except that the compound iodomethane (SM7) in example 1 was replaced by the compound iodoethane. (27.0% yield).

According to synthetic routes as described in this example, the compound REX-D36 was obtained in the same synthesis method as in example 1. (4.0% yield).

MS m/z [ESI]: 588.1 [M+1].

Example 25

(R)-5-chloro-N2-(2,5-dimethyl-4-(piperidin-4-yl)-2,3-dihydrobenzofuran-7-yl)-N4-(3-(isobutylsulfonyl)-1-methyl-1H-pyrazol-4-yl)pyrimidine-2,4-diamine [No. REX-D37]

Synthetic Routes:

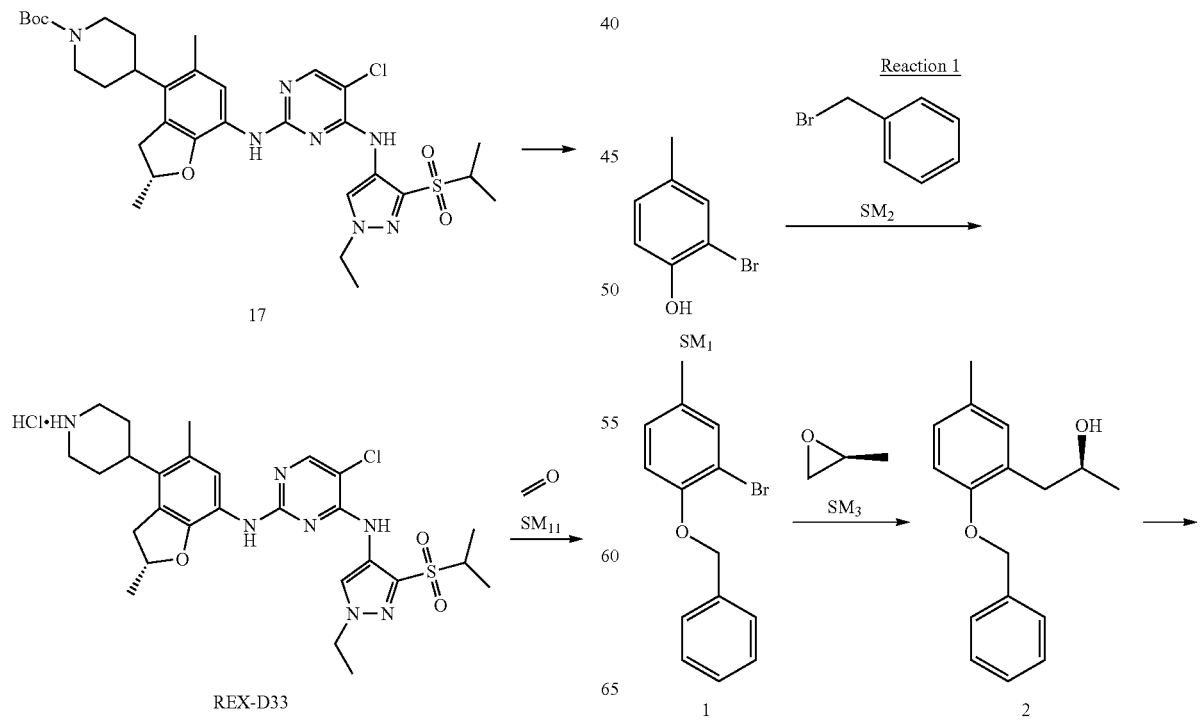

123
-continued
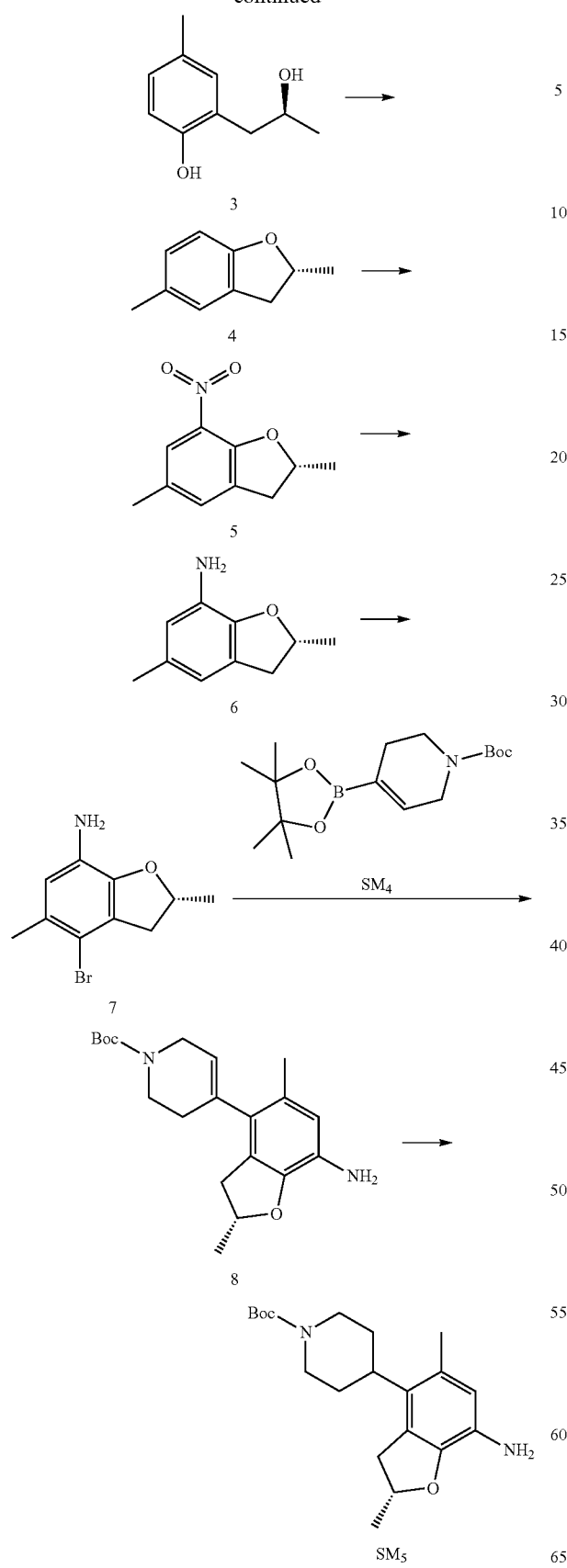
124
-continued
Reaction 2
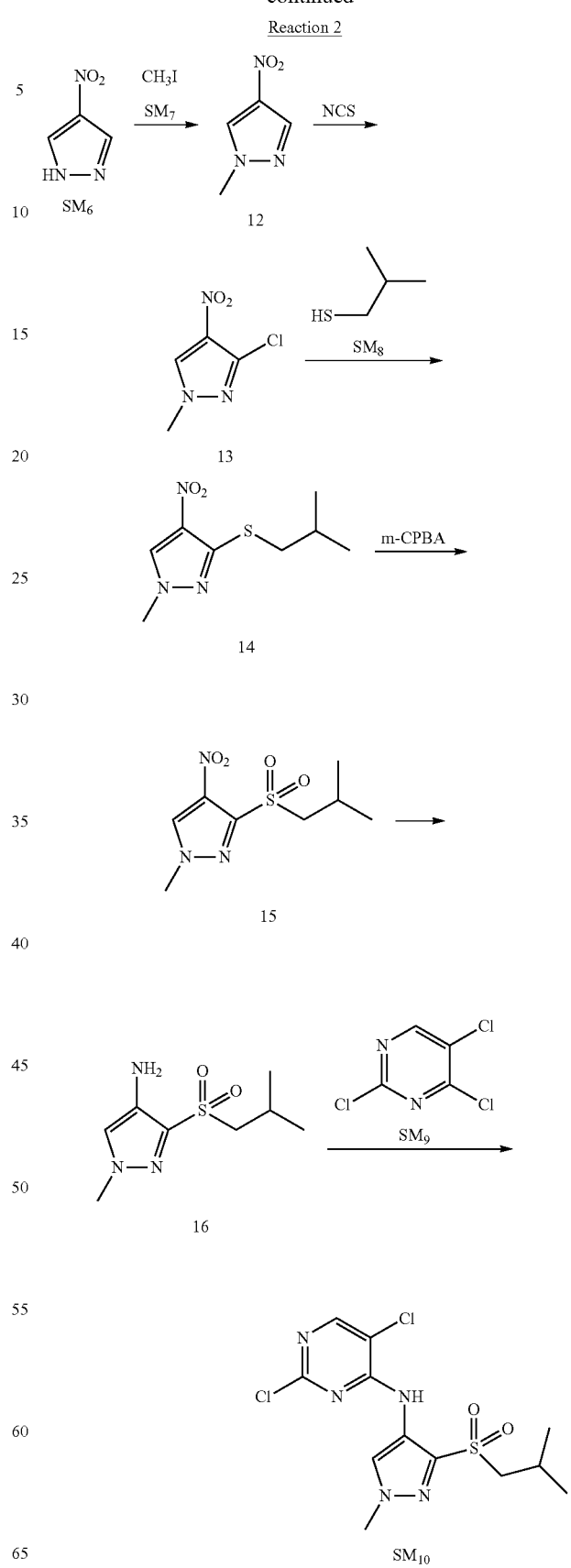

125
-continued

Reaction 3

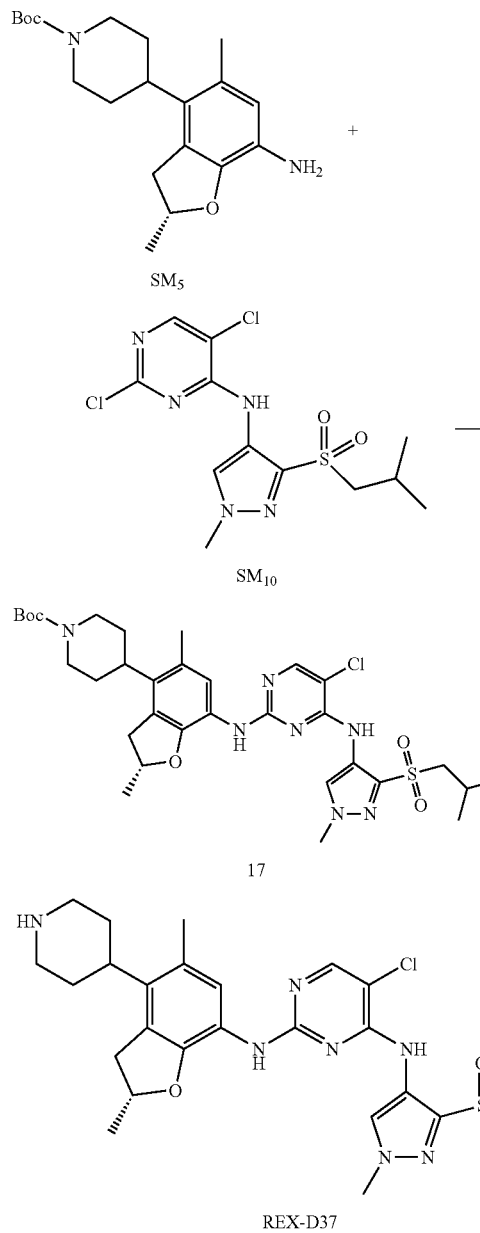

According to synthetic routes as described in this example, the intermediate compound SM10: (2,5-dichloro-N-(3-(isobutylsulfonyl)-1-methyl-1H-pyrazol-4-yl)pyrimidin-4-amine) was prepared in the same manner as the reaction 1 and reaction 2 in example 1, except that the compound propane-2-thiol (SM8) in example 1 was replaced by the compound 2-methylpropane-1-thiol (25.0% yield).

According to synthetic routes as described in this example, the compound REX-D37 was obtained in the same synthesis method as in example 1. (4.3% yield).

MS m/z [ESI]: 575.1 [M+1].

126

Example 26

(R)-5-chloro-N2-(2,5-dimethyl-4-(1-methylpiperidin-4-yl)-2,3-dihydrobenzofuran-7-yl)-N4-((isobutylsulfonyl)-1-methyl-1H-pyrazol-4-yl)pyrimidine-2,4-diamine [No. REX-D38]

Synthetic Routes:

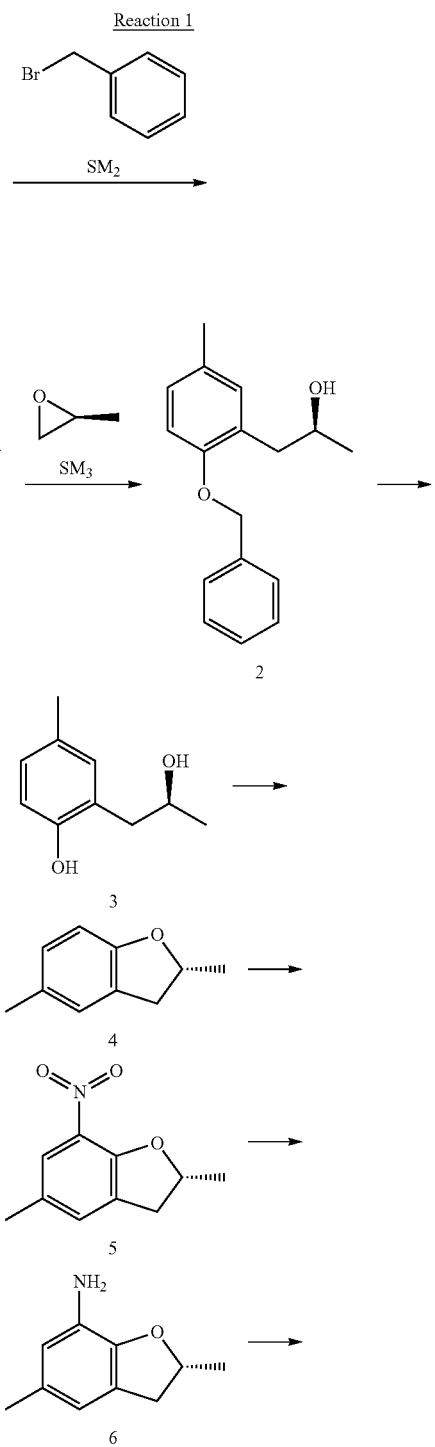

127
-continued
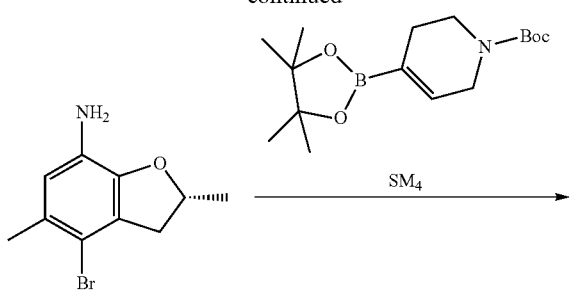
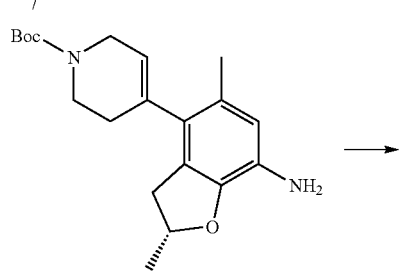
Reaction 2
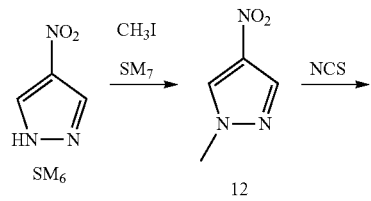
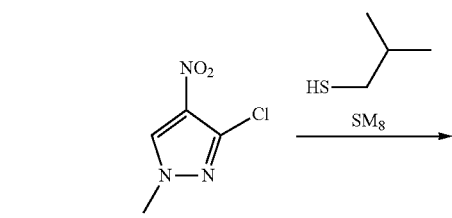
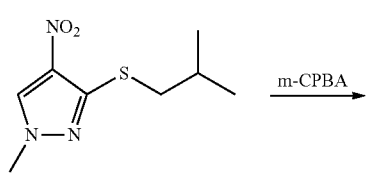
128
-continued
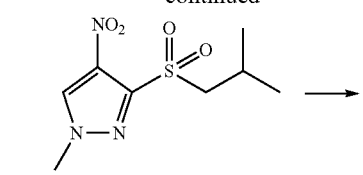
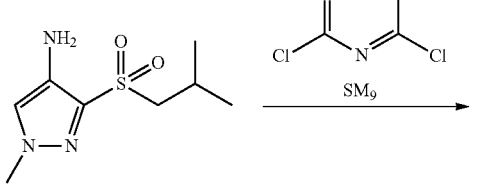
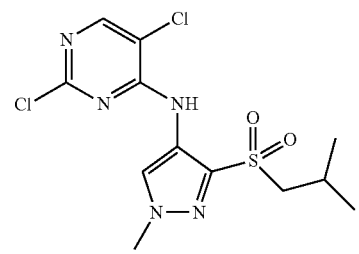
Reaction 3
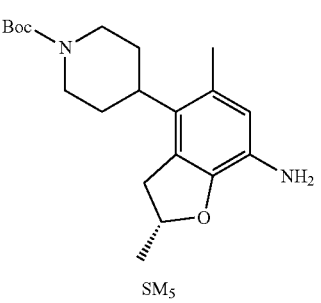
+
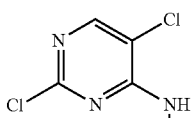
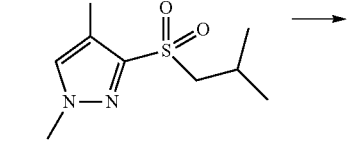
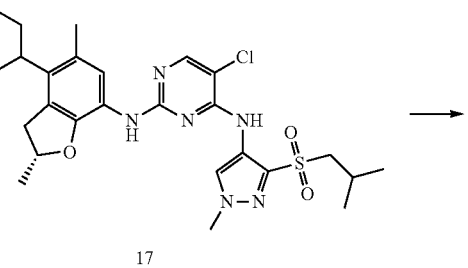

-continued

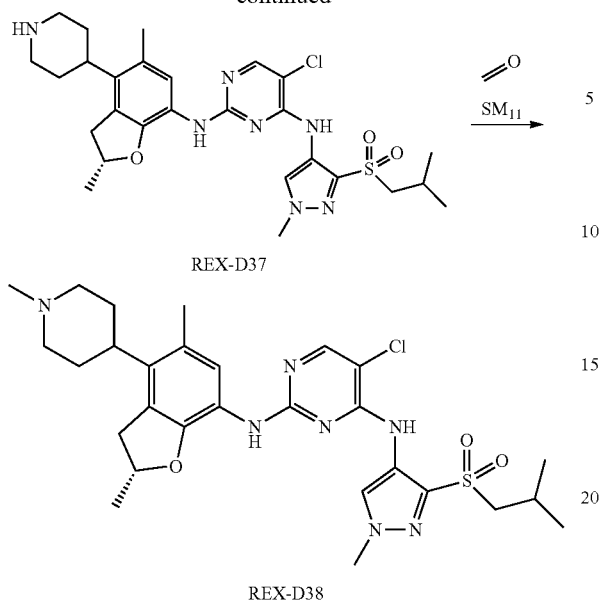

According to synthetic routes as described in this example, the intermediate compound SM10: (2,5-dichloro-N-(3-(isobutylsulfonyl)-1-methyl-1H-pyrazol-4-yl)pyrimidin-4-amine) was prepared in the same manner as reaction 1 and reaction 2 in example 2, except that the compound propane-2-thiol (SM8) in example 2 was replaced by the compound 2-methylpropane-1-thiol. (24.0% yield).

According to synthetic routes as described in this example, the compound REX-D38 was obtained in the same synthesis method as in example 2. (4.6% yield). MS m/z [ESI]: 589.1 [M+1].

$^1$H-NMR DMSO-$d_6$), δ: 0.97-0.99 (m, 6H), 1.31-1.32 (m, 3H), 1.72-1.75 (m, 2H), 2.03-2.05 (m, 1H), 2.24-2.25 (m, 4H), 2.66-2.67 (m, 2H), 2.97-3.00 (m, 3H), 3.45-3.53 (m, 5H), 4.01 (m, 3H), 4.79-4.80 (m, 1H), 7.05 (s, 1H), 8.08 (s, 1H), 8.57 (s, 1H), 8.73 (s, 1H).

Example 27

(R)-2-(4-(7-((5-chloro-4-((3-(isobutylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanol [No. REX-D39]

Synthetic Routes:

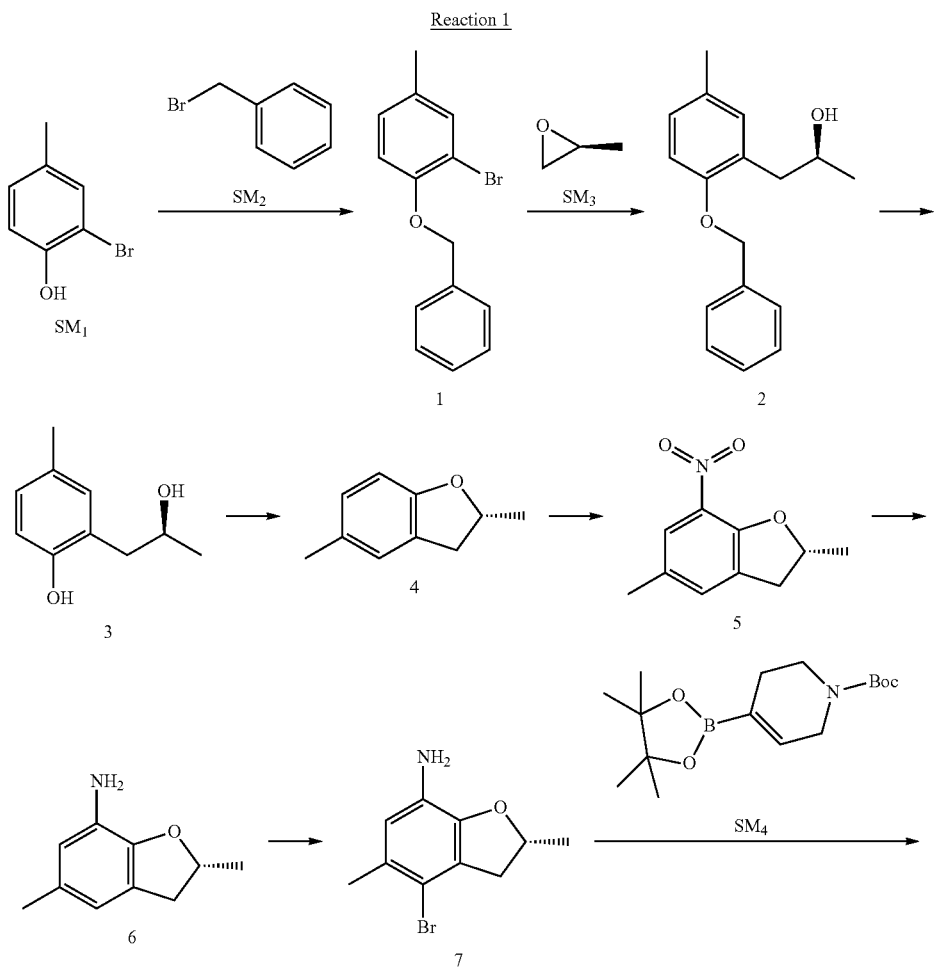

131
132
-continued
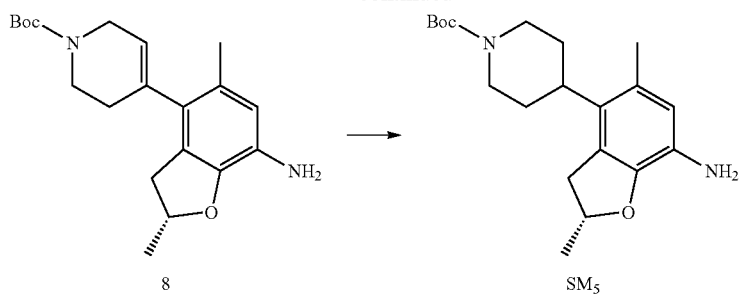
Reaction 2
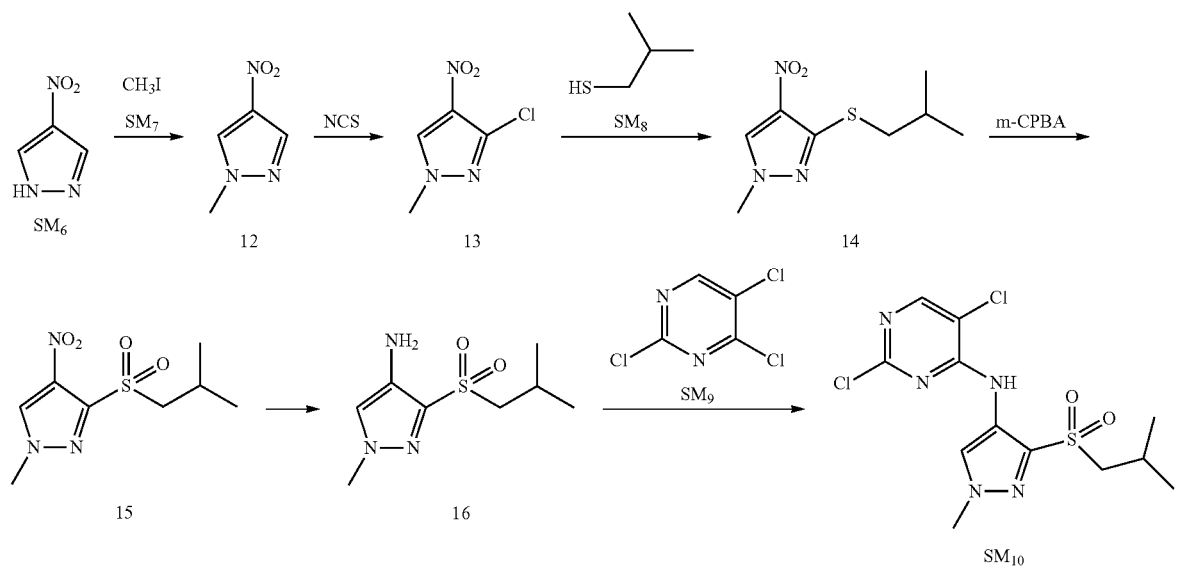
Reaction 3
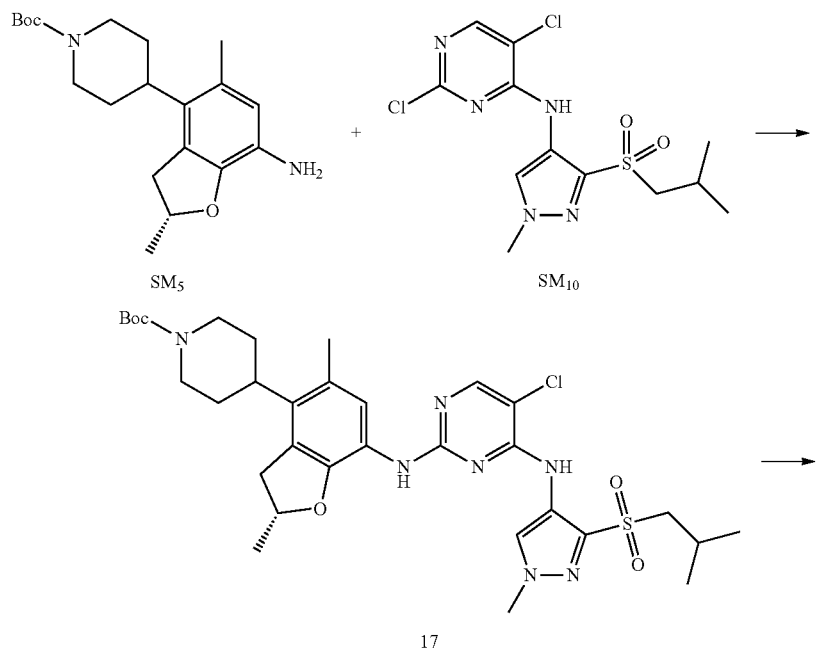

-continued
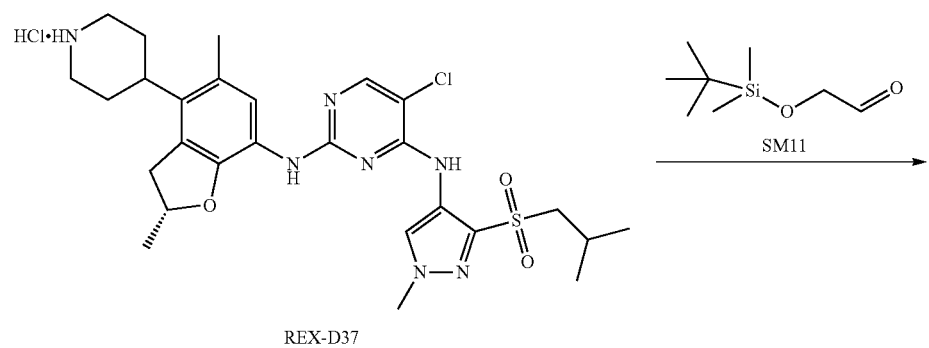
REX-D37 SM11
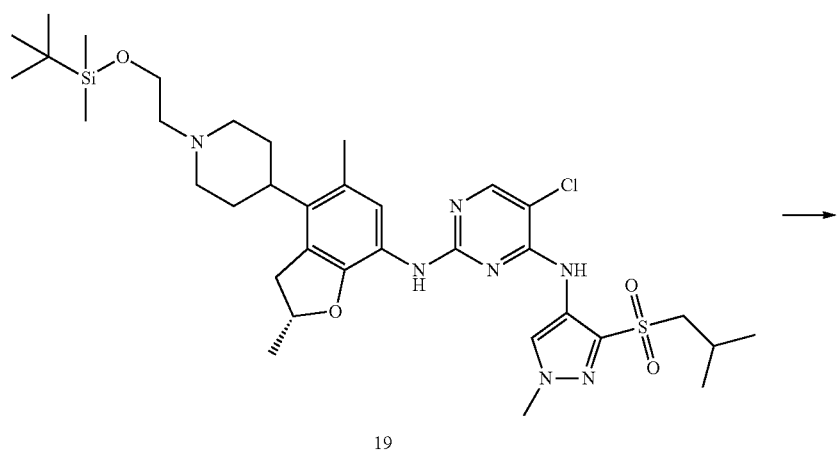
19
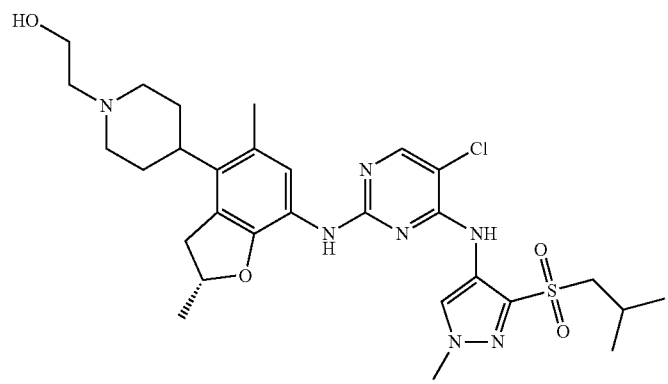
REX-39

According to synthetic routes as described in this example, the intermediate compound SM10: (2,5-dichloro-N-(3-(isobutylsulfonyl)-1-methyl-1H-pyrazol-4-yl)pyrimidin-4-amine) was prepared in the same manner as the reaction 1 and reaction 2 in example 5, except that the compound propane-2-thiol (SM8) in example 2 was replaced by the compound 2-methylpropane-1-thiol. (20.0% yield).

According to synthetic routes as described in this example, the compound REX-D39 was obtained in the same synthesis method as in example 5. (5.2% yield).

MS m/z [ESI]: 618.1 [M+1].

$^1$H-NMR DMSO-d$_6$), δ: 0.81-0.85 (m, 1H), 0.97-0.99 (m, 6H), 1.24-1.25 (m, 1H), 1.32-1.34 (m, 3H), 1.78-1.80 (m, 2H), 2.01-2.05 (m, 1H), 2.25-2.31 (m, 4H), 2.91-2.97 (m, 4H), 3.47-3.57 (m, 4H), 3.78-3.80 (m, 2H), 4.02-4.03 (m, 3H), 4.79-4.80 (m, 1H), 5.37-5.38 (m, 1H), 7.07 (s, 1H), 8.08 (s, 1H), 8.57 (s, 1H), 8.73 (s, 1H), 9.90-9.91 (m, 1H).

Example 28

(R)-5-chloro-N4-(1-cyclopropyl-3-(isobutylsulfonyl)-1H-pyrazol-4-yl)-N2-(2,5-dimethyl-4-(piperidin-4-yl)-2,3-dihydrobenzofuran-7-yl)pyrimidine-2,4-diamine [No. REX-D40]

Synthetic Routes:

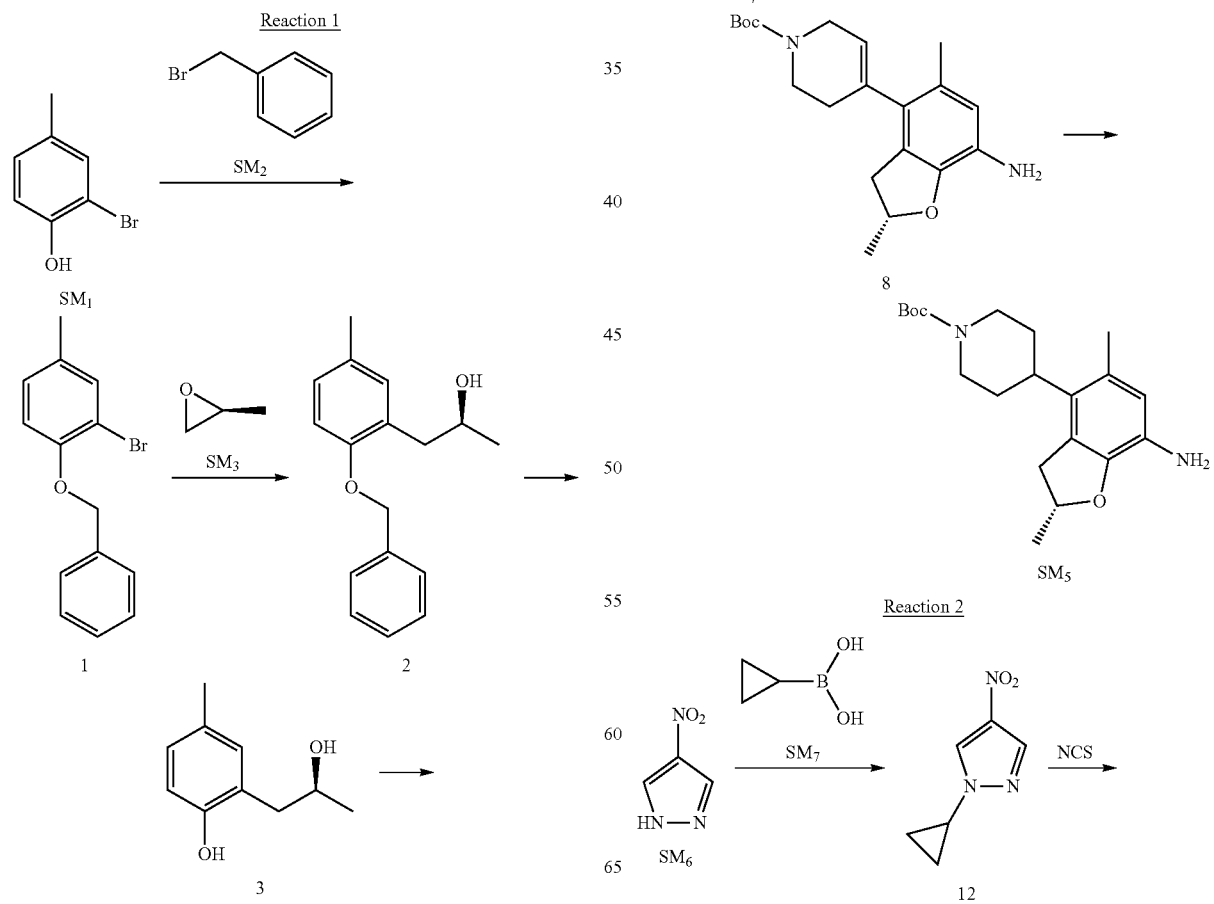

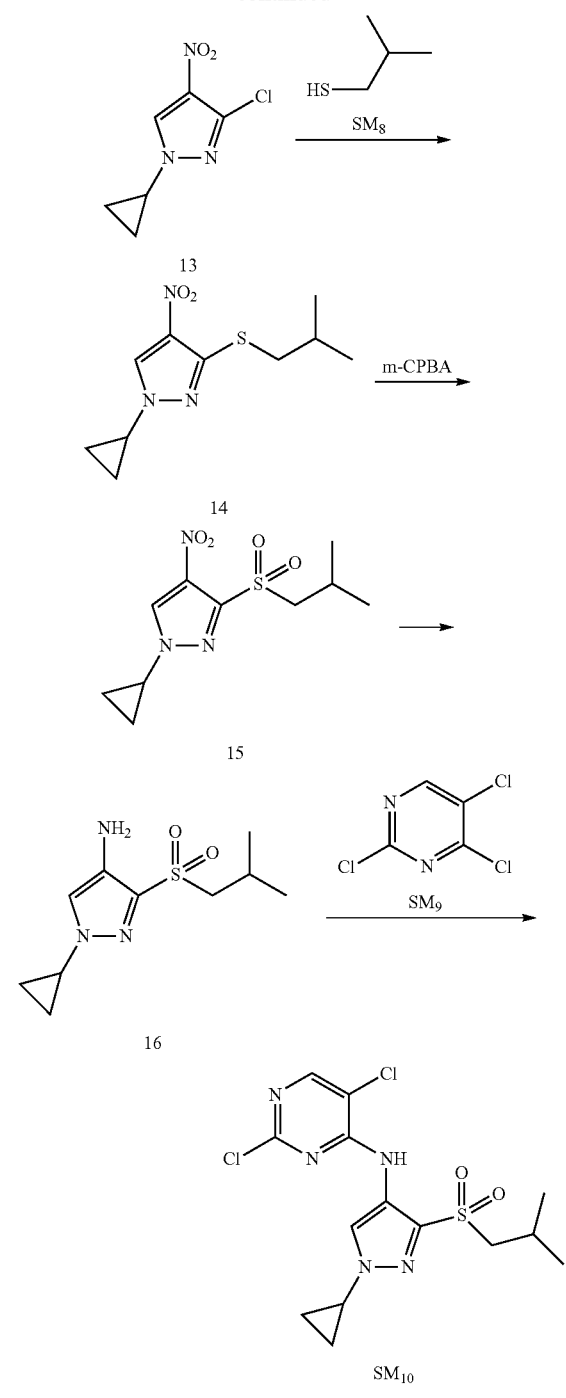

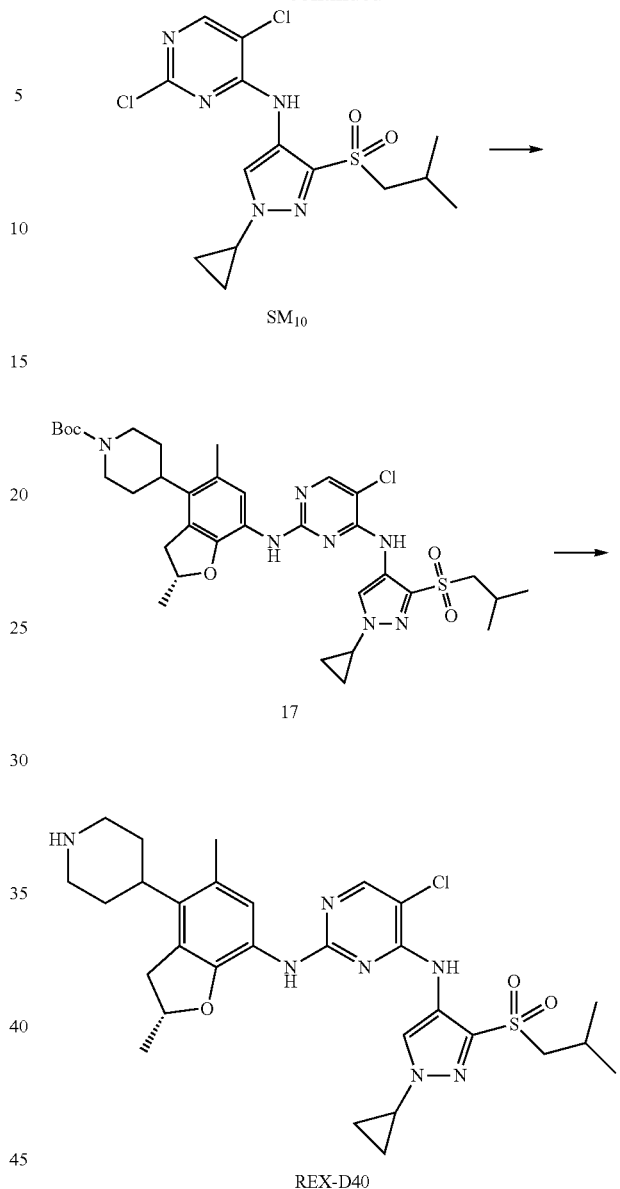

According to synthetic routes as described in this example, the intermediate compound SM10: (2,5-dichloro-N-(1-cyclopropyl-3-(isobutylsulfonyl)-1H-pyrazol-4-yl)pyrimidin-4-amine) was prepared in the same manner as the reaction 1 and reaction 2 in example 25, except that the compound iodomethane (SM7) in example 25 was replaced by the compound cyclopropylboronic acid. (17.0% yield). According to synthetic routes as described in this example, the compound REX-D40 was obtained in the same synthesis method as in example 25. (3.2% yield).

MS m/z [ESI]: 601.1 [M+1].

$^1$H-NMR DMSO-$d_6$), δ: 1.11-1.14 (m, 6H), 1.22-1.23 (m, 3H), 1.33-1.40 (m, 5H), 1.94-1.98 (m, 3H), 2.22-2.31 (m, 4H), 2.47-2.53 (m, 2H), 3.02-3.08 (m, 4H), 3.23-3.25 (m, 2H), 3.55-3.70 (m, 3H), 4.02-4.03 (m, 1H), 4.83-4.85 (m, 1H), 5.37-5.38 (m, 1H), 7.85 (s, 1H), 7.96 (s, 1H), 9.34 (s, 1H), 9.77 (s, 1H).

Example 29
(R)-5-chloro-N4-(1-cyclopropyl-3-(isobutylsulfonyl)-1H-pyrazol-4-yl)-N2-(2,5-dimethyl-4-(1-methylpiperidin-4-yl)-2,3-dihydrobenzofuran-7-yl)pyrimidine-2,4-diamine [No. REX-D41]
Synthetic Routes:
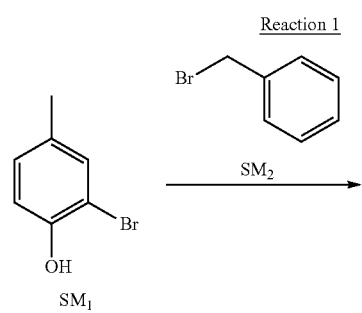
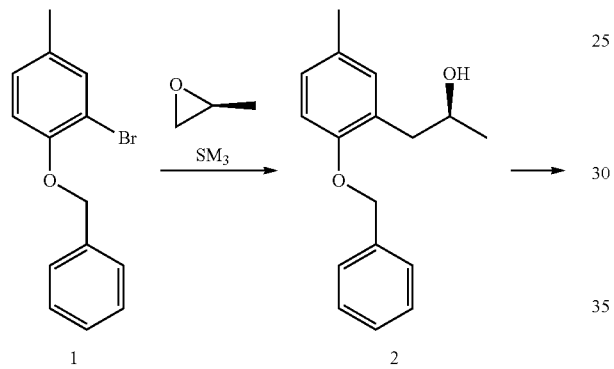
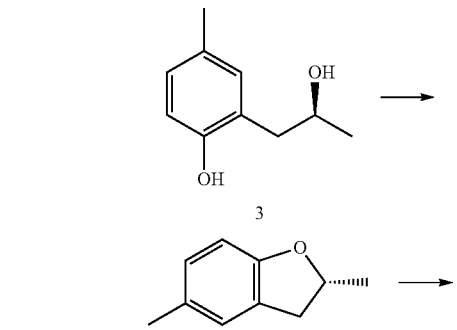
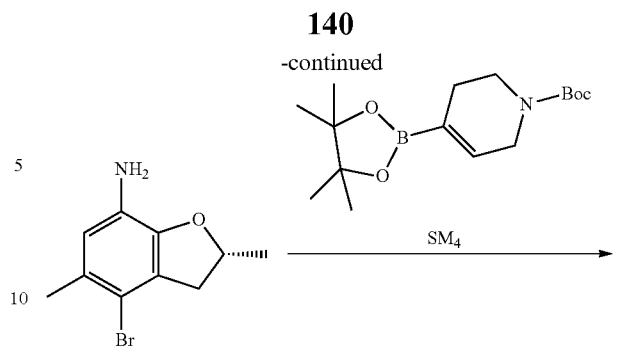
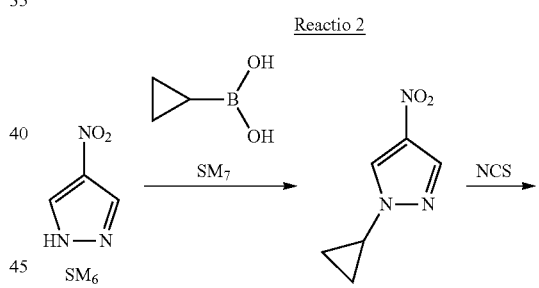
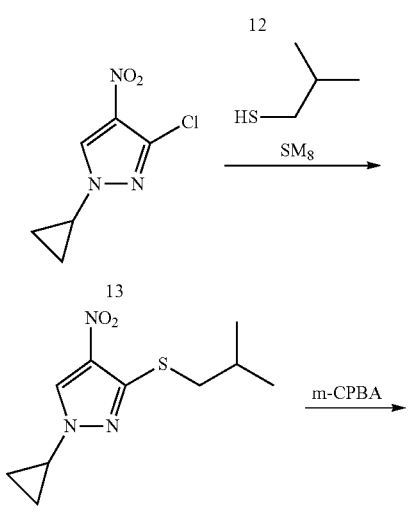

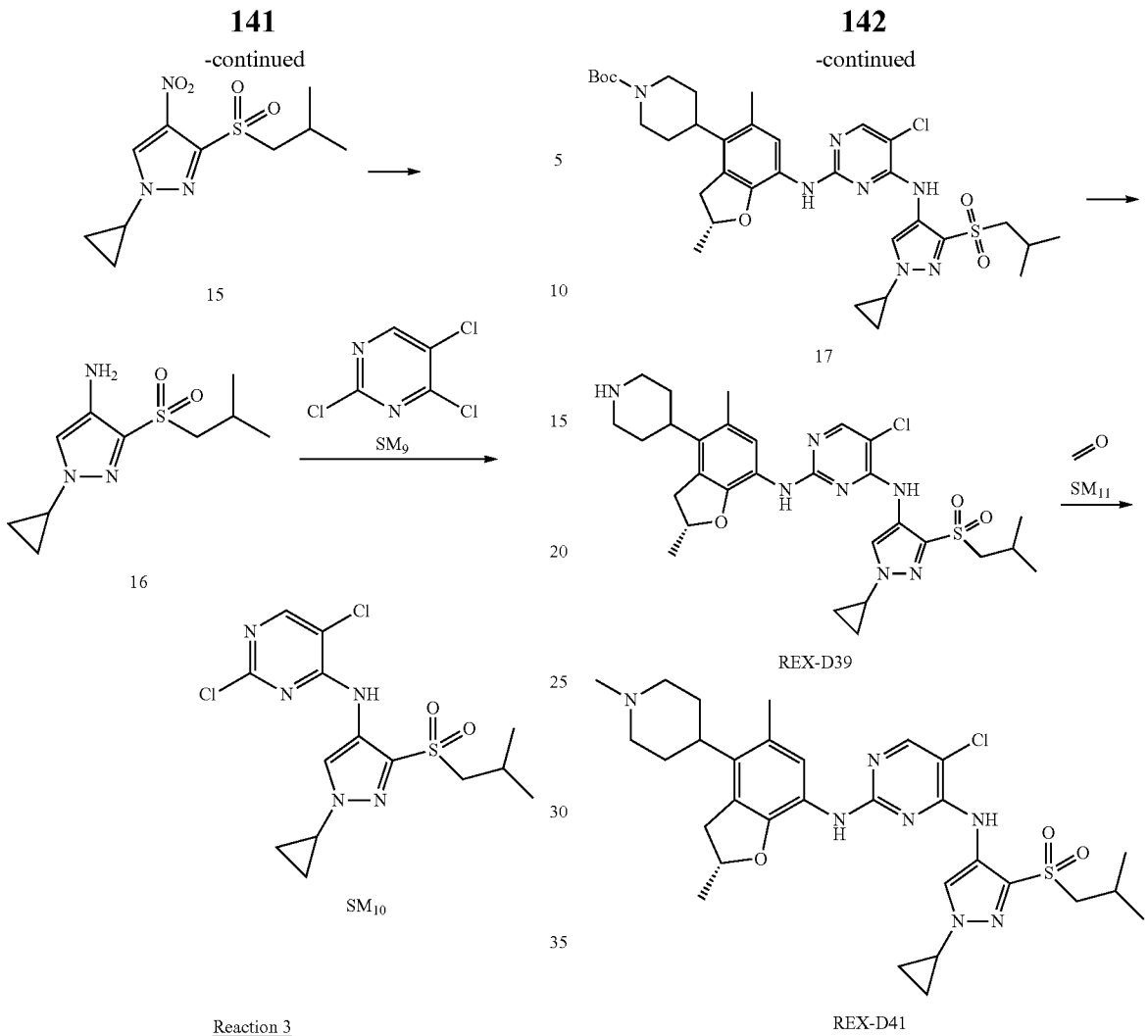

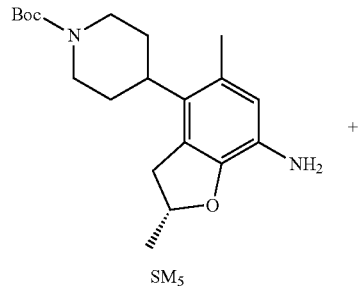

Reaction 3

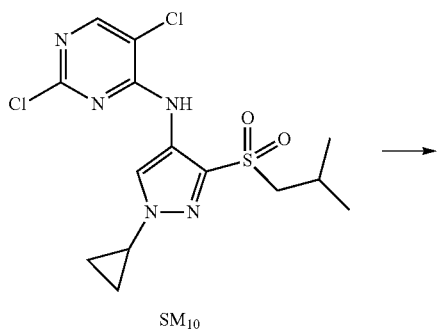

According to synthetic routes as described in this example, the intermediate compound SM10: (2,5-dichloro-N-(1-cyclopropyl-3-(isobutylsulfonyl)-1H-pyrazol-4-yl)pyrimidin-4-amine) was prepared in the same manner as the reaction 1 and reaction 2 in example 26, except that the compound iodomethane (SM7) in example 26 was replaced by the compound cyclopropylboronic acid. (18.0% yield). According to synthetic routes as described in this example, the compound REX-D41 was obtained in the same synthesis method as in example 26. (4.4% yield).

MS m/z [ESI]: 615.2 [M+1].

Example 30 the Measure of Compounds on Wild-Type ALK and ALK Mutants

The Z'-LYTE® (FRET) method was used for determining ALK kinase inhibitory activity $IC_{50}$ for the compounds REX-D1-D5, REX-D9-D14 and REX-D31-36 prepared in the above examples, wherein $IC_{50}$ is defined as a concentration at which the compound inhibit 50% of kinase activity.

Meanwhile, The LanthaScreen® Eu Kinase Binging Assay (TR-FRET) method was used for determining ALK Mutants (such as ALK L1196M) inhibitory activity $IC_{50}$. LanthaScreen Eu kinase binding experiment detected Alexa Fluor conjugate or kinase "tracer" binding by adding Eu labeled antibodies or anti-label antibodies. The combination of tracer and antibody with kinase leads to a high level of FRET, whereas the use of kinase inhibitors in place of tracer may cause FRET loss.

The kinase activity assay was determined by using kinase assay panel (Life Technology) and the result was in table 1.

The results indicate that the compounds in the present invention had good inhibitory activity against Wild-Type ALK kinase and good binding rate to ALK Mutants such as ALK L1196M.

TABLE 1

IC$_{50}$ values of the compounds on Wild-Type ALK and ALK L1196M kinase assays

| | ALK IC$_{50}$ (nM) | ALK L1196M IC$_{50}$ (nM) |
|---|---|---|
| REX-D1 | 6.82 | 1.34 |
| REX-D2 | 13.3 | 0.695 |
| REX-D3 | 15.9 | 1.25 |
| REX-D4 | 5.9 | 0.565 |
| REX-D5 | 15 | <0.5 |
| REX-D9 | 15.8 | 1.02 |
| REX-D10 | 17.1 | <0.5 |
| REX-D11 | 8.46 | <0.5 |
| REX-D12 | 9.21 | 1.07 |
| REX-D13 | 18.8 | 1.02 |
| REX-D14 | 15.7 | 1.1 |
| REX-D31 | 15.1 | 1.92 |
| REX-D32 | 19.3 | 3.86 |
| REX-D33 | 15.5 | 2 |
| REX-D34 | 9.4 | 1.12 |
| REX-D35 | 13.9 | 1.99 |
| REX-D36 | 9.28 | 0.55 |

Example 31 Cell Proliferation Experiment (Cell-Titer GLO Detection)

Compounds to be tested: Positive compound Ceritinib and the compounds obtained by the examples of the present invention.

Cell lines: Karpas-299 and NCI-H3122 which were purchased from the Nanjing kebai biotechnology Co. LTD; TEL-ALK-F1174L-BaF3, TEL-ALK-G1202R-BaF3, TEL-ALK-C1156Y-BaF3 and TEL-ALK-L1196M-BaF3 which were purchased from Hefei zhongkopruisheng biological medicine technology Co. LTD.

Method: Cells were seeded in 96-well plates for 24 h in growth media containing 10% fetalbovine serum (FBS) and cultured overnight at 37° C. The following day, serial dilutions of compounds or appropriate control were added to the designated wells, and cells were incubated at 37° C. for 72 h. A Cell Titer Glo assay (Promega) was then performed to determine the relative cell numbers. IC$_{50}$ values were calculated by concentration-response curve fitting using a four-parameter analytical method with Graphpad 6.0.

Equation: Drug inhibition rate (%)=100%−[OD(Compound)−OD(blank)]/[OD(vehicle)−OD(blank)]×100%

Results: See in table 2.

TABLE 2

IC$_{50}$ values of compounds on different BaF3 Cell lines expressing mutated TEL-ALK, NCI-H3122 and Karpas-299

| IC$_{50}$ (nM) | TEL-ALK F1174L-BaF3 | TEL-ALK G1202R-BaF3 | TEL-ALK C1156Y-BaF3 | TEL-ALK L1196M-BaF3 | NCI-H3122 | Karpas-299 |
|---|---|---|---|---|---|---|
| Ceritinib | 36.1 | >180 | 36.5 | 17.2 | 40.7 | 40-85 |
| REX-D1 | <10 | >180 | 10.5 | 10.5 | 10.6 | <20 |
| REX-D2 | <10 | <50 | 10.4 | 10.5 | 10.6 | <10 |
| REX-D3 | <10 | <140 | 10.5 | 10.4 | 10.8 | <20 |
| REX-D4 | <10 | <50 | 10.5 | 10.5 | 10.6 | <10 |
| REX-D5 | 80.1 | >180 | — | — | 10.7 | — |
| REX-D8 | 11.4 | >180 | — | — | — | — |
| REX-D9 | 51.8 | >180 | — | — | 11.8 | — |
| REX-D10 | <200 | >180 | — | — | 14.2 | — |
| REX-D11 | 10.7 | >180 | — | — | 10.6 | — |
| REX-D12 | 11.6 | >180 | — | — | 10.7 | — |
| REX-D13 | 94.3 | >180 | — | — | 33.7 | — |
| REX-D14 | 11.2 | >180 | — | — | 10.7 | — |
| REX-D21 | 17.8 | >180 | — | — | — | — |
| REX-D22 | 32.6 | >180 | — | — | — | — |
| REX-D24 | <10 | >180 | — | — | — | — |
| REX-D25 | 11.1 | >180 | — | — | — | — |
| REX-D29 | >500 | >180 | — | — | — | — |
| REX-D30 | >500 | >180 | — | — | — | — |
| REX-D31 | 138 | >180 | — | — | 40.4 | — |
| REX-D32 | <200 | >180 | — | — | 57.2 | — |
| REX-D33 | 33.4 | >180 | — | — | 11.7 | — |
| REX-D34 | 26.1 | >180 | — | — | 13.9 | — |
| REX-D35 | 80.4 | >180 | — | — | 40.3 | — |
| REX-D36 | 22.4 | >180 | — | — | 11.4 | — |
| REX-D37 | 58.7 | >180 | — | — | — | — |
| REX-D38 | <10 | >180 | — | — | — | — |
| REX-D39 | <10 | >180 | — | — | — | — |
| REX-D40 | 94.8 | >180 | — | — | — | — |
| REX-D41 | 23.7 | >180 | — | — | — | — |

Note:
"—" indicates not detected

Example 32 Phenotypic Screening of Zebrafish

Zebrafish (Danio rerio) is emerging as a predictive vertebrate animal model for in vivo assessment of drug efficacy, toxicity and safety. An important advantage of the zebrafish animal model is that the morphological and molecular basis of tissues and organs is either identical or similar to other vertebrates, including humans. The sequence and presumed function of many genes that are important for vertebrates are conserved in the zebrafish and the homology is as high as 85%. It has been shown that loss-of-function alleles for leukocyte tyrosine kinase (Ltk), the sister kinase to ALK, lack iridophores in zebrafish (Lopes, S. S., Yang, X., et al. (2008). Leukocyte tyrosine kinase functions in pigment cell development. PLoS Genet, 4.). Iridophores are neural crest-derived pigment cells that are clearly visible as shiny silver cells in the developing zebrafish embryo which distribute in the head, eyes, the lateral spine. ALK and LTK are sister kinase. The researchers found that the exogenous ALK plasmid injected can also regulate the production of iris pigment cells. The experimental results also showed that ALK inhibitors mostly have LTK activity and can inhibit the generation of iris pigment cells (Rodrigues, F. S., Yang, X., Nikaido, M., Liu, Q., & Kelsh, R. N. (2012). A simple, highly visual in vivo screen for anaplastic lymphoma kinase inhibitors. ACS Chem Biol, 7, 1968-1974.).

Therefore, using this principle, we investigated the effect of the compounds on normal zebrafish iridophore pigment cells to explore the compound's anti-ALK activity in vivo.

Experiment 1: The Effect of the Compounds on Normal Zebrafish Iridophore Pigment Cells Method: Fish eggs of 6 hpf (hours post impurity) were randomly divided into groups. Then, subjects with different concentrations were added and the images were collected at 3 dpf (days post impurity). Then, the IOD (integrated option density) values of zebrafish dorsal iridophore pigment cells from the release pore to the caudal position were analyzed using ImageJ software. The Graphpad prism6.0 was used to conduct statistical analysis on Dunnett's t-test, and $p<0.05$ indicates statistical difference. The calculation formula of iridophore pigment inhibition rate is as follows:

Inhibition rate (%)=[1−IOD(Compound)/IOD(vehicle)]×100%

TABLE 3

The effect of REX-D2 on normal zebrafish iridophore pigment cells

| Group | IOD | Inhibition rate % |
|---|---|---|
| Control | 683.3 ± 46.4 | — |
| Ceritinib 15 μM | 35.5 ± 7.0 | 95%** |
| REX-D2-5 μM | 420.9 ± 34.1 | 38%** |
| REX-D2-10 μM | 173.8 ± 20.5 | 75%** |
| REX-D2-15 μM | 64.6 ± 16.1 | 91%** |
| REX-D2-20 μM | 24.8 ± 5.8 | 96%** | compared with control,
* $p < 0.05$;
** $p < 0.01$

Figure 2:
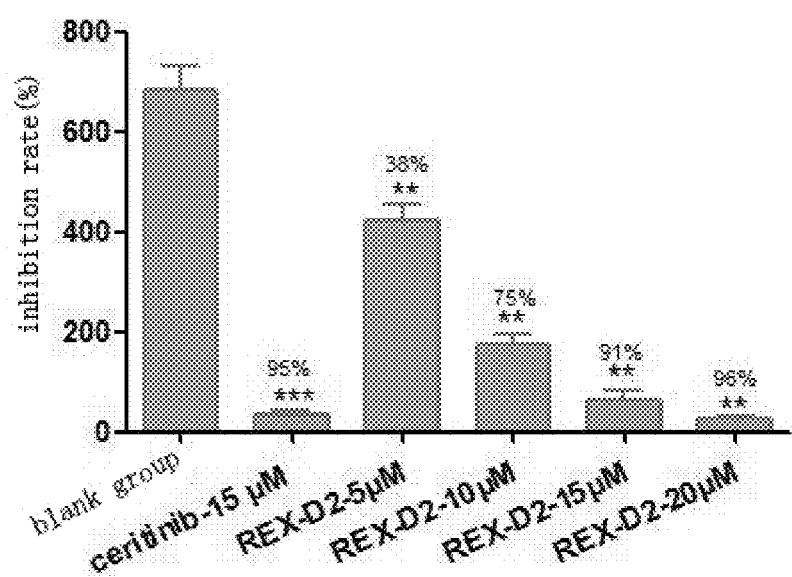
FIG. 2 shows the dose-response of compound REX-D2 on iridophores pigment cells of zebrafish.
Figure 3:
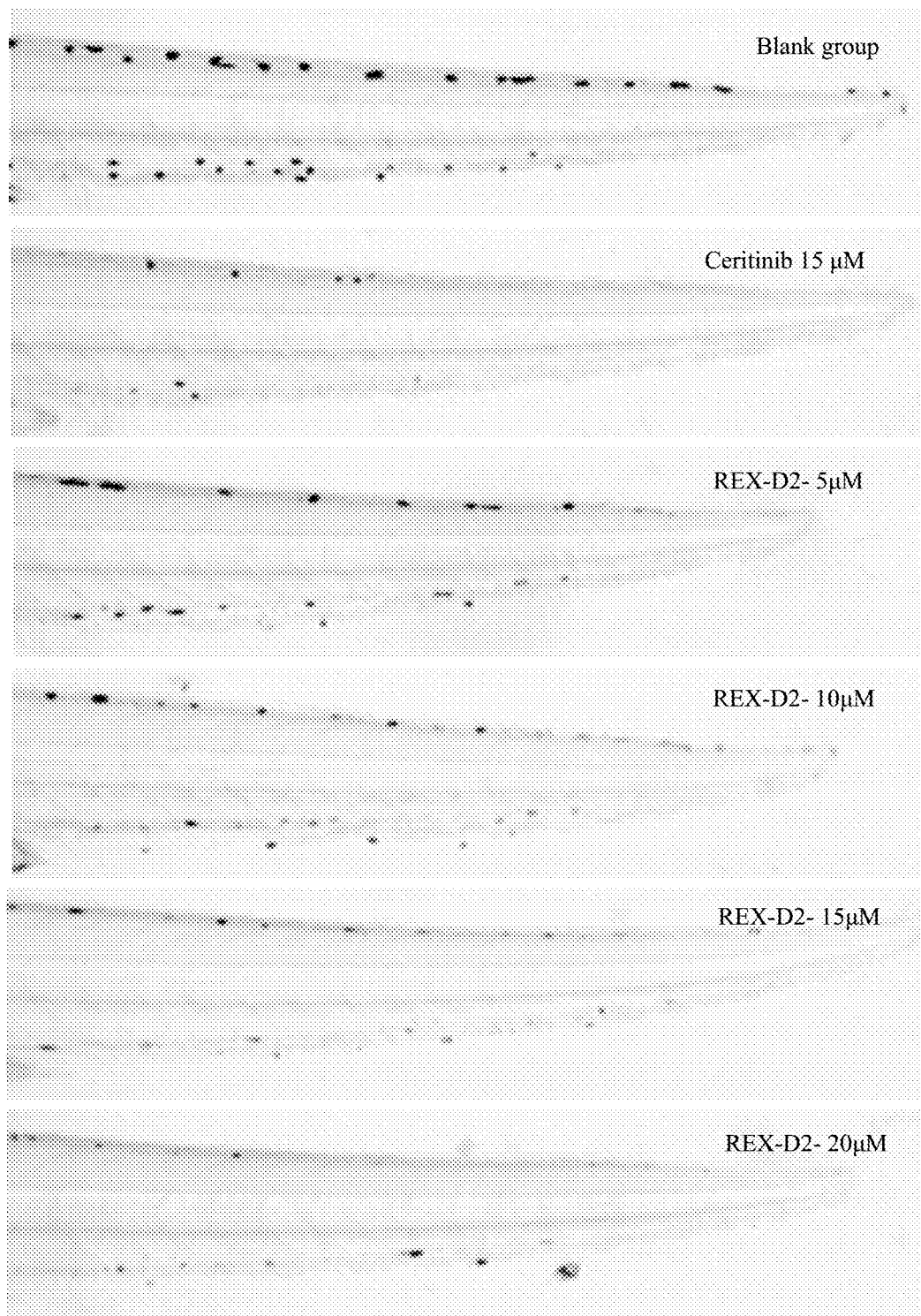
FIG. 3 shows that the effect of REX-D2 on the iridophore pigment cells of zebrafish.

The dose-effect relationship of REX-D2 on the iridophore pigment cells of zebrafish is shown in FIG. 2. The effect of REX-D2 on the iridophore pigment cells of zebrafish is shown in FIG. 3. It can be clearly seen from the figure that the compound REX-D2 has significant inhibition of the formation of iridophore pigment cells at different doses of concentration, indicating that this compound has significant anti-ALK activity in the vivo.

Example 33 In Vivo Efficacy Study of REX-D2 Against Subcutaneous NCI-H2228 Lung Cancer Xenograft Model (1) Method BALB/C nude mice were inoculated at the right flank with NCI-H2228 tumor cells to establish the human Lung cancer xenograft model. Three experimental groups were as follows: vehicle, PO*QD*14 days; Ceritinib 30 mg/kg, PO*QD*14 days; REX-D2 30 mg/kg, PO*QD*14 days; 8 mice in each group. The drug was administered for 14 days and then discontinued for two weeks. The therapeutic effect was evaluated by calculating the relative tumor proliferation rate T/C (%), and the tolerability of treatment was evaluated by the body weight changes and death.

(2) Evaluation Index

Tumor volume (TV) were measured twice per week in two dimensions using a caliper, and the volume were expressed in $mm^3$ using the formula: $V=0.5\ a \times b^2$ where a and b are the long and short diameters of the tumor, respectively.

Relative tumor volume $RTV=Vt/V_0$, $V_t$=tumor volume of the drug-treated group on a given day of the study, $V_0$=tumor volume of the drug-treated group on the initial day of dosing.

Figure 4:
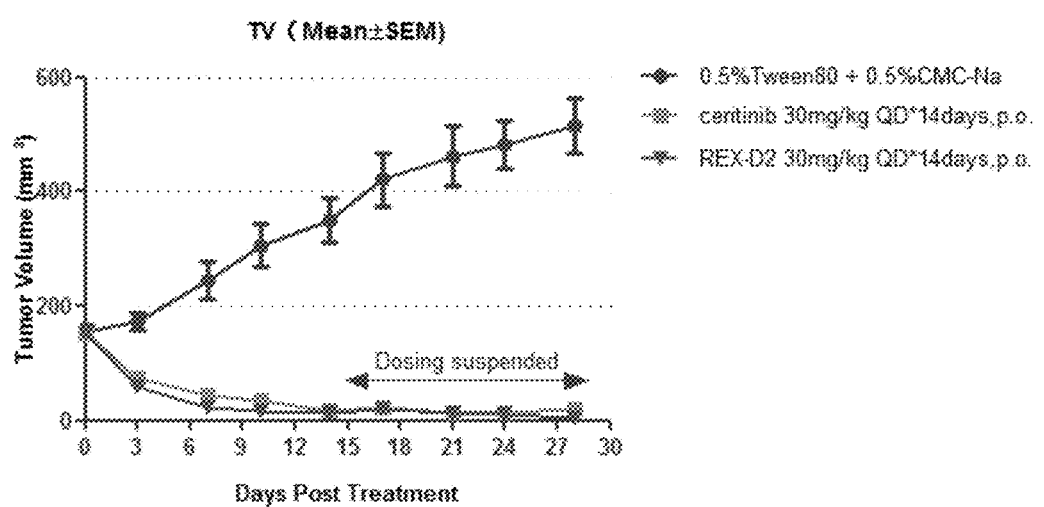
FIG. 4 shows tumor volumes of mice in different groups during the treatment with the compound REX-D2 in NCI-H2228 Xenograft Model.

The T/C value (%) is an indicator of tumor response to treatment, and one of commonly used anti-tumor activity endpoint; T/C %=$T_{RTV}/C_{RTV} \times 100\%$ Relative Tumor Growth Inhibition; % TGI=(1−T/C)× 100%;

(3) Results: See in FIG. 4

The mean tumor volume of negative control group was 350 $mm^3$ at 14 days after administration (i.e. the first day after administration end). Compared with the vehicle group, the tumor volume in the treatment with Ceritinib, REX-D2 were 17 $mm^3$, 13 $mm^3$, all produced significant anti-tumor activities statistically and biologically (p=0.001, p<0.001). The TGI of Ceritinib and REX-D2 were 94.7%, 96.1%. The tumors were significantly smaller or cured than when the administration began.

At the end of the experiment (i.e., 15 days after the administration), the average tumor volume in mice in the negative control group was 515 $mm^3$. No tumor growth was found in the treated mice, and the tumor was reduced. The TGI of Ceritinib and REX-D2 were 95.3% and 98.8%.

Conclusion: Under the dose of 30 mg/kg, once a day and continuously for 14 days, the tested drugs ceritinib and REX-D2 had significant anti-tumor effect on the subcutaneous transplantation model of NCI-H2228 Lung cancer. All the tested drugs could be tolerated under the conditions set in this experiment.

The invention claimed is:

1. A compound having the following general structural formula (I) or a pharmaceutically acceptable salt thereof:

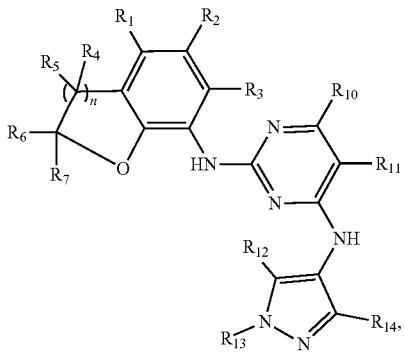

(I)

Wherein $R_1$ is selected from

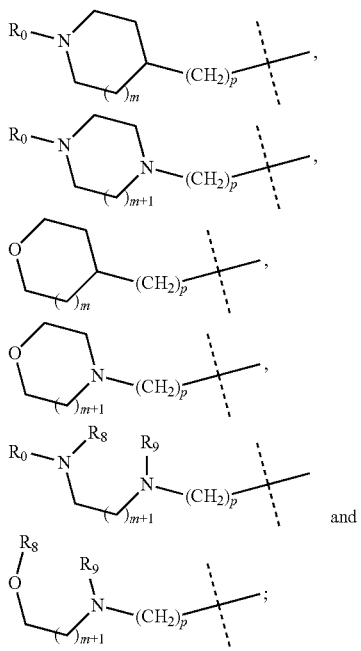

and $R_0$, $R_8$ and $R_9$ are each independently selected from one or more of the group consisting of hydrogen, $C_{1-6}$ alkyl, $C_{2-6}$ alkenyl, $C_{2-6}$ alkynyl, acyl, amido, sulfo group, sulfanilamido, hydroxyl, aryl and heterocyclyl;

$R_2$, $R_3$, $R_4$, $R_5$, $R_6$, $R_7$, $R_{10}$ and $R_{11}$ are each independently selected from the group consisting of hydrogen, halogen, $C_{1-6}$ alkyl, halogenated $C_{1-6}$ alkyl, $C_{1-6}$ alkoxy, halogenated $C_{1-6}$ alkoxy, $C_{2-6}$ alkenyl, $C_{2-6}$ alkynyl, cyano and amino;

$R_{13}$ is selected from one or more of the group consisting of hydrogen, $C_{1-6}$ alkoxy, $C_{1-6}$ alkyl, $C_{3-6}$ cycloalkyl, $C_{2-6}$ alkenyl, $C_{2-6}$ alkynyl, amido, boryl, amino, hydroxyl, cyano, carbonyl, carboxy, aryl and heterocyclyl;

$R_{12}$ and $R_{14}$ are each independently selected from one or more of the group consisting of hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl;

$R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus;

the heterocyclyl is a 3-12 membered heterocyclic ring containing one or more of N and O atoms;

m is selected from any integer from 0 to 3; p is selected from any integer from 0 to 6; and n is 1 or 2.

2. The compound according to claim 1, wherein the compound has the following general structural formula (I a) or a pharmaceutically acceptable salt thereof:

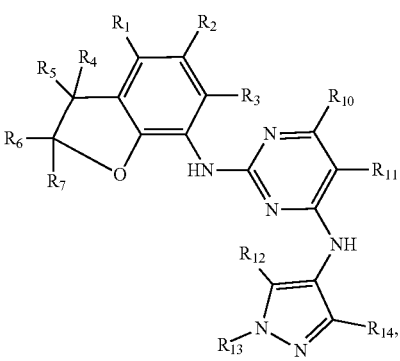

(I a)

Wherein $R_1$ is selected from

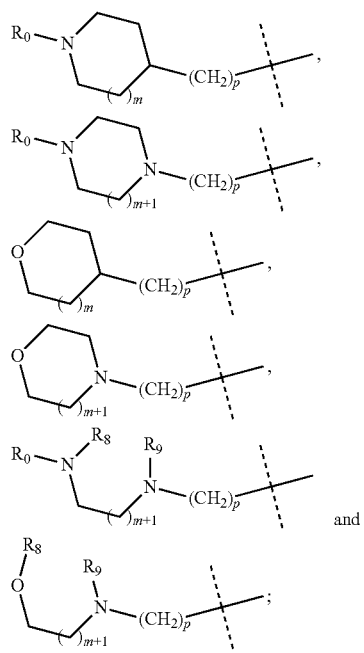

and $R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl;

$R_2$, $R_3$, $R_4$, $R_5$, $R_6$, $R_7$, $R_{10}$ and $R_{11}$ are each independently selected from the group consisting of hydrogen, halogen, $C_{1-6}$ alkyl, halogenated $C_{1-6}$ alkyl, $C_{1-6}$ alkoxy, halogenated $C_{1-6}$ alkoxy, cyano and amino;

$R_{13}$ is selected from one or more of the group consisting of hydrogen, $C_{1-6}$ alkoxy, $C_{1-6}$ alkyl, $C_{3-6}$ cycloalkyl, amido, boryl, amino, hydroxyl, cyano, carbonyl, carboxy, aryl and heterocyclyl;

$R_{12}$ and $R_{14}$ are each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl;

$R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus;

the heterocyclyl is a 3-6 membered heterocyclic ring containing one or more of N and O atoms;

m is selected from any integer from 0 to 3; and p is selected from any integer from 0 to 6.

3. The compound according to claim 2, wherein in the general structural formula (I a), $R_1$ is selected from

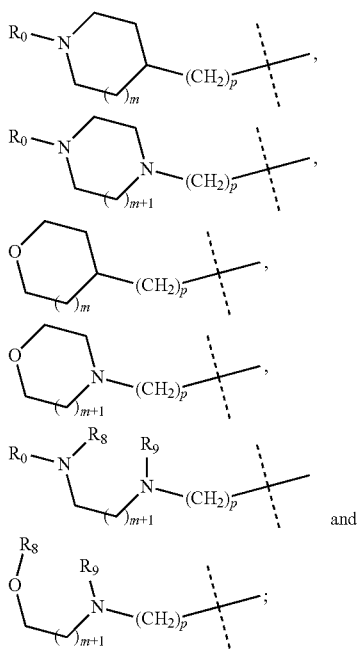

$R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl;

$R_2$ and $R_3$ are simultaneously hydrogen, or
one of $R_2$ and $R_3$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino;

$R_4$ and $R_5$ are simultaneously hydrogen, or
one of $R_4$ and $R_5$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino;

$R_6$ and $R_7$ are simultaneously hydrogen, or
one of $R_6$ and $R_7$ is hydrogen and the other is halogen, $C_{1-6}$ alkyl, halogenated $C_{1-6}$ alkyl, $C_{1-6}$ alkoxy, or halogenated $C_{1-6}$ alkoxy;

$R_{10}$ and $R_{11}$ are simultaneously hydrogen, or
one of $R_{10}$ and $R_{11}$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino;

$R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus;

$R_{13}$ is selected from the group consisting of hydrogen, $C_{1-6}$ alkoxy, $C_{1-6}$ alkyl, $C_{3-6}$ cycloalkyl, amido, amino-containing $C_{1-6}$ alkyl, $C_{1-6}$ alkylcarbonyl, aryl and heterocyclyl;

$R_{12}$ and $R_{14}$ are each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl;

the heterocyclyl is a 3-6 membered heterocyclic ring containing one or more of N and O atoms;

m is selected from any integer from 0 to 3; and p is selected from any integer from 0 to 6.

4. The compound according to claim 1, wherein the compound has the following general structural formula (I b) or a pharmaceutically acceptable salt thereof:

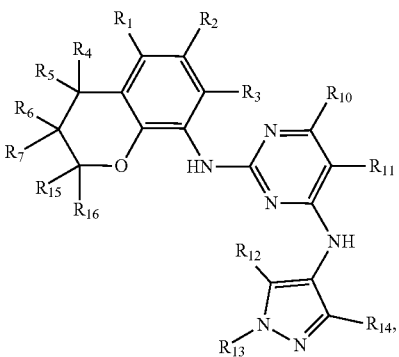

(I b)

Wherein $R_1$ is selected from

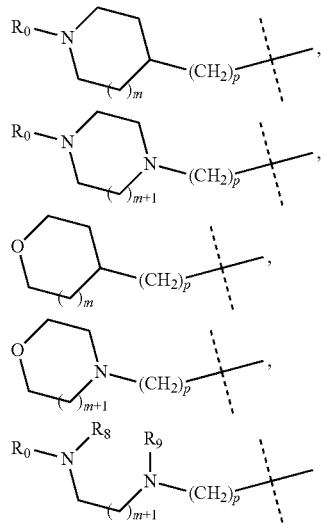

and

-continued

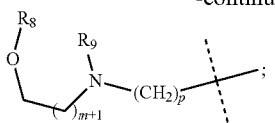

$R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl;

$R_2$, $R_3$, $R_4$, $R_5$, $R_6$, $R_7$, $R_{10}$, $R_{11}$, $R_{15}$ and $R_{16}$ are each independently selected from the group consisting of hydrogen, halogen, $C_{1-6}$ alkyl, halogenated $C_{1-6}$ alkyl, $C_{1-6}$ alkoxy, halogenated $C_{1-6}$ alkoxy, cyano and amino;

$R_{13}$ is selected from one or more of the group consisting of hydrogen, $C_{1-6}$ alkoxy, $C_{1-6}$ alkyl, $C_{3-6}$ cycloalkyl, amido, boryl, amino, hydroxyl, cyano, carbonyl, carboxy, aryl and heterocyclyl;

$R_{12}$ and $R_{14}$ are each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl;

$R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus;

the heterocyclyl is a 3-6 membered heterocyclic ring containing one or more of N and O atoms;

m is selected from any integer from 0 to 3; and p is selected from any integer from 0 to 6.

5. The compound according to claim 4, wherein in the general structural formula (I b), $R_1$ is selected from

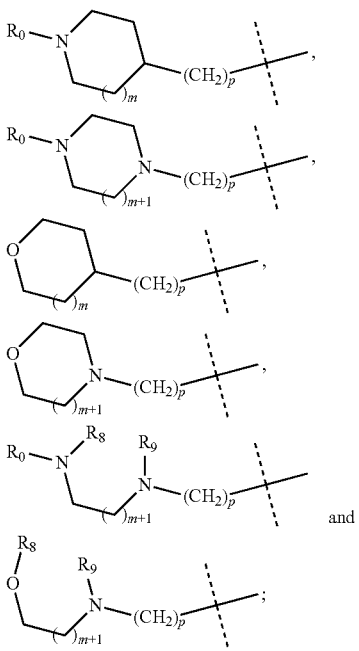

$R_0$, $R_8$ and $R_9$ are each independently selected from one or more of the group consisting of hydrogen, $C_{1-6}$ alkyl, acyl, amido, sulfo group, sulfanilamido, hydroxyl, aryl and heterocyclyl;

$R_2$ and $R_3$ are simultaneously hydrogen, or
one of $R_2$ and $R_3$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino;

$R_4$ and $R_5$ are simultaneously hydrogen, or
one of $R_4$ and $R_5$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino;

$R_6$ and $R_7$ are simultaneously hydrogen, or
one of $R_6$ and $R_7$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino;

$R_{15}$ and $R_{16}$ are simultaneously hydrogen, or
one of $R_{15}$ and $R_{16}$ is hydrogen and the other is halogen, $C_{1-6}$ alkyl, halogenated $C_{1-6}$ alkyl, $C_{1-6}$ alkoxy, or halogenated $C_{1-6}$ alkoxy;

$R_{10}$ and $R_{11}$ are simultaneously hydrogen, or
one of $R_{10}$ and $R_{11}$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino;

$R_{10}$ and $R_{11}$ each substitute at the pyrimidine of the parent nucleus, or $R_{10}$ and $R_{11}$ are linked to each other to form a 5-7 membered saturated or unsaturated carbocyclic or heterocyclic ring fused with the pyrimidine of the parent nucleus;

$R_{13}$ is selected from the group consisting of hydrogen, $C_{1-6}$ alkoxy, $C_{1-6}$ alkyl, $C_{3-6}$ cycloalkyl, amido, amino-containing $C_{1-6}$ alkyl, $C_{1-6}$ alkylcarbonyl, aryl and heterocyclyl;

$R_{12}$ and $R_{14}$ are each independently selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl;

the heterocyclyl is a 3-6 membered heterocyclic ring containing one or more of N and O atoms;

m is selected from any integer from 0 to 3; and p is selected from any integer from 0 to 6.

6. The compound according to claim 3 has the following general structural formula (I c) or a pharmaceutically acceptable salt thereof:

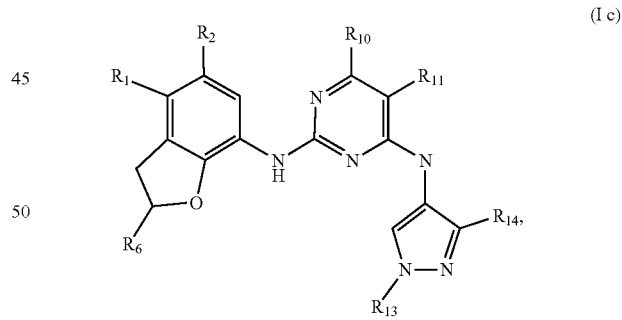

(I c)

Wherein $R_1$ is selected from

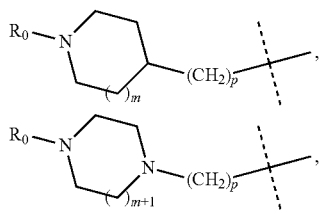

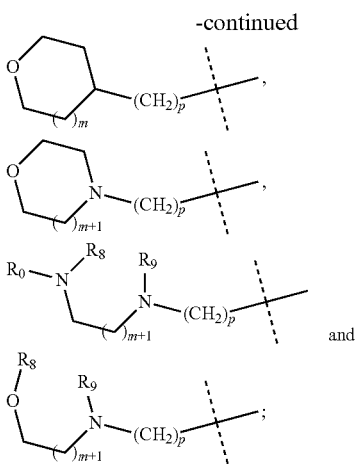

R₀, R₈ and R₉ are each independently selected from one or more of the group consisting of hydrogen, $C_{1-6}$ alkyl, acyl, amido, sulfo group, sulfanilamido, hydroxyl, aryl and heterocyclyl;

$R_2$ is hydrogen, halogen, $C_{1-6}$ alkyl, halogenated $C_{1-6}$ alkyl, $C_{1-6}$ alkoxy, halogenated $C_{1-6}$ alkoxy, cyano or amino;

$R_6$ is hydrogen, halogen, $C_{1-6}$ alkyl, halogenated $C_{1-6}$ alkyl, $C_{1-6}$ alkoxy, or halogenated $C_{1-6}$ alkoxy, and $R_6$ constitutes R form, S form or enantiomer;

$R_{10}$ and $R_{11}$ are simultaneously hydrogen, or one of $R_{10}$ and $R_{11}$ is hydrogen and the other is halogen, $C_{1-6}$ alkyl, halogenated $C_{1-6}$ alkyl, $C_{1-6}$ alkoxy, halogenated $C_{1-6}$ alkoxy, cyano or amino;

$R_{13}$ is selected from the group consisting of hydrogen, $C_{1-6}$ alkoxy, $C_{1-6}$ alkyl, $C_{3-6}$ cycloalkyl, amido, amino-containing $C_{1-6}$ alkyl, $C_{1-6}$ alkylcarbonyl, aryl or heterocyclyl;

$R_{14}$ is selected from one or more of the group consisting of hydrogen, halogen, $C_{1-6}$ alkyl, $C_{1-6}$ alkoxy, $C_{3-6}$ cycloalkyl, amino, amido, hydroxyl, carbonyl, ureido, sulfuryl, sulfamido, phosphoroso, boryl, aryl and heterocyclyl;

the heterocyclyl is a 3-6 membered heterocyclic ring containing one or more of N and O atoms;

m is selected from any integer from 0 to 3; and p is selected from any integer from 0 to 6.

7. The compound according to claim 1, wherein the aryl is phenyl, naphthyl or anthryl; the heterocyclyl is morpholinyl, piperidyl, pyranyl, pyrazolyl, furyl, pyridyl or pyrimidinyl; and the halogen is selected from one or more of the group consisting of fluorine, chlorine, bromine and iodine.

8. A compound selected from the following:
(R)-5-chloro-$N^2$-(2,5-dimethyl-4-(piperidin-4-yl)-2,3-dihydrobenzofuran-7-yl)-$N^4$-(3-(isopropylsulfonyl)-1-methyl-1H-pyrazol-4-yl)pyrimidine-2,4-diamine;
(R)-5-chloro-$N^2$-(2,5-dimethyl-4-(1-methylpiperidin-4-yl)-2,3-dihydrobenzofuran-7-yl)-$N^4$-(3-(isopropylsulfonyl)-1-methyl-1H-pyrazol-4-yl)pyrimidine-2,4-diamine;
(R)—N2-(2,5-dimethyl-4-(piperidin-4-yl)-2,3-dihydrobenzofuran-7-yl)-$N^4$-(3-(isopropylsulfonyl)-1-methyl-1H-pyrazol-4-yl)-5-(trifluoromethyl)pyrimidine-2,4-diamine;
(R)—$N^2$-(2,5-dimethyl-4-(1-methylpiperidin-4-yl)-2,3-dihydrobenzofuran-7-yl)-$N^4$-(3-(isopropylsulfonyl)-1-methyl-1H-pyrazol-4-yl)-5-(trifluoromethyl)pyrimidine-2,4-diamine;
(R)-2-(4-(7-((4-((3-(isopropylsulfonyl)-1-methyl-1H-pyrazol-4-yl)amino)-5-(trifluoromethyl)pyrimidin-2-yl)amino)-2,5-dimethyl-2,3-dihydrobenzofuran-4-yl)piperidin-1-yl)ethanol;
$N^2$-(2,6-dimethyl-5-(1-methylpiperidin-4-yl)chroman-8-yl)-$N^4$-(3-(isopropylsulfonyl)-1-methyl-1H-pyrazol-4-yl)-5-(trifluoromethyl)pyrimidine-2,4-diamine;
(R)—$N^4$-(3-(isopropylsulfonyl)-1-methyl-1H-pyrazol-4-yl)-$N^2$-(2-methyl-4-(1-methylpiperidin-4-yl)-2,3-dihydrobenzofuran-7-yl)-5-(trifluoromethyl)pyrimidine-2,4-diamine;
(R)—$N^2$-(5-fluoro-2-methyl-4-(1-methylpiperidin-4-yl)-2,3-dihydrobenzofuran-7-yl)-$N^4$-(3-(isopropylsulfonyl)-1-methyl-1H-pyrazol-4-yl)-5-(trifluoromethyl)pyrimidine-2,4-diamine;
(R)—$N^4$-(1-cyclopropyl-3-(isopropylsulfonyl)-1H-pyrazol-4-yl)-$N^2$-(2,5-dimethyl-4-(1-methylpiperidin-4-yl)-2,3-dihydrobenzofuran-7-yl)-5-(trifluoromethyl)pyrimidine-2,4-diamine;
(R)—$N^2$-(2,5-dimethyl-4-(1-methylpiperidin-4-yl)-2,3-dihydrobenzofuran-7-yl)-$N^4$-(3-(isobutylsulfonyl)-1-methyl-1H-pyrazol-4-yl)-5-(trifluoromethyl)pyrimidine-2,4-diamine;
(R)-2-(4-(7-((5-chloro-4-((3-(isopropylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanol;
(R)-1-(4-(7-((5-chloro-4-((3-(isopropylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanone;
(R)—$N^2$-(4-([1,4'-bipiperidin]-4-yl)-2,5-dimethyl-2,3-dihydrobenzofuran-7-yl)-5-chloro-$N^4$-(3-(isopropylsulfonyl)-1-methyl-1H-pyrazol-4-yl)pyrimidine-2,4-diamine;
(R)-5-chloro-$N^2$-(4-(1-isopropylpiperidin-4-yl)-2,5-dimethyl-2,3-dihydrobenzofuran-7-yl)-$N^4$-(3-(isopropylsulfonyl)-1-methyl-1H-pyrazol-4-yl)pyrimidine-2,4-diamine;
(R)-5-chloro-$N^2$-(4-(4-(isopropylamino)cyclohexyl)-2,5-dimethyl-2,3-dihydrobenzofuran-7-yl)-$N^4$-(3-(isopropylsulfonyl)-1-methyl-1H-pyrazol-4-yl)pyrimidine-2,4-diamine;
5-chloro-$N^2$-((2R)-2,5-dimethyl-4-(piperidin-3-yl)-2,3-dihydrobenzofuran-7-yl)-$N^4$-(3-(isopropylsulfonyl)-1-methyl-1H-pyrazol-4-yl)pyrimidine-2,4-diamine;
5-chloro-$N^2$-((2R)-2,5-dimethyl-4-(1-methylpiperidin-3-yl)-2,3-dihydrobenzofuran-7-yl)-$N^4$-(3-(isopropylsulfonyl)-1-methyl-1H-pyrazol-4-yl)pyrimidine-2,4-diamine;
5-chloro-$N^2$-((2R)-2,5-dimethyl-4-(pyrrolidin-3-yl)-2,3-dihydrobenzofuran-7-yl)-$N^4$-(3-(isopropylsulfonyl)-1-methyl-1H-pyrazol-4-yl)pyrimidine-2,4-diamine;
5-chloro-$N^2$-((2R)-2,5-dimethyl-4-(1-methylpyrrolidin-3-yl)-2,3-dihydrobenzofuran-7-yl)-$N^4$-(3-(isopropylsulfonyl)-1-methyl-1H-pyrazol-4-yl)pyrimidine-2,4-diamine;
(R)-5-chloro-$N^4$-(3-(isopropylsulfonyl)-1-methyl-1H-pyrazol-4-yl)-$N^2$-(2-methyl-4-(piperidin-4-yl)-2,3-dihydrobenzofuran-7-yl)pyrimidine-2,4-diamine;
(R)-5-chloro-$N^2$-(5-fluoro-2-methyl-4-(piperidin-4-yl)-2,3-dihydrobenzofuran-7-yl)-$N^4$-(3-(isopropylsulfonyl)-1-methyl-1H-pyrazol-4-yl)pyrimidine-2,4-diamine;
5-chloro-$N^2$-(2,6-dimethyl-5-(piperidin-4-yl)chroman-8-yl)-$N^4$-(3-(isopropylsulfonyl)-1-methyl-1H-pyrazol-4-yl)pyrimidine-2,4-diamine;

(R)-5-chloro-N⁴-(3-(isopropylsulfonyl)-1-methyl-1H-pyrazol-4-yl)-N²-(2-methyl-4-(1-methylpiperidin-4-yl)-2,3-dihydrobenzofuran-7-yl)pyrimidine-2,4-diamine;

(R)-5-chloro-N²-(5-fluoro-2-methyl-4-(1-methylpiperidin-4-yl)-2,3-dihydrobenzofuran-7-yl)-N⁴-(3-(isopropylsulfonyl)-1-methyl-1H-pyrazol-4-yl)pyrimidine-2,4-diamine;

5-chloro-N²-(2,6-dimethyl-5-(1-methylpiperidin-4-yl)chroman-8-yl)-N⁴-(3-(isopropylsulfonyl)-1-methyl-1H-pyrazol-4-yl)pyrimidine-2,4-diamine;

(S)-5-chloro-N⁴-(3-(isopropylsulfonyl)-1-methyl-1H-pyrazol-4-yl)-N²-(2-methyl-4-(piperidin-4-yl)-2,3-dihydrobenzofuran-7-yl)pyrimidine-2,4-diamine;

(S)-5-chloro-N⁴-(3-(isopropylsulfonyl)-1-methyl-1H-pyrazol-4-yl)-N²-(2-methyl-4-(1-methylpiperidin-4-yl)-2,3-dihydrobenzofuran-7-yl)pyrimidine-2,4-diamine;

5-chloro-N⁴-(3-(isopropylsulfonyl)-1-methyl-1H-pyrazol-4-yl)-N²-(7-(1-methylpiperidin-4-yl)-1,3-dihydroisobenzofuran-4-yl)pyrimidine-2,4-diamine;

(R)—N²-(2,5-dimethyl-4-(piperidin-4-yl)-2,3-dihydrobenzofuran-7-yl)-N⁴-(3-(isopropylsulfonyl)-1-methyl-1H-pyrazol-4-yl)thieno[3,2-d]pyrimidine-2,4-diamine;

(R)—N²-(2,5-dimethyl-4-(1-methylpiperidin-4-yl)-2,3-dihydrobenzofuran-7-yl)-N⁴-(3-(isopropylsulfonyl)-1-methyl-1H-pyrazol-4-yl)thieno[3,2-d]pyrimidine-2,4-diamine;

(R)-5-chloro-N⁴-(1-cyclopropyl-3-(isopropylsulfonyl)-1H-pyrazol-4-yl)-N²-(2,5-dimethyl-4-(piperidin-4-yl)-2,3-dihydrobenzofuran-7-yl)pyrimidine-2,4-diamine;

(R)-5-chloro-N²-(2,5-dimethyl-4-(piperidin-4-yl)-2,3-dihydrobenzofuran-7-yl)-N⁴-(1-isopropyl-3-(isopropylsulfonyl)-1H-pyrazol-4-yl)pyrimidine-2,4-diamine;

(R)-5-chloro-N²-(2,5-dimethyl-4-(piperidin-4-yl)-2,3-dihydrobenzofuran-7-yl)-N⁴-(1-ethyl-3-(isopropylsulfonyl)-1H-pyrazol-4-yl)pyrimidine-2,4-diamine;

(R)-5-chloro-N⁴-(1-cyclopropyl-3-(isopropylsulfonyl)-1H-pyrazol-4-yl)-N²-(2,5-dimethyl-4-(1-methylpiperidin-4-yl)-2,3-dihydrobenzofuran-7-yl)pyrimidine-2,4-diamine;

(R)-5-chloro-N²-(2,5-dimethyl-4-(1-methylpiperidin-4-yl)-2,3-dihydrobenzofuran-7-yl)-N⁴-(1-isopropyl-3-(isopropylsulfonyl)-1H-pyrazol-4-yl)pyrimidine-2,4-diamine;

(R)-5-chloro-N²-(2,5-dimethyl-4-(1-methylpiperidin-4-yl)-2,3-dihydrobenzofuran-7-yl)-N⁴-(1-ethyl-3-(isopropylsulfonyl)-1H-pyrazol-4-yl)pyrimidine-2,4-diamine;

(R)-5-chloro-N²-(2,5-dimethyl-4-(piperidin-4-yl)-2,3-dihydrobenzofuran-7-yl)-N⁴-(3-(isobutylsulfonyl)-1-methyl-1H-pyrazol-4-yl)pyrimidine-2,4-diamine;

(R)-5-chloro-N²-(2,5-dimethyl-4-(1-methylpiperidin-4-yl)-2,3-dihydrobenzofuran-7-yl)-N⁴-(3-(isobutylsulfonyl)-1-methyl-1H-pyrazol-4-yl)pyrimidine-2,4-diamine;

(R)-2-(4-(7-((5-chloro-4-((3-(isobutylsulfonyl)-1-methyl-1H-pyrazol-4-yl)amino)pyrimidin-2-yl)amino)-2,5-dimethyl-2,3-dihydrobenzofuran-4-yl)piperidin-1-yl)ethanol;

(R)-5-chloro-N⁴-(1-cyclopropyl-3-(isobutylsulfonyl)-1H-pyrazol-4-yl)-N²-(2,5-dimethyl-4-(piperidin-4-yl)-2,3-dihydrobenzofuran-7-yl)pyrimidine-2,4-diamine; and (R)-5-chloro-N⁴-(1-cyclopropyl-3-(isobutylsulfonyl)-1H-pyrazol-4-yl)-N²-(2,5-dimethyl-4-(1-methylpiperidin-4-yl)-2,3-dihydrobenzofuran-7-yl)pyrimidine-2,4-diamine.

9. A pharmaceutical composition comprising the compound or the pharmaceutically acceptable salt as defined in claim 1 as an active ingredient and one or more pharmaceutically acceptable carrier.

10. A method for the treatment of cellular proliferative diseases associated with protein kinases, using the compound or the pharmaceutically acceptable salt thereof as defined in claim 1, comprising the steps of:
preparing a medication comprising the compound or the pharmaceutically acceptable salt thereof; and
administering to a recipient in need thereof a therapeutically effective amount of the medication.

11. A method for the treatment of cellular proliferative diseases associated with anaplastic lymphoma kinase, using the compound or the pharmaceutically acceptable salt thereof as defined in claim 1, comprising the steps of:
preparing a medication comprising the compound or the pharmaceutically acceptable salt thereof; and
administering to a recipient in need thereof a therapeutically effective amount of the medication.

12. The method according to claim 10, wherein the is cellular proliferative diseases is selected from the group consisting of non-small cell lung cancer, anaplastic large cell lymphoma, inflammatory myofibroblastic tumor, nasopharyngeal cancer, breast cancer, colorectal cancer, diffuse large B-cell lymphoma, liver cancer, gastric cancer, esophagus cancer, pancreatic cancer, ovarian cancer, systemic histiocytosis and neuroblastoma.

13. The compound according to claim 2, wherein the aryl is phenyl, naphthyl or anthryl; the heterocyclyl is morpholinyl, piperidyl, pyranyl, pyrazolyl, furyl, pyridyl or pyrimidinyl; and the halogen is selected from one or more of the group consisting of fluorine, chlorine, bromine and iodine.

14. The compound according to claim 3, wherein the aryl is phenyl, naphthyl or anthryl; the heterocyclyl is morpholinyl, piperidyl, pyranyl, pyrazolyl, furyl, pyridyl or pyrimidinyl; and the halogen is selected from one or more of the group consisting of fluorine, chlorine, bromine and iodine.

15. The compound according to claim 4, wherein the aryl is phenyl, naphthyl or anthryl; the heterocyclyl is morpholinyl, piperidyl, pyranyl, pyrazolyl, furyl, pyridyl or pyrimidinyl; and the halogen is selected from one or more of the group consisting of fluorine, chlorine, bromine and iodine.

16. The compound according to claim 5, wherein the aryl is phenyl, naphthyl or anthryl; the heterocyclyl is morpholinyl, piperidyl, pyranyl, pyrazolyl, furyl, pyridyl or pyrimidinyl; and the halogen is selected from one or more of the group consisting of fluorine, chlorine, bromine and iodine.

17. The compound according to claim 6, wherein the aryl is phenyl, naphthyl or anthryl; the heterocyclyl is morpholinyl, piperidyl, pyranyl, pyrazolyl, furyl, pyridyl or pyrimidinyl; and the halogen is selected from one or more of the group consisting of fluorine, chlorine, bromine and iodine.

* * * * *